United States Patent [19]

Mikoshiba et al.

[11] Patent Number: 5,667,959
[45] Date of Patent: Sep. 16, 1997

[54] SILVER HALIDE PHOTOGRAPHIC MATERIAL AND HYDROXAMIC ACID BASED COMPOUND USED THEREFOR

[75] Inventors: Hisashi Mikoshiba; Hiroo Takizawa; Junichiro Hosokawa; Yoshio Ishii; Keiji Mihayashi; Masakazu Morigaki, all of Kanagawa, Japan

[73] Assignee: Fuji Photo Film Co., Ltd., Kanagawa, Japan

[21] Appl. No.: 519,019

[22] Filed: Aug. 24, 1995

[30] Foreign Application Priority Data

Aug. 25, 1994 [JP] Japan .................... 6-222731
Mar. 10, 1995 [JP] Japan .................... 7-078443
Jun. 14, 1995 [JP] Japan .................... 7-170457

[51] Int. Cl.$^6$ .................................. G03C 1/34
[52] U.S. Cl. .................... 430/607; 430/611; 430/613
[58] Field of Search ............................. 430/607, 611, 430/613

[56] References Cited

U.S. PATENT DOCUMENTS

| | | | |
|---|---|---|---|
| 4,330,606 | 5/1982 | Sobel et al. | 430/17 |
| 4,339,515 | 7/1982 | Schranz et al. | 430/17 |
| 4,483,919 | 11/1984 | Kobayashi et al. | |
| 5,202,225 | 4/1993 | Nakamine et al. | 430/566 |
| 5,206,131 | 4/1993 | Matsuda et al. | 430/559 |
| 5,254,724 | 10/1993 | Bergeron, Jr. | |

FOREIGN PATENT DOCUMENTS

| | | |
|---|---|---|
| A30384912 | 8/1990 | European Pat. Off. |
| A10451833 | 10/1991 | European Pat. Off. |
| 59-121328 | 7/1984 | Japan |
| 59-198453 | 11/1984 | Japan |
| 5-241306 | 9/1993 | Japan |
| WO9209556 | 6/1992 | WIPO |

OTHER PUBLICATIONS

Chamical Abstracts 120:231861 corresponding to JP 5-241206 1994.
Chemical Abstracts 102:157901 corresponding to JP 59-121328 1985.
Nucleophilic Cleavage of Phosphate Triesters in Dialkylammonium Bilayer Membranes, *Bulletin of Chemical Society of Japan*, vol. 54, No. 7, 1981, pp. 2072–2078.
Spermexatin and Spermexatol: New Synthetic Spermidine-Based Siderophore Analogues, *Journal of Medical Chemistry*, vol. 32, No. 2, 1989, pp. 357–367.

*Primary Examiner*—Thorl Chea
*Attorney, Agent, or Firm*—Sughrue, Mion, Zinn, Macpeak, and Seas.

[57] ABSTRACT

A silver halide photographic material is disclosed, which comprises a support having thereon at least one light-sensitive silver halide emulsion layer, wherein said silver halide photographic material contains at least one compound represented by the following formula (I):

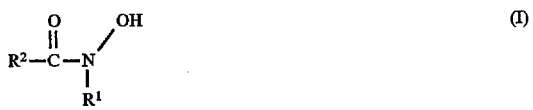

wherein $R^1$ represents a substituted or unsubstituted alkyl group having from 1 to 6 carbon atoms; and $R^2$ represents a branched alkyl group having 20 or more carbon atoms, a straight chain or branched alkenyl group having 17 or more carbon atoms, or a substituted alkyl or substituted alkenyl group substituted with at least one substituent selected from the group consisting of an alkoxycarbonyl group, an alkenoxycarbonyl group, an aryloxycarbonyl group, a carbamoyl group, an acyl group, an alkoxyl group, an alkylthio group, an arylthio group, an alkylsulfonyl group, an arylsulfonyl group, an aryl group and a heterocyclic group, and having 12 or more carbon atoms in total.

13 Claims, No Drawings

SILVER HALIDE PHOTOGRAPHIC MATERIAL AND HYDROXAMIC ACID BASED COMPOUND USED THEREFOR

FIELD OF THE INVENTION

The present invention relates to a light-sensitive silver halide photographic material and, more particularly, to a silver halide photographic material which produces less fluctuation in the photographic properties during storage after production and after photographing until development processing.

The present invention also relates to a silver halide photographic material which generates less fog.

Further, the present invention relates to a novel hydroxamic acid based compound which provides photographically useful effect.

BACKGROUND OF THE INVENTION

A silver halide photographic material is required to be high sensitive and produce less fluctuation in the photographic properties during storage after production and after photographing until development processing.

Of the fluctuation of the photographic properties after photographing until development processing, with respect to the prevention of latensification, a method of using a hardening agent having an active vinyl group in combination with a triazine based compound is disclosed in JP-A-59-162546 (the term "JP-A" as used herein means a "published unexamined Japanese patent application").

However, the above method is not sufficient in the preventing effect and a further improvement has been desired.

On the other hand, in a full color photographic materials a multilayer structure comprising a plurality of emulsions having different spectral sensitivities is used to achieve the object of a full color photograph. However, although the emulsions for such a usage have been considerably improved, fog, intensification and fading of a latent image are liable to occur, therefore, they are not necessarily sufficient. 2-Hydroxyamino-1,3,5-triazines, for example, are useful for the improvement of such storage stabilities. However, the storage stability of each layer varies according to the emulsion used in each layer. Therefore, a method to improve the storage stability of the latent image of the emulsion of a specific layer has been strongly desired in recent years.

Many of known 2-hydroxylamine-1,3,5-triazines are diffusible, therefore, they have a drawback such that their effects are exerted to emulsions of layers other than the objective layer. On the other hand, hydroxamic acids having a specific structure are disclosed in U.S. Pat. No. 4,339,515, 4,330,606, JP-A-59-198453 and JP-A-3-293666, but the use purposes of them are different from the object of the present invention and, further, their effects of the improvement of the storage stability of a latent image and the functions to the emulsion of solely a specific layer are not sufficient. Accordingly, the development of a method to largely improve the storage stability of the latent image of only the objective layer has been strongly desired.

The present invention is to provide a method to improve the above described storage stability of the emulsion and the stability of the latent image of a specific layer.

The present inventors have eagerly studied the method of improving the storage stability of the emulsion produced and the storage stability of the latent image to solve the above problems. As a result of various investigation particularly about the carbon atom number and the kinds of the substituents, a completely novel N-alkylhydroxamic acid based compound of the present invention has been discovered.

Further, it has been found that the compound of the present invention can achieve the objects of the present invention, when added to a silver halide photographic material, without changing the hue of the color formed, affecting the dye-forming speed of the coupler, accelerating the decomposition of the coupler and the color formed, deteriorating the film strength, or fogging the emulsion.

Moreover, of the compounds for use in the present invention, the compound represented by formula (III) is a completely novel compound which has not been known in the past. The photographic usefulness of this compound has become clear solely by the investigation of the present inventors.

SUMMARY OF THE INVENTION

One object of the present invention is to provide a compound which is very effective to improve the storage stability of the silver halide emulsion and the storage stability of the latent image and also a method of improving the storage stability of the latent image using said compound.

Another object of the present invention is to provide a compound which improves the storage stability of the latent image of solely a specific layer and a method of improving the storage stability of the latent image using said compound.

A further object of the present invention is to provide a compound which improves the storage stability of the latent image without adversely affecting various photographic properties when added to a photographic material and a method of improving the storage stability of the latent image using said compound.

The above objects of the present invention have been achieved by the following (1), (2) and (3).

(1) A silver halide photographic material comprising a support having thereon at least one light-sensitive silver halide emulsion layer, wherein said silver halide photographic material contains at least one compound represented by the following formula (I):

wherein $R^1$ represents a substituted or unsubstituted alkyl group having from 1 to 6 carbon atoms; and $R^2$ represents a branched alkyl group having 20 or more carbon atoms, a straight chain or branched alkenyl group having 17 or more carbon atoms, or a substituted alkyl or substituted alkenyl group substituted with at least one substituent selected from the group consisting of an alkoxycarbonyl group, an alkenoxycarbonyl group, an aryloxycarbonyl group, a carbamoyl group, an acyl group, an alkoxyl group, an alkylthio group, an arylthio group, an alkylsulfonyl group, an arylsulfonyl group, an aryl group and a heterocyclic group, and having 12 or more carbon atoms in total.

(2) The silver halide photographic material as described in the above (1), wherein the compound represented by formula (I) is represented by formula (II):

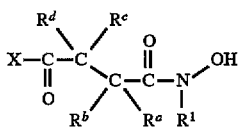

(II)

wherein $R^1$ represents a substituted or unsubstituted alkyl group having from 1 to 6 carbon atoms; $R^a$, $R^b$, $R^c$ and $R^d$ each independently represents a hydrogen atom, a substituted or unsubstituted alkyl group having from 1 to 18 carbon atoms, or a substituted or unsubstituted alkenyl group having from 2 to 18 carbon atoms; X represents —$OR^6$ or —$N(R^6)(R^7)$; and $R^6$ and $R^7$, which may be the same or different, each represents a hydrogen atom, a substituted or unsubstituted alkyl group having from 1 to 22 carbon atoms, a substituted or unsubstituted alkenyl group having from 2 to 22 carbon atoms, or an aryl group having from 6 to 22 carbon atoms.

(3) A compound represented by the following formula

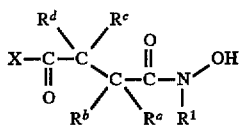

(II)

wherein $R^1$, $R^a$, $R^b$, $R^c$, $R^d$, X, $R^6$ and $R^7$ have the same meaning as in (2) above, provided that when all of $R^a$, $R^b$, $R^c$ and $R^d$ represent hydrogen atoms, $R^6$ and $R^7$ represent a substituted or unsubstituted alkyl group having 14 or more carbon atoms or an aryl group having from 6 to 22 carbon atoms.

DETAILED DESCRIPTION OF THE INVENTION

Formula (I) is described in detail below.

In formula (I), $R^1$ represents a substituted or unsubstituted alkyl group. $R^1$ may be unsubstituted or substituted with a substituent.

$R^1$ preferably has from 1 to 6 carbon atoms. Preferred specific examples thereof include methyl, ethyl, n-propyl, isopropyl, n-butyl, sec-butyl, t-butyl, n-pentyl, isopentyl, neopentyl, and n-hexyl.

Substituents for these alkyl groups include, for example, an alkyl group, an alkenyl group, an aryl group, a heterocyclic group, a halogen atom, an alkoxyl group, an aryloxy group, an alkylthio group, an arylthio group, a cyano group, a nitro group, an alkoxycarbonyl group, an aryloxycarbonyl group, a hydroxyl group, an acyl group, an acyloxy group, an alkylsulfonyl group, an arylsulfonyl group, an acylamino group, an alkylsulfonamido group or an arylsulfonamido group, and specific examples include 2-chloroethyl, 2-methoxyethyl, 2-cyanoethyl, 2-ethoxycarbonylethyl, 3-methylthiopropyl, 2-acetylaminoethyl, 3-hydroxypropyl, 2-acetyloxyethyl, 3-chloroethyl, 3-methoxyethylallyl, and pulenyl.

$R^1$ preferably represents an unsubstituted alkyl group, particularly preferably a methyl group.

$R^2$ preferably represents a branched alkyl group having 20 or more carbon atoms, a straight chain or branched alkenyl group having 17 or more carbon atoms, or a substituted alkyl or substituted alkenyl group substituted with at least one substituent selected from the group consisting of an alkoxycarbonyl group, an alkenoxycarbonyl group, an aryloxycarbonyl group, a carbamoyl group, an acyl group, an alkoxyl group, an alkylthio group, an arylthio group, an alkylsulfonyl group, an arylsulfonyl group, an aryl group and a heterocyclic group, and having 12 or more carbon atoms in total.

Formula (I) is described further in detail below.

In one preferred embodiment of the present invention, $R^2$ represents an unsubstituted alkyl group.

When $R^2$ represents an alkyl group, the unsubstituted alkyl group is preferably a branched alkyl group having from 20 to 60 carbon atoms. Specific example thereof includes the following structural formula:

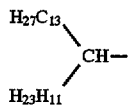

In another preferred embodiment of the present invention, $R^2$ represents a straight chain or branched alkenyl group having from 17 to 60 carbon atoms. Specific examples thereof include 1-octadecenyl and 2-octadecenyl.

In another preferred embodiment of the present invention, $R^2$ represents an alkyl or alkenyl group substituted with at least one substituent and having from 12 to 60 carbon atoms in total.

Preferred substituents for the alkyl group include an alkoxycarbonyl group, an alkenoxycarbonyl group, an aryloxycarbonyl group, a carbamoyl group, an acyl group, an alkoxyl group, an alkylthio group, an arylthio group, an alkylsulfonyl group, an arylsulfonyl group, an aryl group or a heterocyclic group.

Preferred of them are an alkoxy group, an aryloxy group, an alkoxycarbonyl group, an aryloxycarbonyl group, a carbamoyl group and an amino group (including an anilino group). Specific examples thereof are described below: an alkoxyl group (having from 1 to 22 carbon atoms, e.g., methoxy, ethoxy, n-propoxy, isopropoxy, n-butoxy, n-pentoxy, n-hexyloxy, n-octyloxy, stearyloxy, dodecyloxy, eicosyloxy, docosyloxy, oleyloxy).

As the specific examples of the alkoxyl group, alkoxyl groups derived from higher alcohols such as Fine Oxocole, 140, 1600, 1800, 180, 180N, 2000, 2600 (trade names, Nippon Chemical Industries, Co., Ltd.) can also be cited.

An aryloxy group (having from 6 to 16 carbon atoms, e.g., phenoxy, p-methoxyphenoxy, m-octyloxyphenoxy, o-chlorophenoxy, 2,4-di-t-octylphenoxy). An alkoxycarbonyl group (having from 2 to 23 carbon atoms, e.g., methoxycarbonyl, ethoxycarbonyl, n-butoxycarbonyl, isopropoxycarbonyl, t-butoxycarbonyl, n-octyloxycarbonyl, n-dodocyloxycarbonyl, pentadecyloxycarbonyl, stearyloxycarbonyl, oleyloxycarbonyl, docosyloxycarbonyl). As the specific examples of the alkoxycarbonyl group, alkoxycarbonyl groups derived from higher alcohols such as Fine Oxocole, 140, 1600, 1800, 180, 180N, 2000, 2600 (trade names, Nippon Chemical Industries, Co., Ltd.) can also be cited.

An aryloxycarbonyl group (having from 6 to 17 carbon atoms, e.g., phenoxycarbonyl, p-ethoxyphenoxycarbonyl, m-dodecyloxyphenoxycarbonyl, o-chlorophenoxycarbonyl, 2,4-di-t-octylphenoxycarbonyl). A carbamoyl group (having from 3 to 37 carbon atoms, e.g., dimethylcarbamoyl, diethylcarbamoyl, dioctylcarbamoyl, distearylcarbamoyl, dioleylcarbamoyl, bis(2-ethylhexyl)carbamoyl, stearyloxypropylcarbamoyl). An amino group (having from 1 to 22 carbon atoms, e.g., octylamino, dioctylamino, stearylamino, distearylamino, oleylamino, dioleylamino, methylamino, anilino).

Preferred structure of the compound represented by formula (I) for use in the present invention is such that $R^1$ is a substituted or unsubstituted alkyl group having from 1 to 6 carbon atoms and $R^2$ is represented by the following formula (I-A):

$$R^4\text{—}L\text{—}R^3\text{—} \qquad (I\text{-}A)$$

wherein $R^3$ represents an alkylene group having from 2 to 20 carbon atoms or an alkenylene group having from 2 to 20 carbon atoms; $R^4$ represents a substituted or unsubstituted alkyl group having from 1 to 30 carbon atoms, a substituted or unsubstituted aryl group having from 6 to 20 carbon atoms, a substituted or unsubstituted alkenyl group having from 2 to 18 carbon atoms, or a substituted or unsubstituted heterocyclic group having from 2 to 20 carbon atoms; L represents —CO—, —SO$_2$—, —O—, —S—, —COO—, —OCO—, —CON(R$^5$)— or —N(R$^5$)CO—; $R^5$ represents a hydrogen atom or a substituted or unsubstituted alkyl group having from 1 to 18 carbon atoms, provided that when L represents —O—, $R^4$ represents a substituted or unsubstituted alkyl group having from 1 to 40 carbon atoms; the total carbon atom number of $R^3$, L and $R^4$ is preferably 12 or more.

In formula (I-A), $R^3$ represents an alkylene or alkenylene group having from 2 to 20 carbon atoms, preferably a 1,2-ethylene group, a 1,3-propylene group or a substituted 1,2-ethylene group.

Specific examples of $R^3$ are shown below.

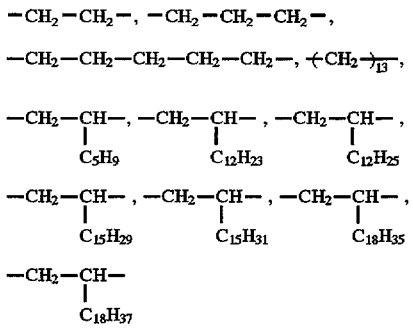

$R^4$, of the above, preferably represents a substituted or unsubstituted alkyl group having from 1 to 30 carbon atoms or a substituted or unsubstituted alkenyl group having from 2 to 18 carbon atoms, more preferably a substituted or unsubstituted alkyl or alkenyl group having from 6 to 22 carbon atoms.

An unsubstituted group represented by $R^4$ includes stearyl, palmityl, myristyl, dodecyl, and methyl group. A substituted alkyl group represented by $R^4$ includes 2-methoxyethyl and 2-diethylaminoethyl group. An unsubstituted aryl group represented by $R^4$ includes phenyl and naphthyl group. A substituted aryl group represented by $R^4$ includes 2,4-di-t-octylphenyl and p-n-dodecylphenyl group. An unsubstituted heterocyclic group represented by $R^4$ includes morpholino and piperazino group. A substituted heterocyclic group represented by $R^4$ includes, for example, 2-methylimidazo-1-yl group.

An unsubstituted alkyl group represented by $R^5$ includes n-octyl, methyl, ethyl, isopropyl, n-dodecyl, stearyl, myristyl and 2-ethylhexyl group. A substituted alkyl group represented by $R^5$ includes 2-methoxyethyl, 3-methoxypropan-1-yl and 2-chloroethyl group;

L represents —CO—, —O—, SO$_2$—, —S—, —COO—, —OCO—, —CON(R$^5$)— or —N(R$^5$)CO—, preferably —O—, —O——CO— or —N(R$^5$)CO—.

Above all, $R^4$—L— preferably represents an alkoxycarbonyl group, an alkenoxycarbonyl group, an aryloxycarbonyl group, a carbamoyl group, an acyl group, an alkoxyl group, an alkylthio group, an arylthio group, an alkylsulfonyl group or an arylsulfonyl group.

The total carbon atom number of $R^3$, L and $R^4$ is preferably from 12 to 60.

The compound represented by formula (I) is most preferably represented by the following formula (II):

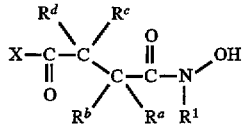

wherein $R^1$ represents a substituted or unsubstituted alkyl group having from 1 to 6 carbon atoms; $R^a$, $R^b$, $R^c$ and $R^d$, which may be the same or different, each represents a hydrogen atom, a substituted or unsubstituted alkyl group having from 1 to 18 carbon atoms, or a substituted or unsubstituted alkenyl group having from 2 to 18 carbon atoms; X represents —OR$^6$ or —N(R$^6$)(R$^7$)—, and $R^6$ and $R^7$ each independently represents a hydrogen atom, a substituted or unsubstituted alkyl group having from 1 to 22 carbon atoms, a substituted or unsubstituted alkenyl group having from 2 to 2 carbon atoms, or a substituted or unsubstituted aryl group having from 6 to 22 carbon atoms.

Substituent which may be substituted on the alkyl, alkenyl and aryl group represented by $R^a$, $R^b$, $R^c$, $R^d$, $R^6$ or $R^7$ is the same as that substituted on the alkyl group represented by $R^1$.

$R^1$ preferably represents a methyl group, an ethyl group or an n-hexyl group; $R^a$, $R^b$, $R^c$ and $R^d$ all preferably represent hydrogen atoms, or preferably at least one of $R^a$, $R^b$, $R^c$ and $R^d$ represents an alkyl or alkenyl group having from 5 to 18 carbon atoms and the others represent hydrogen atoms; $R^6$ preferably represents an alkyl or alkenyl group having from 6 to 22 carbon atoms, provided that when all of $R^a$, $R^b$, $R^c$ and $R^d$ represent hydrogen atoms, $R^6$ preferably has 14 or more carbon atoms; $R^7$ preferably represents an an alkyl group having from 6 to 18 carbon atoms; and as a group represented by X, —OR$^6$ is preferred to —NR$^6$R$^7$.

One most preferred constitution of formula (II) is such that $R_a$ represents an alkenyl or alkyl group having from 12 to 18 carbon atoms, $R^b$, $R^c$ and $R^d$ represent hydrogen atoms, $R^1$ represents a methyl group, an ethyl group or an n-hexyl group, X represents —OR$^6$, and $R^6$ represents an alkyl or alkenyl group having from 12 to 18 carbon atoms.

Another most preferred constitution of formula (II) is such that $R^c$ represents an alkenyl or alkyl group having from 12 to 18 carbon atoms, $R^a$, $R^b$ and $R^d$ represent hydrogen atoms, $R^1$ represents a methyl group, an ethyl group or an n-hexyl group, X represents —OR$^6$, and $R^6$ represents an alkyl or alkenyl group having from 12 to 18 carbon atoms.

Still another most preferred constitution of formula (II) is such that $R^a$, $R^b$, $R_c$ and $R^d$ all represent hydrogen atoms, X represents —OR$^6$, $R^6$ represents an alkyl or alkenyl group having from 12 to 18 carbon atoms, and $R^1$ represents a methyl, ethyl or n-hexyl group.

Of the compounds represented by formula (II) of the present invention, most preferably $R^a$, $R^b$, $R^c$ and $R^d$ all represent hydrogen atoms, $R^6$ represents a myristyl group, a palmityl group or a stearyl group, and $R^1$ represents a methyl group, an ethyl group or an n-hexyl group.

Compounds represented by formula (I) preferably have a molecular weight of 250 or more, more preferably 300 or more, and most preferably 330 or more, and 800 or less and more preferably 600 or less.

The compound of the present invention should be substantially water-insoluble as it is nondiffusible in gelatin film. "Substantially water-insoluble" means the solubility in water of 25° C. is 5% or less, preferably 1% or less.

The raw material of the compound of the present invention (e.g., acid anhydrides and alcohols as described below) is sometimes available only as a mixture of isomer and homolog. Therefore, the compound of the present invention is sometimes easier to synthesize as a mixture of isomer and homolog. In such a case, the compound of the present invention is preferably added to a silver halide photographic material as a mixture.

Specific examples of the compounds of the present invention are shown below, but the present invention is not limited thereto.

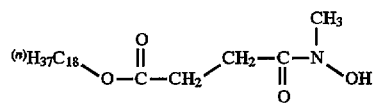

1.

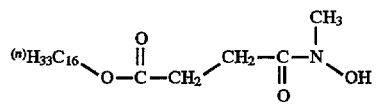

2.

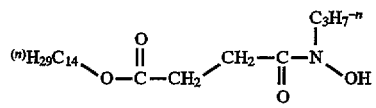

3.

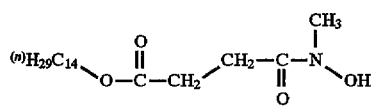

4.

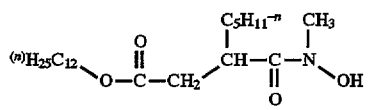

5.

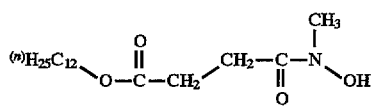

6.

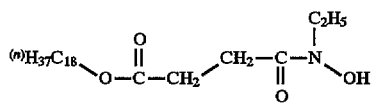

7.

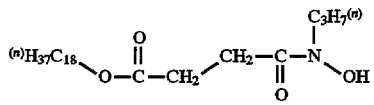

8.

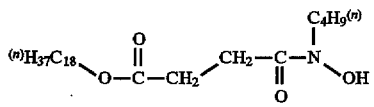

9.

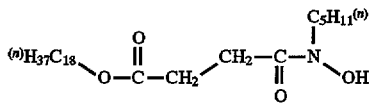

10.

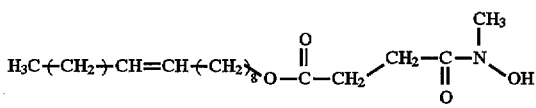

11.

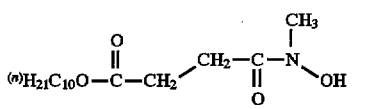

12.

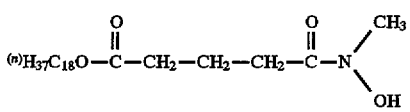

13.

-continued
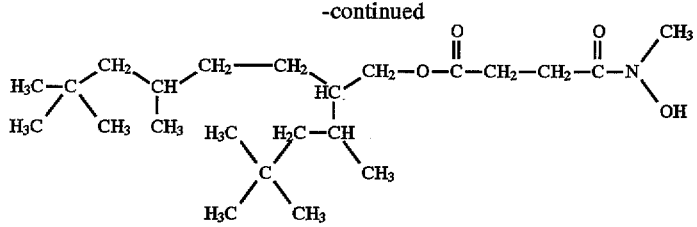 14.
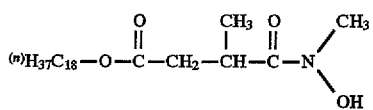 15.
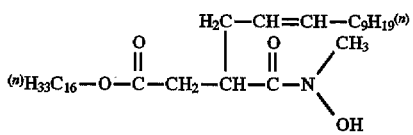 16.
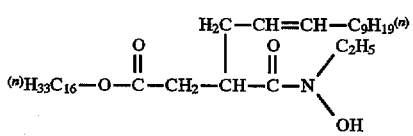 17.
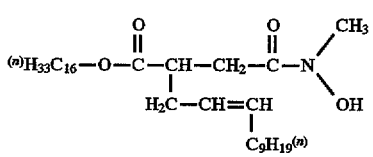 18.
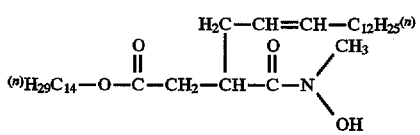 19.
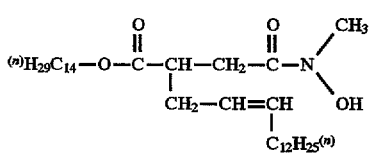 20.
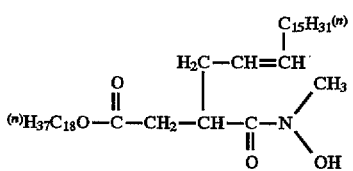 21.
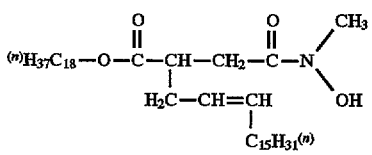 22.
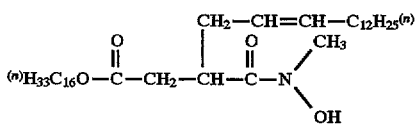 23.
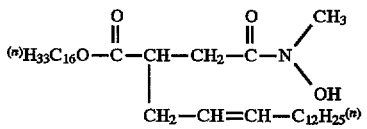 24.

-continued
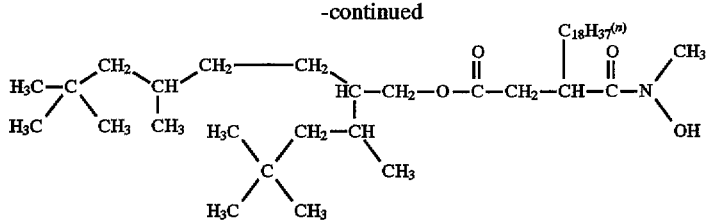 25.
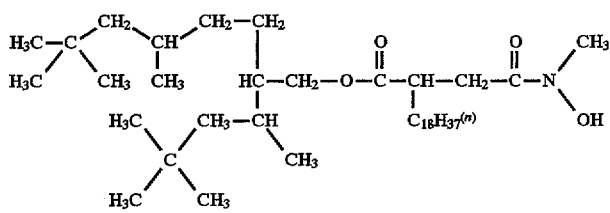 26.
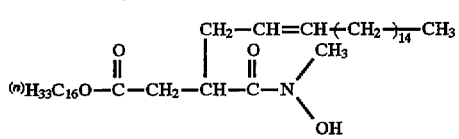 27.
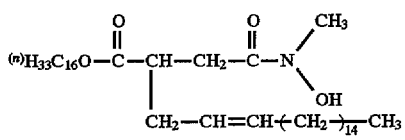 28.
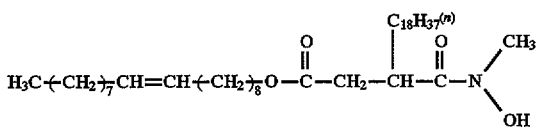 29.
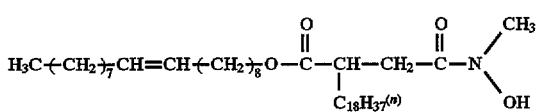 30.
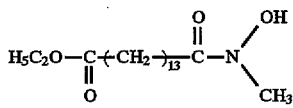 31.
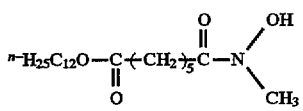 32.
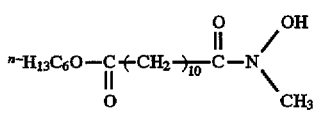 33.
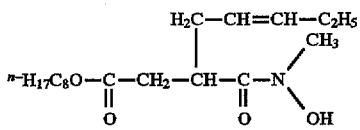 34.
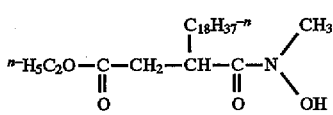 35.
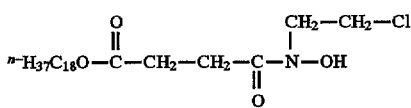 36.

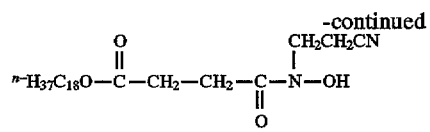
37.
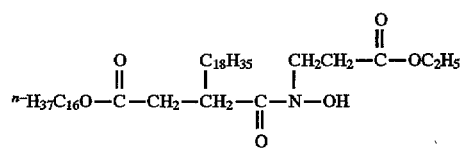
38.
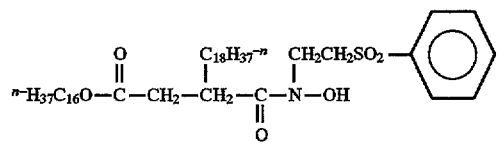
39.
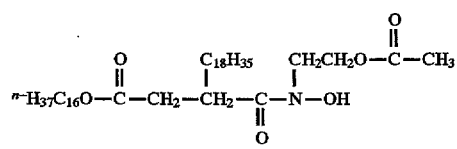
40.
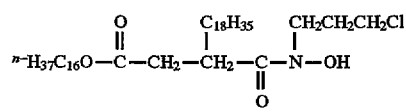
41.
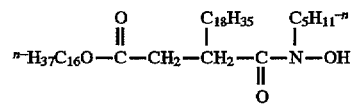
42.
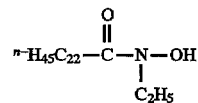
43.
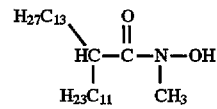
44.
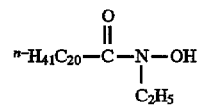
45.
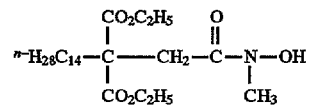
46.
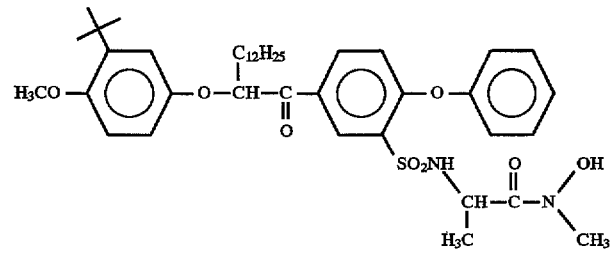
47.
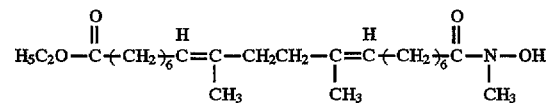
48.

-continued
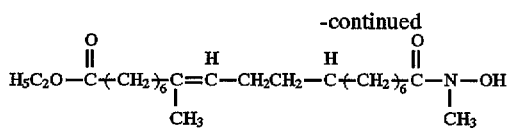
49.
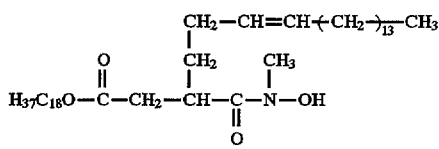
50.
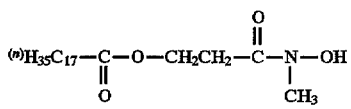
51.
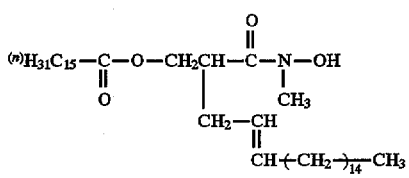
52.
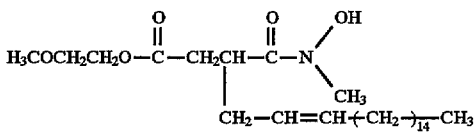
53.
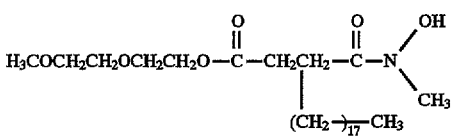
54.
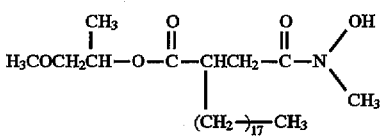
55.
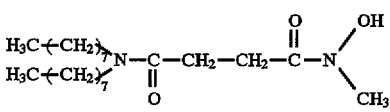
56
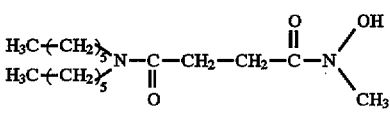
57
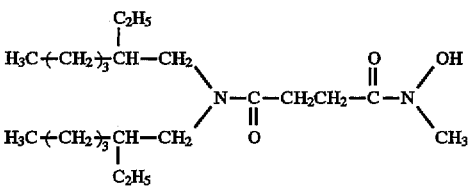
58
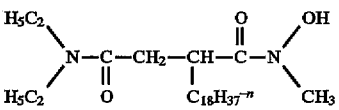
60
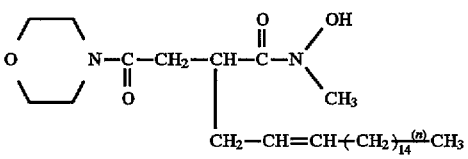
61

General synthesis methods of the compound of the present invention are described below.

The compound of the present invention can be obtained by condensing the corresponding carboxylic acid chloride and N-alkylhydroxylamine. When the corresponding carboxylic acid is easily available, carboxylic acid chloride can easily be obtained by treating the carboxylic acid with thionyl chloride and oxalyl chloride. When a carboxylic acid is complicated, after synthesizing a carboxylic acid according to the corresponding synthesis method, carboxylic acid chloride can be obtained by treating the carboxylic acid with thionyl chloride and oxalyl chloride. A carboxylic acid can be synthesized according to synthesis methods described below.

On the other hand, N-alkylhydroxylamine whose alkyl group is a methyl group is commercially available. Others can be synthesized according to the following methods.

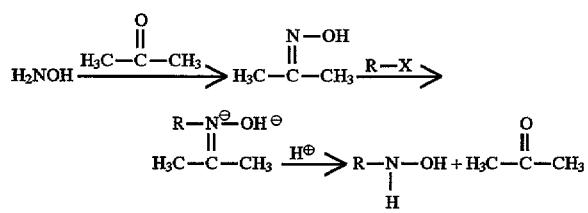

Acetone is added to hydroxylamine and converted to acetoxime, the converted product is reacted with an alkylating agent to synthesize an N-alkyl product (nitron). An acid treatment is conducted thereafter to eliminate the acetone and N-alkylhydroxylamine can be obtained.

The present invention will be further described in detail below by the synthesis examples of the compounds of the present invention.

SYNTHESIS EXAMPLE 1

Synthesis of Compound 1

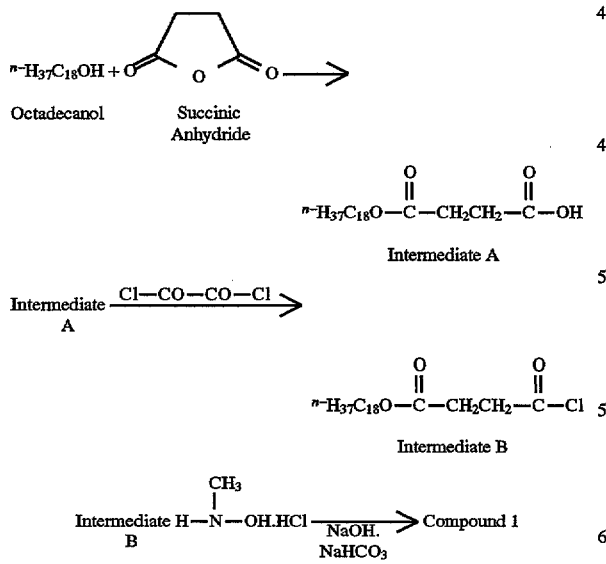

(1) 135 g of n-octadecanol and 50 g of succinic anhydride were put in a three-neck flask having a capacity of 300 ml and allowed to react at 120° C. for 6 hours. 50 ml of ethyl acetate was added thereto to crystallize. The obtained crystals were recovered by filtration under reduced pressure and washed with ethyl acetate. The crystals were air-dried and 165 g of Intermediate A was obtained (yield: 89.1%).

(2) 30 g of Intermediate A and 30 ml of methylene chloride were put in a three-neck flask having a capacity of 200 ml and 1 ml of dimethylformamide was added thereto with stirring. 12.3 g of oxalyl chloride was dropwise added thereto over 30 minutes with the inner temperature of the flask maintaining 20° C. and the reaction mixture was allowed to react for further 1 hour. The remaining oxalyl chloride and methylene chloride were removed under reduced pressure by an aspirator and Intermediate B was obtained. The obtained Intermediate B was used in the next step as it was.

(3) 2.40 g of sodium hydroxide and 100 ml of water were put in a three-neck flask having a capacity of 1.0 liter and dissolved, then the solution was ice-cooled. Under the nitrogen atmosphere at the inner temperature of 10° C. 5.0 g of N-hydroxylamine hydrochloride was added, subsequently 10.1 g of sodium bicarbonate and 100 ml of ethyl acetate were added thereto. With vigorously stirring and maintaining the inner temperature at 5° to 10° C., a mixture of 25 g of Intermediate B and 200 ml of ethyl acetate was dropwise added over 30 minutes. After the system was allowed to react for 2 hours, the temperature of the reaction solution was raised to 50° C. and the solution was separated. The organic layer was washed with water two times and dried with magnesium sulfate. After filtration, the solvent was removed under reduced pressure by an evaporator. The thus obtained crude product was refined with a silica gel column chromatography (ethyl acetate/hexane=1/10) and 19.1 g of Compound 1 was obtained (yield: 79.8%).

SYNTHESIS EXAMPLE 2

Synthesis of Compounds 21 and 22

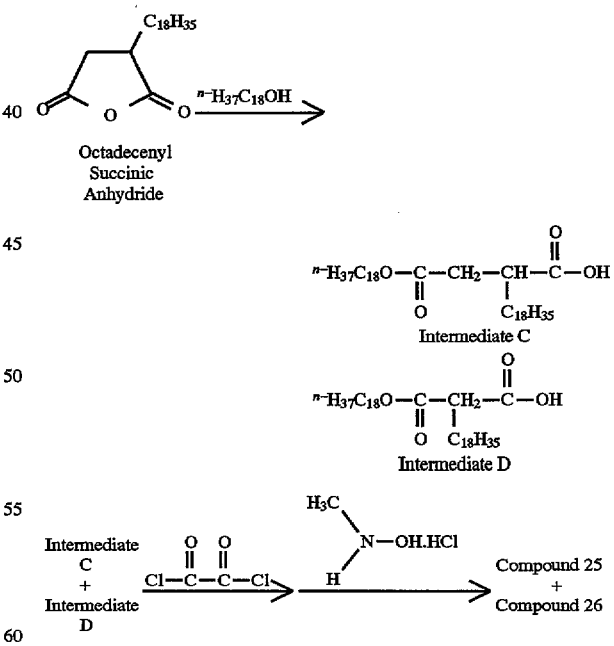

(1) 300 g of octadecenyl succinic anhydride and 232 g of octadecanol were put in a three-neck flask having a capacity of 1.0 liter and allowed to react for 9 hours at 80° C. After the reaction system was cooled to 60° C., 300 ml of acetonitrile was added, and the reaction system was allowed to stand to cool to room temperature to crystallize. 200 ml of acetonitrile was added thereto, and filtrated under reduced pressure. The obtained crystals were thoroughly washed with acetonitrile, and recrystallized with acetonitrile and 511 g of a mixture of Intermediate C and Intermediate D was obtained (yield: 96.0%).

(2) 200 g of the mixture of Intermediates C and D and 200 ml of methylene chloride were put in a three-neck flask having a capacity of 1.0 liter, and then 2.0 ml of dimethylformamide was added. 53.2 g of oxalyl chloride was dropwise added to the mixed solution over 30 minutes at 20° C. The reaction mixture was allowed to stand to react for further 2 hours, then the remaining oxalyl chloride and methylene chloride were removed under reduced pressure by an aspirator and acid chloride of Intermediates C and D was obtained. The obtained acid chloride was used in the next step as it was.

(3) Reaction was conducted in the same manner as in step (3) of Synthesis Example 1 using 29.4 g of N-methylhydroxamic acid hydrochloride, 14.1 g of sodium hydroxide, 59.1 g of sodium bicarbonate, the whole amount of the acid chloride of Intermediates C and D obtained in step (2) above, 500 ml of water, and 900 ml of ethyl acetate, and crystals of a mixture of Compounds 21 and 22 were obtained. The crystals were separated with a silica gel column chromatography, thus 70 g of Compound 21 and 25 g of Compound 22 were obtained.

SYNTHESIS EXAMPLE 3

Synthesis of Compound 56

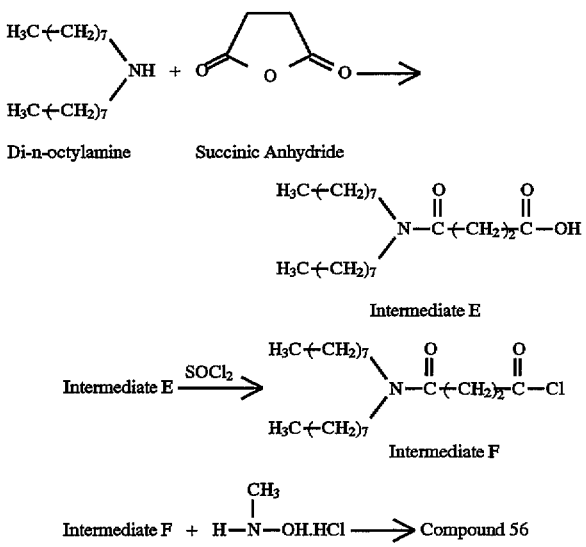

(1) 81 g of di-n-octylamine, 33.6 g of succinic anhydride and 100 ml of acetonitrile were put in a three-neck flask and allowed to react at 40° C. for 1 hour. Water was added thereto and the reaction solution was extracted with ethyl acetate. The organic phase was washed with water two times, dried with magnesium sulfate and concentrated to thereby obtained 106 g of oily Intermediate E. The obtained Intermediate E was used in the next step as it was.

(2) 50 g of Intermediate E, 100 ml of methylene chloride, and 0.2 ml of dimethylformaide were put in a three-neck flask and stirred. 19.2 g of thionyl chloride was dropwise added thereto under room temperature and the reaction mixture was allowed to react for 30 minutes at 40° C. The remaining thionyl chloride and methylene chloride were removed under reduced pressure by an aspirator and 52.7 g of Intermediate F was obtained.

(3) 200 ml of water, 6.1 g of sodium hydroxide, and 12.8 g of N-methylhydroxylamine hydrochloride were stirred under the nitrogen atmosphere. Subsequently, 12.8 g of N-methylhydroxylamine, 25.7 g of sodium hydrogencarbonate, and 200 ml of ethyl acetate were added thereto. 42.7 g of Intermediate F was dissolved in 50 ml of methylene chloride and the solution was dropwise added to the above reaction mixture with ice-cooling. After the system was allowed to react for 30 minutes, the temperature thereof was raised to 40° C. and the solution was separated. After the organic phase was washed with water two times, the system was concentrated under reduced pressure and the crude product of Compound 56 was obtained. The thus obtained crude product was refined with a silica gel column chromatography and 39.2 g of refined product was obtained.

Compounds 1 to 61 of the present invention can be easily synthesized according to the above synthesis methods.

Values of physical properties of the representative compounds of the present invention are shown below.

Compound 4
Appearance: white crystal
Melting Point: 68°–69° C.
NMR Spectrum: (300 MHz) $\delta$ (CDCl$_3$): 0.90 (3H, d, J6), 1.27 (22H, bs), 1.6.1 (2H, d.t, J$_1$12, J$_2$6), 2.61 (2H, bs), 2.70 (2H, bs), 3.24 (1.5H, bs), 3.40 (1.5H, bs), 4.08 (2H, t, J6), 8.10 (1H, bs)

Compound 21
Appearance: pasty solid
Melting Point: 52° C.
NMR Spectrum: (300 MHz) $\delta$ (CDCl$_3$): 0.90 (6H, t, J6), 1.30 (56H, bs), 1.61 (2H, t, J6), 1.99 (2H, d.d, J$_1$12, J$_2$6), 2.10 (1H, m), 2.32 (1H, m), 2.51 (1H, m), 2.73 (1H, m), 3.00 (1H, bs), 3.23 (1.5H, bs), 3.42 (1.5H, bs), 4.03 (2H, t, J6), 5.30 (1H, m), 5.50 (1H, d.t, J$_1$16, J$_2$6), 8.12 (1H, bs)

Compound 22
Appearance: white crystal
Melting Point: 68° C.
NMR Spectrum: (300 MHz) $\delta$ (CDCl$_3$): 0.89 (6H, t, J6), 1.27 (56H, bs), 1.62 (2H, t, J6), 1.98 (2H, d.d, J$_1$12, J$_2$6), 2.32 (3H, m), 2.69 (1H, m), 3.01 (1H, bs), 3.21 (1.5H, bs), 3.34 (1.5H, bs), 4.08 (2H, m), 5.30 (1H, d.t, J$_1$16, J$_2$6), 5.49 (1H, d.t, J$_1$16, J$_2$6), 8.10 (1H, bs)

Compound 27
Appearance: pasty solid
Melting Point: 47° C.
NMR Spectrum: (300 MHz) $\delta$ (CDCl$_3$): 0.90 (6H, t, J6), 1.30 (54H, bs), 1.61 (2H, t, J6), 1.99 (2H, d.d, J$_1$12, J$_2$6), 2.10 (1H, m), 2.32 (1H, m), 2.51 (1H, m), 2.73 (1H, m), 3.00 (1H, bs), 3.23 (1.5H, bs), 3.42 (1.5H, bs), 4.03 (2H, t, J6), 5.30 (1H, m), 5.50 (1H, d.t, J$_1$16, J$_2$6), 8.12 (1H, bs)

Compound 28
Appearance: white crystal
Melting Point: 65° C.
NMR Spectrum: (300 MHz) $\delta$ (CDCl$_3$): 0.90 (6H, t, J6), 1.30 (54H, bs), 1.61 (2H, t, J6), 1.99 (2H, d.d, J$_1$12, J$_2$6), 2.10 (1H, m), 2.32 (1H, m), 2.51 (1H, m), 2.73 (1H, m), 3.00 (1H, bs), 3.23 (1.5H, bs), 3.42 (1.5H, bs), 4.03 (2H, t, J6), 5.30 (1H, m), 5.50 (1H, d.t, J$_1$16, J$_2$6), 8.12 (1H, bs)

Structures of other compounds were also confirmed by NMR spectrum or mass spectrum.

Compounds 14, 16, 17, 18, 19, 20, 23, 24, 25, 26, 27 and 34 were oily products.

The addition amount of the compound of the present invention is not particularly limited, but when added to a light-sensitive silver halide emulsion layer, the amount is preferably from $1.0\times10^{-4}$ to $1.0\times10^{-1}$ mol, more preferably from $1.0\times10^{-3}$ to $5.0\times10^{-2}$ mol, per mol of Ag in the same layer. When the compound is added to a light-insensitive layer, preferably from $1\times10^{-6}$ to $3\times10^{-4}$ mol/m$^2$, more preferably from $1\times10^{-5}$ to $1\times10^{-4}$ mol/m$^2$.

The compound of the present invention may be dissolved in a water-soluble solvent (e.g., methanol, ethanol, acetone) and added, may be added in the form of an emulsified dispersion with couplers and the like, or may be added at the time of the preparation of the emulsion, but the addition in the form of an emulsified dispersion is most preferred.

There is no particular limitation on the layers to which the compound of the present invention is added but the compound is preferably added to a silver halide emulsion layer, and is more preferably added to a red-sensitive layer and/or a green-sensitive layer.

The present invention can be applied to various color photographic materials such as color negative films for general photographing use and movie, color reversal films for slide and TV, color papers, color positive films and color reversal papers. Further, the present invention is best suited for the film unit with lense disclosed in JP-B-2-32615 and JP-B-U-3-39784 (the term "JP-B-U" as used herein means an "examined Japanese utility model publication"). Further, the present invention can be applied to heat-developable diffusion transfer process color photographic materials, diffusion transfer photographic materials using autopositive emulsions, and wet process color reversal copy materials using autopositive emulsions. Still further, the present invention can be applied to black-and-white photographic materials such as black-and-white negative films, microfilms and X-ray films. Preferably, the present invention is applied to general color and black-and-white photographic materials for photographing.

When the present invention is applied to a color photographic material, the material can comprise at least one light-sensitive layer on a support. In a typical embodiment, the silver halide photographic material of the present invention comprises at least one light-sensitive layer consisting of a plurality of silver halide emulsion layers having substantially the same color sensitivity but different degrees of sensitivity on a support. The light-sensitive layer is a unit light-sensitive layer having a color sensitivity to any of blue light, green light and red light. In the multilayer silver halide color photographic material, these unit light-sensitive layers are generally arranged in the order of red-sensitive layer, green-sensitive layer and blue-sensitive layer from the support side. However, the order of arrangement can be reversed depending on the purpose, alternatively, the light-sensitive layers may be arranged in such a way that a layer having a different color sensitivity is interposed between layers having the same color sensitivity. Light-insensitive layers may be provided between the above described silver halide light-sensitive layers, and on the uppermost layer and beneath the lowermost layer of the silver halide light-sensitive layers. These light-insensitive layers can contain couplers, DIR compounds and color mixing preventives described below.

They may also contain compounds having the property of releasing a dye imagewise or inverted imagewise and producing difference of diffusability between the released dye and the compound before releasing. As the plurality of silver halide emulsion layers constituting each unit light-sensitive layer, a two-layer structure of a high sensitivity emulsion layer and a low sensitivity emulsion layer can be preferably used as disclosed in German Patent 1,121,470 and British Patent 923,045. It is usually preferred that the emulsion layers are arranged so as to decrease in sensitivity toward a support in this order. Further, a low sensitivity emulsion layer may be provided farther from the support and a high sensitivity emulsion layer may be provided nearer to the support as disclosed in JP-A-57-112751, JP-A-62-200350, JP-A-62-206541, and JP-A-62-206543.

In one specific example, a low sensitivity blue-sensitive layer (BL)/a high sensitivity blue-sensitive layer (BH)/a high sensitivity green-sensitive layer (GH)/a low sensitivity green-sensitive layer (GL)/a high sensitivity red-sensitive layer (RH)/a low sensitivity red-sensitive layer (RL), or BH/BL/GL/GH/RH/RL, or BH/BL/GH/GL/RL/RH can be arranged in this order from the side farthest from the support.

A blue-sensitive layer/GH/RH/GL/RL can be arranged in this order from the side farthest from the support as. disclosed in JP-B-55-34932 (the term "JP-B" as used herein means an "examined Japanese patent publication"). Further, a blue-sensitive layer/GL/RL/GH/RH can be arranged in this order from the side farthest from the support as disclosed in JP-A-56-25738 and JP-A-62-63936.

Further, useful arrangements include the arrangement in which there are three layers having different degrees of sensitivities with the sensitivity being lower towards the support such that the uppermost layer is a silver halide emulsion layer having the highest sensitivity, the middle layer is a silver halide emulsion layer having a lower sensitivity than that of the uppermost layer, and the lowermost layer is a silver halide emulsion layer having a lower sensitivity than that of the middle layer, as disclosed in JP-B-49-15495. In the case of the structure of this type comprising three layers having different degrees of sensitivity, the layers in the unit layer of the same color sensitivity may be arranged in the order of a middle sensitivity emulsion layer/a high sensitivity emulsion layer/a low sensitivity emulsion layer, from the side farthest from the support, as disclosed in JP-A-59-202464.

Alternatively, the layers can be arranged in the order of a high sensitivity emulsion layer/a low sensitivity emulsion layer/a middle sensitivity emulsion layer, or a low sensitivity emulsion layer/a middle sensitivity emulsion layer/a high sensitivity emulsion layer.

Moreover, the arrangement may be varied as indicated above in the case where there are four or more layers.

A donor layer (CL) having an interlayer effect and a different spectral sensitivity distribution from a main light-sensitive layer such as BL, GL and RL may preferably be provided adjacent or close to the main light-sensitive layer to improve color reproducibility, as disclosed in U.S. Pat. Nos. 4,663,271, 4,705,744, 4,707,436, JP-A-62-160448 and JP-A-63-89850.

The preferred silver halides for use in the present invention are silver iodobromide, silver iodochloride or silver iodochlorobromide containing about 30 mol % or less of silver iodide, and particularly preferably silver iodobromide or silver iodochlorobromide containing from about 2 mol % to about 10 mol % of silver iodide.

The silver halide grains in the photographic emulsion may have a regular crystal form such as a cubic, octahedral or tetradecahedral form, an irregular crystal form such as a spherical or plate form, a form which has crystal defects such as twin crystal planes, or a form which is a composite of these forms.

The silver halide grains may be a fine grain having a grain size of about 0.2 μm or less, or a large grain size having a projected area diameter of up to about 10 μm, and the emulsion may be a polydisperse emulsion or a monodisperse emulsion.

The silver halide photographic emulsions for use in the present invention can be prepared using the methods disclosed, for example, in *Research Disclosure* (hereinafter abbreviated to *RD*), No. 17643 (December, 1978), pages 22 and 23, "I. Emulsion Preparation and Types", *RD*, No. 18716 (November, 1979), page 648, *RD*, No. 307105 (November, 1989), pages 863 to 865, P. Glafkides, *Chimie et Physique Photographique*, Paul Montel (1967), G. F. Duffin, *Photographic Emulsion Chemistry*, Focal Press (1966), and V. L. Zelikman, et al., *Making and Coating Photographic Emulsion*, Focal Press (1964).

The monodisperse emulsions disclosed in U.S. Pat. Nos. 3,574,628, 3,655,394 and British Patent 1,413,748 are also preferred.

Further, tabular grains having an aspect ratio of about 3 or more can be used in the present invention. Tabular grains can be easily prepared according to the methods disclosed, for example, in Gutoff, *Photographic Science and Engineering*, Vol. 14, pages 248 to 257 (1970), U.S. Pat. Nos. 4,434,226, 4,414,310, 4,433,048, 4,439,520 and British Patent 2,112, 157.

The crystal structure may be uniform, or the interior and exterior parts of the grains may comprise different halogen compositions, or the grains may have a layered structure. Silver halides which have different compositions may be joined with an epitaxial junction or may be joined with compounds other than a silver halide, such as silver thiocyanate or lead oxide. Further, mixtures of grains which have various crystal forms may also be used.

The above described emulsions may be of the surface latent image type wherein the latent image is primarily formed on the surfaces or of the internal latent image type wherein the latent image is formed within the grains, or of a type wherein the latent image is formed both at the surface and within the grains, but a negative type emulsion is essential. Of the internal latent image types, the emulsion may be a core/shell type internal latent image type emulsion as disclosed in JP-A-63-264740, and a method for preparation of such a core/shell type internal latent image type emulsion is disclosed in JP-A-59-133542. The thickness of the shell of this emulsion varies depending on the development process and the like, but is preferably from 3 to 40 nm, and particularly preferably from 5 to 20 nm.

The silver halide emulsion for use in the present invention is generally subjected to physical ripening, chemical ripening and spectral sensitization. Additives for use in such processes are disclosed in *RD*, No. 17643, *RD*, No. 18716, and *RD*, No. 307105, and the locations of these disclosures are summarized in a table below.

Two or more different types of emulsions which are different in terms of at least one of the characteristics of grain size, grain size distribution, halogen composition, the form of the grains and the sensitivity of the light-sensitive silver halide emulsion can be used in admixture in the same layer in the photographic material of the present invention.

It is preferred to use the silver halide grains having a fogged grain surface as disclosed in U.S. Pat. No. 4,082,553, the silver halide grains having a fogged grain interior as disclosed in U.S. Pat. No. 4,626,498 and JP-A-59-214852, or colloidal silver in light-sensitive silver halide emulsion layers and/or substantially light-insensitive hydrophilic colloid layers. Silver halide grains having a fogged grain interior or surface are silver halide grains which can be developed uniformly (not imagewise) irrespective of whether these grains are present in an unexposed part or an exposed part of the photographic material, and methods for the preparation of such grains are disclosed in U.S. Pat. No. 4,626,498 and JP-A-59-214852. The silver halide which forms the internal nuclei of a core/shell type silver halide grains having a fogged grain interior may have different halogen compositions. The silver halide having a fogged grain interior or surface may be any of silver chloride, silver chlorobromide, silver iodobromide, or silver chloroiodobromide. The average grain size of these fogged silver halide grains is preferably from 0.01 to 0.75 µm, and particularly preferably from 0.05 to 0.6 µm. Further, the form of the grains may be regular grains and may be a polydisperse emulsion, but a monodisperse emulsion (at least 95% of which have a grain size within ±40% of the average grain size in terms of the weight or number of silver halide grains) is preferred.

The use of light-insensitive fine grained silver halides is preferred in the present invention. Light-insensitive fine grained silver halides are fine grained silver halides which are not sensitive to light upon imagewise exposure for obtaining color images and which do not substantially undergo development during development process, and they are preferably not pre-fogged. The fine grained silver halide has a silver bromide content of from 0% to 100 mol %, and may contain silver chloride and/or silver iodide, if necessary. The fine grained silver halides which have a silver iodide content of from 0.5 to 10 mol % are preferred. The average grain size of the fine grained silver halides (the average value of the diameters of the circles corresponding to the projected areas) is preferably from 0.01 to 0.5 µm, and more preferably from 0.02 to 0.2 µm.

The fine grained silver halide can be prepared by the same methods as generally used for the preparation of light-sensitive silver halides. In the preparation of the fine grained silver halide, the surface of the silver halide grains does not need to be optically sensitized and also there is no need for spectral sensitization. However, it is preferred to previously incorporate known stabilizers such as triazole based, azaindene based, benzothiazolium based, or mercapto based compounds, or zinc compounds in the fine grained silver halide before addition to the coating solution. Colloidal silver can be included in the layer containing the fine grained silver halide grains.

The coating weight of silver in the photographic material of the present invention is preferably 6.0 g/m$^2$ or less, and most preferably 4.5 g/m$^2$ or less.

Photographic additives which can be used in the present invention are disclosed in *RD* and the locations related thereto are indicated in the table below.

| Type of Additives | RD 17643 | RD 18716 | RD 307105 |
|---|---|---|---|
| 1. Chemical Sensitizers | page 23 | page 648, right column | page 866 |
| 2. Sensitivity Increasing Agents | — | page 648, right column | — |
| 3. Spectral Sensitizers and Supersensitizers | pages 23–24 | page 648, right column to page 649, right column | pages 866–868 |
| 4. Brightening Agents | page 24 | page 647, right column | page 868 |
| 5. Light Absorbing Agents, Filter Dyes, and Ultraviolet Absorbing Agents | pages 25–26 | page 649, right column to page 650, left column | page 873 |
| 6. Binders | page 26 | page 651, left column | pages 873–874 |
| 7. Plasticizers and Lubricants | page 27 | page 650, right column | page 876 |

| Type of Additives | RD 17643 | RD 18716 | RD 307105 |
|---|---|---|---|
| 8. Coating Aids and Surfactants | pages 26–27 | page 650, right column | pages 875–876 |
| 9. Antistatic Agents | page 27 | page 650, right column | pages 876–877 |
| 10. Matting Agents | — | — | pages 878–879 |

Various dye-forming couplers can be used in the present invention, and the following couplers are particularly preferred.

Yellow Couplers:

The couplers represented by formulae (I) and (II) disclosed in EP 502424A; the couplers represented by formulae (1) and (2) disclosed in EP 513496A (particularly Coupler Y-28, page 18); the couplers represented by formula (I) disclosed in claim 1 of Japanese Patent Application No. 4-134523; the couplers represented by formula (I), lines 45 to 55, column 1 of U.S. Pat. No. 5,066,576; the couplers represented by formula (I), column 0008 of JP-A-4-274425; the couplers disclosed in claim 1 on page 40 of EP 498381A1 (particularly D-35, page 18); the couplers represented by formula (Y) on page 4 of EP 447969A1 (particularly Y-1 (page 17) and Y-54 (page 41)); and the couplers represented by formulae (II) to (IV), lines 36 to 58, column 7 of U.S. Pat. No. 4,476,219 (particularly II-17 and II-19 (column 17), and II-24 (column 19)).

Magenta Couplers:

L-57 (page 11, right lower column), L-68 (page 12, right lower column), and L-77 (page 13, right lower column) disclosed in JP-A-3-39737; [A-4]-63 (page 134), and [A-4]-73 and [A-4]-75 (page 139) disclosed in EP 456257; M-4 and M-6 (page 26) and M-7 (page 27) disclosed in EP 486965; M-45, column 0024 of Japanese Patent Application No. 4-234120; M-1, column 0036 of Japanese Patent Application No. 4-36917; and M-22, column 0237 of JP-A-4-362631.

Cyan Couplers:

CX-1, -3, -4, -5, -11, -12, -14 and -15 (pages 14 to 16) disclosed in JP-A-4-204843; C-7 and C-10 (page 35), C-34 and C-35 (page 37), (I-1) and (I-17) (pages 42 and 43) disclosed in JP-A-4-43345; and the couplers represented by formula (Ia) or (Ib) disclosed in claim 1 of Japanese Patent Application No. 4-236333.

Polymer Couplers:

P-1 and P-5 (page 11) disclosed in JP-A-2-44345.

The couplers disclosed in U.S. Pat. No. 4,366,237, British Patent 2,125,570, EP 96873B and German Patent 3,234,533 are preferred as couplers the colored dyes of which have an appropriate diffusibility.

Preferred couplers for correcting the unnecessary absorption of colored dyes include the yellow colored cyan couplers represented by formulae (CI), (CII), (CIII) and (CIV) disclosed on page 5 of EP 456257A1 (particularly YC-86, page 84); the yellow colored magenta couplers ExM-7 (page 202), EX-1 (page 249), and EX-7 (page 251) disclosed in EP 456257A1; the magenta colored cyan couplers CC-9 (column 8) and CC-13 (column 10) disclosed in U.S. Pat. No. 4,833,069; the coupler (2) (column 8) disclosed in U.S. Pat. No. 4,837,136; and the colorless masking couplers represented by formula (A) disclosed in claim 1 of WO 92/11575 (particularly the compounds on pages 36 to 45).

Examples of compounds (including couplers) which release photographically useful residual groups of compounds upon reacting with the oxidation product of a developing agent include the following: development inhibitor releasing compounds: the compounds represented by formulae (I), (II), (III) and (IV) disclosed on page 11 of EP 378236A1 (particularly T-101 (page 30), T-104 (page 31), T-113 (page 36), T-131 (page 45), T-144 (page 51) and T-158 (page 58)), the compounds represented by formula (I) disclosed on page 7 of EP 436938A2 (particularly D-49 (page 51)), the compounds represented by formula (1) disclosed in Japanese Patent Application No. 4-134523 (particularly (23), column 0027), and the compounds represented by formulae (I), (II) and (III) disclosed on pages 5 and 6 of EP 440195A2 (particularly I-(1), page 29); bleaching accelerator releasing compounds: the compounds represented by formulae (I) and (I') disclosed on page 5 of EP 310125A2 (particularly (60) and (61), page 61), and the compounds represented by formula (I) disclosed in claim 1 of Japanese Patent Application No. 4-325564 (particularly (7), column 0022); ligand releasing compounds: the compounds represented by LIG-X disclosed in claim 1 of U.S. Pat. No. 4,555,478 (particularly the compounds in lines 21 to 41, column 12); leuco dye releasing compounds: compounds 1 to 6, columns 3 to 8 of U.S. Pat. No. 4,749,641; fluorescent dye releasing compounds: the compounds represented by COUP-DYE disclosed in claim 1 of U.S. Pat. No. 4,774,181 (particularly Compounds 1 to 11, columns 7 to 10); development accelerator or fogging agent releasing compounds: the compounds represented by formulae (1), (2) and (3) disclosed in U.S. Pat. No. 4,656,123 (particularly (I-22), column 25), and ExZK-2, lines 36 to 38, page 75 of EP 450637A2; and compounds which release dyes the color of which is restored after being released: the compounds represented by formula (I) disclosed in claim 1 of U.S. Pat. No. 4,857,447 (particularly Y-1 to Y-19, columns 25 to 36).

Preferred additives other than couplers are listed below.

Dispersion mediums of oil-soluble organic compound: P-3, -5, -16, -19, -25, -30, -42, -49, -54, -55, -66, -81, -85, -86 and -93 (pages 140 to 144) of JP-A-62-215272; latexes for impregnation of oil-soluble organic compound: the latexes disclosed in U.S. Pat. No. 4,199,363; scavengers for the oxidation product of a developing agent: the compounds represented by formula (I), lines 54 to 62, column 2 of U.S. Pat. No. 4,978,606 (particularly I-(1), -(2), -(6) and -(12) (columns 4 and 5)), and the compounds represented by the formulae disclosed in lines 5 to 10, column 2 of U.S. Pat. No. 4,923,787 (particularly compound 1 (column 3)); stain inhibitors: the compounds represented by formulae (I) to (III), lines 30 to 33, page 4 of EP 298321A (particularly I-47, -72, III-1, -27 (pages 24 to 48)); discoloration inhibitors: A-6, -7, -20, -21, -23, -24, -25, -26, -30, -37, -40, -42, -48, -63, -90, -92, -94 and -164 (pages 69 to 118) disclosed in EP 298321A, II-1 to III-23, columns 25 to 38 of U.S. Pat. No. 5,122,444 (particularly III-10), I-1 to III-4, pages 8 to 12 of EP 471347A (particularly II-2), and A-1 to -48, columns 32 to 40 of U.S. Pat. No. 5,139,931 (particularly A-39 and -42); compounds for reducing the using amount of supersensitizers or color mixing preventives: I-1 to II-15, pages 5 to 24 of EP 411324A (particularly I-46); formalin scavengers: SCV-1 to -28, pages 24 to 29 of EP 477932A (particularly SCV-8); hardening agents: H-1, -4, -6, -8 and -14 on page 17 of JP-A-1-214845, the compounds represented by formulae (VII) to (XII) (H-1 to -54), columns 13 to 23 of U.S. Pat. No. 4,618,573, the compounds represented by formula (6), right lower column, page 8 of JP-A-2-214852 (H-1 to -76) (particularly H-14), and the compounds disclosed in claim 1 of U.S. Pat. No. 3,325,287; development inhibitor precursors: P-24, -37 and -39, pages 6 and 7 of JP-A-62-168139, the compounds disclosed in claim 1 of U.S. Pat. No. 5,019,492 (particularly compounds 28 and 29, column 7); biocides and fungicides: I-1 to III-43, columns 3 to 15 of U.S. Pat. No. 4,923,790 (particularly compounds II-1, -9, -10, -18 and III-25); stabilizers and antifoggants: I-1 to (14), columns 6 to 16 of U.S. Pat. No. 4,923,793 (particularly I-1, -60, (2), and (13)), and compounds 1 to 65, columns 25 to 32 of U.S. Pat. No. 4,952,483 (particularly compound 36); chemical sensitizers: triphenylphosphine selenide, and compound 50 disclosed in JP-A-5-40324; dyes: a-1 to b-20, pages 15 to 18 (particularly a-1, -12, -18, -27, -35, -36, and b-5), V-1 to -23, pages 27 to 29 (particularly V-1) of JP-A-3-156450, F-I-1 to F-II-43, pages 33 to 55 of EP 445627A (particularly F-I-11 and F-II-8), III-1 to -36, pages 17 to 28 of EP 457153A (particularly III-1 and -3), crystallite dispersions of Dye-1 to -124, pages 8 to 26 of WO 88/04794, compounds 1 to 22, pages 6 to 11 of EP 319999A (particularly compound 1), compounds D-1 to -87 represented by formulae (1) to (3), pages 3 to 28 of EP 519306A, compounds 1 to 22 represented by formula (I), columns 3 to 10 of U.S. Pat. No. 4,268,622, and compounds (1) to (31) represented by formula (I), columns 2 to 9 of U.S. Pat. No. 4,923,788; ultraviolet absorbing agents: compounds (18b) to (18r) represented by formula (1), 101 to 427, pages 6 to 9 of JP-A-46-3335, compounds (3) to (66) represented by formula (I), pages 10 to 44, and compounds HBT-1 to -10 represented by formula (III), page 14 of EP 520938A, and compounds (1) to (31) represented by formula (1), columns 2 to 9 of EP 521823A.

Suitable supports which can be used in the present invention are disclosed, for example, in RD, No. 17643, page 28, RD, No. 18716, from Page 647, right column to page 648, left column, and RD, No. 307105, page 879.

The photographic material of the present invention has a total film thickness of all the hydrophilic colloid layers on the side where the silver halide emulsion layers are located of preferably 28 µm or less, more preferably 23 µm or less, still more preferably 18 µm or less, and most preferably 16 µm or less. Further, the film swelling rate $T_{1/2}$ is preferably 30 seconds or less, and more preferably 20 seconds or less. $T_{1/2}$ is defined as the time taken to reach ½ of the saturated film thickness, taking 90% of the maximum swollen film thickness reached when being processed in a color developing solution at 30° C. for 3 minutes and 15 seconds as the saturated film thickness. The film thickness means the film thickness measured under conditions of 25° C., 55% relative humidity (stored for 2 days), and $T_{1/2}$ can be measured using a swellometer of the type described in A. Green, et al., Photogr. Sci. Eng., Vol. 19, No. 2, pages 124 to 129. $T_{1/2}$ can be adjusted by adding hardening agents to gelatin which is used as a binder, or by changing the aging conditions after coating. Further, a swelling factor of from 150% to 400% is preferred. The swelling factor can be calculated from the maximum swollen film thickness obtained under the conditions described above using the equation: (maximum swollen film thickness–film thickness)/film thickness.

The provision of hydrophilic colloid layers (known as backing layers) having a total dry film thickness of from 2 µm to 20 µm on the side of the support opposite to the side on which emulsion layers are provided is preferred in the photographic material of the present invention. The inclusion of the above described light absorbing agents, filter dyes, ultraviolet absorbing agents, antistatic agents, hardening agents, binders, plasticizers, lubricants, coating aids, and surfactants in the backing layers is preferred. The swelling factor of the backing layer is preferably from 150 to 500%.

The photographic material of the present invention can be development processed by the general methods disclosed in RD, No. 17643, pages 28 and 29, RD, No. 18716, page 651, from left column to right column, and RD, No. 307105, pages 880 and 881.

The color developing solution for use in the development processing of the photographic material of the present invention is preferably an alkaline aqueous solution which contains an aromatic primary amine developing agent as a main component. Aminophenol based compounds are useful as a color developing agent, but the use of p-phenylenediamine based compounds is preferred, and representative examples thereof include the compounds disclosed in lines 43 to 52, page 28 of EP 556700A. Two or more of these compounds can be used in combination according to purposes.

The color developing solution generally contains a pH buffer such as alkali metal carbonate, borate or phosphate, or a development inhibitor or an antifoggant such as chloride, bromide, iodide, benzimidazoles, benzothiazoles, or mercapto compounds. The color developing solution may also contain, if necessary, various preservatives such as hydroxylamine, diethylhydroxylamine, sulfite, hydrazines, e.g., N,N-biscarboxymethylhydrazine, phenylsemicarbazides, triethanolamine and catecholsulfonic acids, an organic solvent such as ethylene glycol and diethylene glycol, a development accelerator such as benzyl alcohol, polyethylene glycol, quaternary ammonium salt, and amines, a dye-forming coupler, a competitive coupler, an auxiliary developing agent such as 1-phenyl-3-pyrazolidone, a thickener, and various chelating agents typified by aminopolycarboxylic acid, aminopolyphosphonic acid, alkylphosphonic acid, and phosphonocarboxylic acid, e.g., ethylenediaminetetraacetic acid, nitrilotriacetic acid, diethylenetriaminepentaacetic acid, cyclohexanediaminetetraacetic acid, hydroxyethyliminodiacetic acid, 1-hydroxyethylidene-1,1-diphosphonic acid, nitrilo-N,N,N-trimethylenephosphonic acid, ethylenediamine-N,N,N,N-tetramethylenephosphonic acid, ethylenediamine-di(o-hydroxyphenylacetic acid) and salts of these acids.

Further, the color development is generally carried out after the black-and-white development in the case of reversal processing. Known black-and-white developing agents such as hydroxybenzenes, e.g., hydroquinone, 3-pyrazolidones, e.g., 1-phenyl-3-pyrazolidone, or aminophenols, e.g., N-methyl-p-aminophenol can be used alone or in combination in the black-and-white developing solution. The pH of these color developing solution and black-and-white developing solution is generally from 9 to 12. The replenishment rate of these developing solutions depends on the color photographic material to be processed but, in general, it is 3 liters or less per square meter of the photographic material, and can be reduced to 500 ml or less by reducing the bromide ion concentration in the replenisher. When the replenishment rate is reduced, it is preferred to prevent evaporation and air oxidation of the solution by minimizing the area of contact of the solution with the air in the processing tank.

The processing effect by the contact of the photographic processing solution with the air in a processing tank can be evaluated by the following equation: Open factor=[Contact area of processing solution with air $(cm^2)$]÷ [Volume of processing solution $(cm^3)$]. This open factor is preferably 0.1 or less, and more preferably from 0.001 to 0.05. The method using a movable lid as disclosed in JP-A-1-82033 and the slit development processing method as disclosed in JP-A-63-216050 can be used as means of reducing the open factor, as well as the provision of a shielding material such as a floating lid on the surface of the photographic processing solution in the processing tank. Reduction of the open factor is preferred not only in the processes of the color development and the black-and-white development but also in all the subsequent processes such as the bleaching process, the bleach-fixing process, the fixing process, the washing process and the stabilizing process. Further, the replenishment rate can be reduced by suppressing the accumulation of the bromide ion in the developing solution.

The color development processing time is usually set between 2 and 5 minutes, but shorter processing time can be used by raising the temperature and the pH and increasing the concentration of the color developing agent.

The photographic emulsion layer is generally subjected to a bleaching process after color development. A bleaching process may be carried out simultaneously with a fixing process (a bleach-fixing process) or may be carried out separately. In addition, a bleach-fixing process can be carried out after a bleaching process to speed up the processing. Moreover, the processing can be carried out in two connected bleach-fixing baths, a fixing process can be carried out before a bleach-fixing process, or a bleaching process can be carried out after a bleach-fixing process, as required. Compounds of multivalent metals such as iron(III), peracids, quinones, and nitro compounds can be used as a bleaching agent. Representative bleaching agents include organic complex salts of iron(III) with aminopolycarboxylic acids, e.g., ethylenediaminetetraacetic acid, diethylenetriaminepentaacetic acid, cyclohexanediaminetetraacetic acid, methyliminodiacetic acid, 1,3-diaminopropanetetraacetic acid, and glycol ether diaminetetraacetic acid, or citric acid, tartaric acid or malic acid. The use of aminopolycarboxylic acid iron(III) complex salts, in particular, ethylenediaminetetraacetic acid iron(III) complex salts and 1,3-diaminopropanetetraacetic acid iron(III) complex salts, is preferred for providing rapid processing and preventing environmental pollution. Further, aminopolycarboxylic acid iron(III) complex salts are particularly useful in both of a bleaching solution and a bleach-fixing solution. The pH of the bleaching solution or the bleach-fixing solution in which these aminopolycarboxylic acid iron(III) complex salts are used is generally from 4.0 to 8, but lower pH values can be used to speed up the processing.

Bleaching accelerators can be used, if necessary, in the bleaching solution, the bleach-fixing solution, or the prebaths thereof. Specific examples of useful bleaching accelerators are disclosed in the following publications: for example, there are the compounds which have a mercapto group or a disulfide group disclosed in U.S. Pat. No. 3,893,858, German Patents 1,290,812, 2,059,988, JP-A-53-32736, JP-A-53-57831, JP-A-53-37418, JP-A-53-72623, JP-A-53-95630, JP-A-53-95631, JP-A-53-104232, JP-A-53-124424, JP-A-53-141623, JP-A-53-28426, and RD, No. 17129 (July, 1978); the thiazolidine derivatives disclosed in JP-A-50-140129; the thiourea derivatives disclosed in JP-B-45-8506, JP-A-52-20832, JP-A-53-32735, and U.S. Pat. No. 3,706,561; the iodides disclosed in German Patent 1,127,715 and JP-A-58-16235; the polyoxyethylene compounds disclosed in German Patents 966,410 and 2,748,430; the polyamine compounds disclosed in JP-B-45-8836; the other compounds disclosed in JP-A-49-40943, JP-A-49-59644, JP-A-53-94927, JP-A-54-35727, JP-A-55-26506 and JP-A-58-163940; and bromide ion. Of these compounds, those which have a mercapto group or a disulfide group are preferred for providing large accelerating effect, and the compounds disclosed in U.S. Pat. No. 3,893,858, German Patent 1,290,812 and JP-A-53-95630 are particularly preferred. Further, the compounds disclosed in U.S. Pat. No. 4,552,834 are also preferred. These bleaching accelerators may be contained in the photographic material. These bleaching accelerators are especially effective for bleach-fixing the color photographic material for photographing.

The inclusion of organic acids as well as the compounds described above in the bleaching solution and the bleach-fixing solution is preferred for preventing the generation of bleach staining. Particularly preferred organic acids are compounds which have an acid dissociation constant (pKa) of from 2 to 5, specifically, acetic acid, propionic acid, and hydroxyacetic acid.

Thiosulfate, thiocyanate, thioether based compounds, thioureas, and large amounts of iodide can be used as the fixing agent which is used in a fixing solution and bleach-fixing solution, but thiosulfate is generally used, in particular, ammonium thiosulfate can be most widely used. Further, the combined use of thiosulfate and thiocyanate, thioether based compounds, thiourea is also preferred. Sulfite, bisulfite, carbonyl-bisulfite addition produces or the sulfinic acid compounds disclosed in EP 294769A are preferred as preservatives for the fixing solution and the bleach-fixing solution. Moreover, the addition of aminopolycarboxylic acids and organic phosphonic acids to the fixing solution and the bleach-fixing solution is preferred for stabilizing these solutions.

The addition of compounds having a pKa of from 6.0 to 9.0, preferably imidazoles such as imidazole, 1-methylimidazole, 1-ethylimidazole and 2-methylimidazole, in an amount of from 0.1 to 10 mol per liter, to the fixing solution or the bleach-fixing solution is preferred for pH control in the present invention.

The total desilvering processing time is preferably shorter within the range not generating desilvering failure. The desilvering processing time is preferably from 1 minute to 3 minutes and more preferably from 1 minute to 2 minutes. Further, the processing temperature is from 25° C. to 50° C., and preferably from 35° C. to 45° C. The desilvering rate is increased and the occurrence of staining after processing is effectively prevented in the preferred temperature range.

Stirring as vigorous as possible in the desilvering process is preferred. Specific examples of methods of forced stirring include the method in which a jet of the processing solution is impinged on the surface of the emulsion of the photographic material as disclosed in JP-A-62-183460, the method in which the stirring effect is raised using a rotating means as disclosed in JP-A-62-183461, the method in which the photographic material is moved with a wiper blade, which is installed in the solution, in contact with the surface of the emulsion, and the generated turbulent flow at the surface of the emulsion increases the stirring effect, and the method in which the circulating flow rate of the entire processing solution is increased. These means for increasing the stirring level are effective for the bleaching solution, the bleach-fixing solution and the fixing solution. It is supposed that the increased stirring level increases the rate of supply of the bleaching agent and the fixing agent to the emulsion film and, as a result, increases the desilvering rate. Further, the above means of increasing stirring are more effective when a bleaching accelerator is used, and it is possible to extremely increase the bleaching accelerating effect and to eliminate the fixing hindrance action due to the bleaching accelerator.

The automatic processors for use in processing the photographic material of the present invention preferably have the means of transporting photographic materials as disclosed in JP-A-60-191257, JP-A-60-191258, and JP-A-60-191259. As described in the above JP-A-60-191257, such a transporting means can greatly reduce the carryover of the processing solution from the previous bath to the next bath and is effective for preventing the deterioration of the properties of the processing solution. These effects are especially effective in reducing the processing time of each process and reducing the replenishment rate of each processing solution.

The photographic material of the present invention is generally subjected to a washing process and/or a stabilizing process after the desilvering process. The amount of washing water in the washing process can be selected from a wide range according to the characteristics and the application of the photographic materials (for example, the materials such as couplers, etc., which are used), the temperature of washing water, the number of washing tanks (the number of washing stages), the replenishing system, that is, whether a countercurrent system or a concurrent system, and other various conditions. Of the foregoing conditions, the relationship between the number of washing tanks and the amount of water in a multistage countercurrent system can be obtained by the method described in *Journal of the Society of Motion Picture and Television Engineers*, Vol. 64, pages 248 to 253 (May, 1955). The amount of the washing water can be greatly reduced according to the multistage countercurrent system of the above literature, however, problems arise such that bacteria proliferate due to the increased residence time of the water in the tanks, and suspended matters produced thereby adhere to the photographic material. The method of reducing the calcium ion and magnesium ion concentrations as disclosed in JP-A-62-288838 can be used as a very effective means for overcoming this problem. Also, the isothiazolone compounds and the thiabendazoles as disclosed in JP-A-57-8542, the chlorine based disinfectants such as chlorinated sodium isocyanurate, the benzotriazole, and the disinfectants disclosed in Hiroshi Horiguchi, *Bobkin Bohbai no Kagaku (The Chemistry of Biocides and Fungicides*, published by Sankyo Shuppan K.K. (1986), *Biseibutsu no Mekkin, Sakkin, Bohbai Gijutsu (Biocidal and Fungicidal Techniques to Microbes)*, edited by Hygiene Technology Society, published by Industrial Technology Society (1982), and *Bohkin Bohbai Zai Jiten (Biocide and Fungicide Thesaurus)*, edited by Japanese Biocide and Fungicide Society (1986), can also be used.

The pH of the washing water in the processing of the photographic material of the present invention is from 4 to 9 and preferably from 5 to 8. The temperature and the time of the washing process can be selected variously according to the characteristics and the end use purpose of the photographic material to be processed, but is generally from 15° C. to 45° C. for 20 seconds to 10 minutes, and preferably from 25° C. to 40° C. for 30 seconds to 5 minutes. Further, the photographic material of the present invention can be processed directly with a stabilizing solution instead of being subjected to a water washing process as described above. Known methods as disclosed in JP-A-57-8543, JP-A-58-14834 and JP-A-60-220345 can be used in such a stabilizing process.

Further, there is also a case in which a stabilizing process is carried out following the above described water washing process, and the stabilizing bath containing a dye stabilizer and a surfactant which is used as a final bath for a photographic material for photographing is one example of such a process. Aldehydes such as formaldehyde and glutaraldehyde, N-methylol compounds, hexamethylenetetramine or an aldehyde-sulfite addition product can be used as a dye stabilizer.

Various chelating agents and fungicides can also be added to such a stabilizing bath.

The overflow generated by the replenishment of the above described washing water and/or stabilizing solution can be reused in other processes such as a desilvering process, etc.

When the above processing solutions are concentrated due to evaporation by the processing using an automatic processor, etc., it is preferred to replenish an appropriate amount of water to correct the concentration.

Color developing agents can be incorporated into a photographic material of the present invention to simplify and speed up the processing. Color developing agent precursors are preferred for the incorporation. For example, the indoaniline based compounds disclosed in U.S. Pat. No. 3,342,597, the Schiff's base type compounds disclosed in U.S. Pat. No. 3,342,599, *Research Disclosure*, Nos. 14850 and 15159, the aldol compounds disclosed in *RD*, No. 13924, the metal complex salts disclosed in U.S. Pat. No. 3,719,492 and the urethane based compounds disclosed in JP-A-53-135628 can be used for this purpose.

Various 1-phenyl-3-pyrazolidones may be included, if required, in the photographic material of the present invention to accelerate color development. Typical compounds are disclosed in JP-A-56-64339, JP-A-57-144547 and JP-A-58-115438.

The various processing solutions of the present invention are used at a temperature of from 10° C. to 50° C. The standard temperature is generally from 33° C. to 38° C., but higher temperatures can be used to accelerate the processing to shorten the processing time, on the contrary, lower temperature can be used to improve the picture quality and stabilization of the processing solutions.

When the present invention is applied to black-and-white photographic materials, the various additives and development processing methods used therefor are not particularly limited, and those disclosed in the following places of JP-A-2-68539, JP-A-5-11389 and JP-A-2-58041 can be preferably used.

1. Silver halide emulsion and the preparation method from 6 lines up from the bottom, right lower column, page 8 to line 12, right upper column, page 10 of JP-A-2-68539
2. Chemical sensitization method from line 13, right upper column, page 10 to line 16, left lower column, page 10 of JP-A-2-68539; selenium sensitization method disclosed in JP-A-5-11389
3. Antifoggant and stabilizer from line 17, left lower column, page 10 to line 7, left upper column, page 11 of JP-A-2-68539; from line 2, left lower column, page 3 to left lower column, page 4 of JP-A-2-68539
4. Spectral sensitizing dye from line 4, right lower column, page 4 to right lower column, page 8 of JP-A-2-68539; from line 8, left lower column, page 12 to line 19, right lower column, page 12 of JP-A-2-58041
5. Surfactant and antistatic agent from line 14, left upper column, page 11 to line 9, left upper column, page 12 of JP-A-2-68539; from line 14, left lower column, page 2 to line 12, page 5 of JP-A-2-58041
6. Matting agent, plasticizer and sliding agent from line 10, left upper column, page 12 to line 10, right upper column, page 12 of JP-A-2-58041; from line 13, left lower column, page 5 to line 3, left lower column, page 10 of JP-A-2-58041
7. Hydrophilic colloid from line 11, right upper column, page 12 to line 16, left lower column, page 12 of JP-A-2-68539
8. Hardening agent from line 17, left lower column, page 12 to line 6, right upper column, page 13 of JP-A-2-68539
9. Development processing method from line 14, left upper column, page 15, to line 13, left lower column, page 15 of JP-A-2-68539.

In addition to the above description, the present invention can be applied to a diffusion transfer photograph, that is, the so-called instant photograph. Examples of this diffusion transfer photographs are disclosed in JP-A-5-297544.

Further, the present invention can be utilized in heat-developable photographic materials. The heat-developable photographic materials to which the present invention can be applied may be those forming black-and-white images or color images, and such heat-developable photographic materials are disclosed, for example, in JP-A-60-162251, JP-A-64-13546, JP-A-1-161236, U.S. Pat. Nos. 4,474,867, 4,478,927, 4,507,380, 4,500,626, 4,483,914, 4,783,396, 4,740,445, JP-A-59-231539 and JP-A-60-2950.

The present invention can also be applied to a wet process color reversal copy material using autopositive emulsions. With respect to this material, Sample No. 101 in Example 1 of JP-A-3-152530 and Sample No. 1 in JP-A-2-90145 can be referred to.

A silver halide photographic material for color diffusion transfer to which the present invention is applicable is described below.

A photographic material for use in the present invention fundamentally comprises a support having thereon light-sensitive silver halide, a binder and a dye-donating compound (sometimes serves also as a reducing agent), etc. These components are in many cases contained in the same layer, but they can be divided and contained in separate layers if they are in states possible to react. For example, when a colored dye-donating compound is contained in a lower layer of a silver halide emulsion, reduction of sensitivity can be prevented.

To obtain a wide range of colors in the chromaticity diagram using three primary colors of yellow, magenta and cyan, at least three silver halide emulsion layers each having sensitivity in different range of spectrum are used in combination. For example, there are a combination of a blue-sensitive layer, a green-sensitive layer and a red-sensitive layer, a combination of a green-sensitive layer, a red-sensitive layer and an infrared-sensitive layer, or a combination of a red-sensitive layer, a first infrared layer and a second infrared layer. Each light-sensitive layer can be arranged in various orders known in usual color light-sensitive materials. Further, each of these light-sensitive layers may be divided two or more layers, if necessary.

A heat-developable photographic material may have various auxiliary layers such as a protective layer, a subbing layer, an interlayer, a yellow filter layer, an antihalation layer and a backing layer.

Fundamental Constitution and Preparation Method of Silver Halide Grains

The silver halide which can be used in the present invention may be any of silver chloride, silver bromide, silver iodobromide, silver chlorobromide, silver iodochloride or silver chloroiodobromide, but preferably silver iodobromide, silver chloride, silver bromide or silver chlorobromide containing 30 mol % or less of silver iodide.

The silver halide emulsion for use in the present invention may be either a surface latent image type or an internal latent image type. An internal latent image type emulsion is used as a direct reversal emulsion by combining a nucleating agent and light-fogging agent. The grains may be the so-called multistructural grains having different structures in the interior and the surface of the grains. Of the multistructural grains, double structural grains are sometimes, in particular, called a core/shell type emulsion.

The silver halide grains for use in the present invention are preferably multistructural grains and more preferably a core/shell type emulsion, but the present invention is not limited thereto.

The silver halide emulsion for use in the present invention is preferably monodisperse emulsion and, as disclosed in JP-A-3-110555, preferably having a variation coefficient of 20% or less, more preferably 16% or less, and still more preferably 10% or less. However, the present invention is not limited to this monodisperse emulsion.

The average grain size of the silver halide grains for use in the present invention is from 0.1 µm to 2.2 µm, preferably from 0.1 µm to 1.2 µm. The crystal habit of the silver halide grains may be any of cubic, octahedral, tabular with high aspect ratio, potato-like form, or any other form, but a cubic emulsion is preferred.

Specifically, any of silver halide emulsions disclosed in U.S. Pat. Nos. 4,500,626, column 50, 4,628,021, *Research Disclosure* (hereinafter abbreviated to RD), No. 17029 (1978) and JP-A-62-25159 can be used in the present invention.

In the process of the preparation of the silver halide emulsion of the present invention, when carrying out desalting processing, that is, excess salt removal, well known noodle washing method in which gelatin is made gelation may be used, or a flocculation method using inorganic salts comprising polyvalent anions, e.g., sodium sulfate, anionic surfactant, anionic polymer (e.g., polystyrenesulfonate), or gelatin derivatives (e.g., aliphatic acylated gelatin, aromatic acylated gelatin, aromatic carbamoylated gelatin) may be used. A flocculation method using a flocculant (a) or a flocculant (b) described below is preferably used, but the present invention is not limited thereto. An ultrafiltration method may be used for this purpose without using the above described flocculants. Further, excess salt removal may be omitted.

The silver halide emulsion for use in the present invention may contain heavy metals such as iridium, rhodium, platinum, cadmium, zinc, thallium, lead, iron or chromium for various purposes. These compounds may be contained alone or two or more of them may be used in combination. The addition amount varies according to the use purpose but generally from $10^{-9}$ to $10^{-3}$ mol per mol of silver halide. Further, they may be contained uniformly in the grain or may be localized on the surface or inside, of the grain.

The amount of iridium for use in the present invention is preferably from $10^{-9}$ to $10^{-4}$ mol, more preferably from $10^{-8}$ to $10^{-6}$ mol, per mol of silver halide. When a core/shell emulsion is used, iridium may be added to core and/or shell. Preferably used iridium compounds are $K_2IrCl_6$ and $K_3IrCl_6$.

The amount of rhodium for use in the present invention is preferably from $10^{-9}$ to $10^{-6}$ mol per mol of silver halide.

The amount of iron for use in the present invention is preferably from $10^{-7}$ to $10^{-3}$ mol, more preferably from $10^{-6}$ to $10^{-3}$ mol, per mol of silver halide.

A method in which a part or the entire of these heavy metals are previously doped to a fine grain emulsion such as silver chloride, silver chlorobromide, silver bromide or silver iodobromide, then this fine grain emulsion is added to the silver halide emulsion so as to be localized at the surface of the silver halide emulsion is preferably used.

In the stage of the formation of the silver halide grains, rhodanide, $NH_3$, tetra-substituted thioether compounds such as later described compounds (a), the organic thioether derivatives disclosed in JP-B-47-11386 and the sulfur-containing compounds disclosed in JP-A-53-144319 can be used as a silver halide solvent.

In the stage of the formation of the silver halide grains, the nitrogen-containing compounds disclosed in JP-B-46-7781, JP-A-60-222842 and JP-A-60-122935 can be used.

Gelatin is preferably used as protective colloid and a binder for other hydrophilic colloid in the preparation of the emulsion of the present invention, but other hydrophilic colloids can also be used. Examples thereof include gelatin derivatives; graft polymers of gelatin and other high polymers; proteins such as albumin and casein; cellulose derivatives such as hydroxyethyl cellulose, and cellulose sulfate; sodium alginate and starch derivatives; and various kinds of synthetic hydrophilic high polymers of homopolymers or copolymers such as polyvinyl alcohol, partially acetalated polyvinyl alcohol, poly-N-vinyl pyrrolidone, polyacrylic acid, polymethacrylic acid, polyacrylamide, polyvinylimidazole, and polyvinylpyrazole.

In addition to lime-processed gelatin, acid-processed gelatin and the enzyme-processed gelatin disclosed in *Bull. Soc. Sci. Phot., Japan*, No. 16, page 30 (1966) can be used, and hydrolyzed product and enzyme decomposed product of gelatin can also be used.

With respect to other conditions, descriptions in P. Glafkides, *Chimie et Physique Photographique*, Paul Montel (1967), G. F. Duffin, *Photographic Emulsion Chemistry*, The Focal Press (1966), V. L. Zelikman, et al., *Making and Coating Photographic Emulsion*, The Focal Press (1964), can be referred to. That is, any process, such as an acid process, a neutral process, and an ammoniacal process, can be used. Any of a single jet method, a double jet method, and a combination of these methods can be used for reacting a soluble silver salt with a soluble halide.

Further, the so-called reverse mixing method in which silver halide grains are formed in the presence of excess silver ion can also be employed. The so-called controlled double jet method, which is one form of a double jet method, in which the pAg of the liquid phase in which the silver halide is formed is maintained constant can also be used.

Moreover, to accelerate the grain growth, the addition concentration, the addition amount and the addition rate of the silver salt and halide to be added may be increased (JP-A-55-142329, JP-A-55-158124 and U.S. Pat. No. 3,650, 757).

During or after grain formation, the surface of the silver halide grain may be substituted with halide for forming hardly soluble silver halide grains.

Any known stirring method may be used for stirring the reaction solution. Further, the temperature and pH of the reaction solution during silver halide formation may be set as desired. Preferred pH is from 2.2 to 6.0 and more preferably from 3.0 to 5.5.

The emulsion for blue-sensitive layer for use in the present invention is disclosed in Japanese Patent Application No. 3-308225. The silver halide emulsion comprising silver halide grains having high silver iodide content layer at the grain surface and chemical sensitized before desalting and addition of iodine ion is particularly preferred for blue-sensitive layer.

Addition Method of Sensitizing Dye

A sensitizing dye can be added at any time fundamentally. That is, a sensitizing dye may be added at the initial stage of the silver halide grain formation (it may be added before nucleus formation), during or after the formation, or at the initial stage, during or after the desalting processing, at the time of redispersion of gelatin, before, during or after chemical sensitization, or at the time of preparation of the coating solution. Preferably, a sensitizing dye is added during or after completion of the silver halide grain formation or before, during or after chemical sensitization. After chemical sensitization means that a sensitizing dye is added after all the chemicals necessary for chemical sensitization have been added.

As disclosed in U.S. Pat. No. 4,183,756, a sensitizing dye may be present in the reaction system of a soluble silver salt (e.g., silver nitrate) and a soluble halide (e.g., potassium bromide) before a silver halide grain is generated, or as disclosed in U.S. Pat. No. 4,225,666 a sensitizing dye may be present in the above described reaction system after the nucleus formation of a silver halide grain and before termination of the process of the silver halide grain formation. Further, a sensitizing dye may be present in the reaction solution simultaneously with the silver halide grain formation, that is, at the time of mixing the above described silver salt and halide. The photographic material containing the thus-prepared emulsion is excellent in storage stability under high temperature and is superior in gradation.

The concentration of the solution to be added, solvent, the time of addition (all the amount may be added at one time or may be divided to several parts and added), temperature, pH, etc., are not limited. Further, the way of addition may be level addition or submerged addition. These conditions are disclosed in detail in JP-A-3-110555.

Kind of Sensitizing Dye

The emulsion for use in the present invention contains a sensitizing dye such as a cyanine dye, a merocyanine dye, a complex cyanine dye, a complex merocyanine dye, a holopolar cyanine dye, a hemicyanine dye, a styryl dye, and a hemioxonol dye.

Specific examples of sensitizing dyes are disclosed in U.S. Pat. No. 4,617,257, JP-A-59-180550, JP-A-60-140335 and U.S. Pat. No. Re. 17029 (1978), pages 12 and 13.

These sensitizing dyes may be used alone or may be used in combination. A combination of a sensitizing dye is often used for the purpose of supersensitization.

In combination with these sensitizing dyes, dyes which themselves do not have a spectral sensitizing function or compounds substantially do not absorb visible light but exhibit a supersensitizing effect may be contained in the emulsion (for example, those disclosed in U.S. Pat. No. 3,615,641 and JP-A-63-23145).

In any addition method of sensitizing dyes, all addition amount of the sensitizing dye may be added at one time or may be added dividing to several parts. Further, the sensitizing dye may be added in admixture with the soluble silver salt and/or halide.

The sensitizing dyes may be added to the emulsion by dissolving in an organic solvent such as methanol, ethanol, propanol, fluorinated alcohol, methyl cellosolve, dimethylformamide or acetone, or water (which may be alkaline or acidic), two or more of the above organic solvents may be used in combination. The sensitizing dyes may be incorporated into the emulsion by dispersion in water/gelatin dispersion system or may be added in the form of frozen dried powder. Further, they may be added in the form of dispersed powder or solution using a surfactant.

The sensitizing dyes disclosed, for example, in JP-A-3-296745 and JP-A-4-31854 may also be used in the emulsion of the present invention.

The amount used of the sensitizing dye is suitably from 0.001 g to 20 g and preferably from 0.01 g to 2 g per 100 g of the silver used for the preparation of the emulsion.

Chemical Sensitization

The silver halide emulsion for use in the present invention may not be chemical sensitized but is preferably chemical sensitized and increased in sensitivity. Chemical sensitization includes sulfur sensitization, gold sensitization, reduction sensitization and combinations of them.

In addition to the above, chemical sensitization by compounds containing chalcogen element other than sulfur such as selenium, tellurium, etc., or chemical sensitization by noble metals such as palladium or iridium may be used in combination with the above chemical sensitization.

Further, a method of adding an inhibitor such as a nitrogen-containing heterocyclic compound represented by 4-hydroxy-6-methyl-1,3,3a,7-tetraazaindene may also preferably be used. The addition amount is preferably from $10^{-1}$ to $10^{-5}$ mol per mol of silver halide.

The pH during chemical sensitization is preferably from 5.3 to 10.5 and more preferably from 5.5 to 9.5.

A compound containing sulfur which can react with active gelatin and silver is used as a sulfur sensitizer, for example, thiosulfate, allyl thiocarbamide, thiourea, allyl isothiacyanate, cystine, p-toluenethiosulfonic acid, rhodanine and mercapto compounds are used. Further, those disclosed in U.S. Pat. Nos. 1,574,944, 2,410,689, 2,278,947, 2,728,668 and 3,656,955 can also be used.

The coating amount of light-sensitive silver halide in the present invention is from 1 mg/m$^2$ to 10 g/m$^2$ in terms of silver.

Silver halide emulsion may be used without post-ripening but is usually chemical sensitized. Known sulfur sensitization, reduction sensitization, noble metal sensitization and selenium sensitization which are known in the emulsion for general photographic material can be used alone or in combination. These chemical sensitization can be carried out in the presence of a nitrogen-containing heterocyclic compound (JP-A-62-253159).

The coating amount of light-sensitive silver halide in the present invention is from 1 mg/m$^2$ to 10 g/m$^2$ in terms of silver.

When the present invention is applied to a heat-developable photographic material, an organometal salt can be used as an oxidizing agent in combination with the light-sensitive silver halide. Of such organometal salts, an organosilver salt is particularly preferably used.

Organic compounds which can be used to form the above described organosilver salt oxidizing agent include the benzotriazoles, fatty acids or other compounds disclosed in U.S. Pat. No. 4,500,626, columns 52 and 53. Further, the silver salt of carboxylic acid having an alkynyl group such as the phenylpropiolic acid silver disclosed in JP-A-60-113235, and the silver acetylide disclosed in JP-A-61-249044 are also useful. Two or more of organosilver salts may be used in combination.

The organosilver salt is used from 0.01 to 10 mol, preferably from 0.01 to 1 mol, per mol of the light-sensitive silver halide. The total coating amount of the light-sensitive silver halide and the organosilver salt is appropriately from 50 mg to 10 g/m$^2$ in terms of silver.

Various kinds of antifoggants and photographic stabilizers can be used in the present invention. For example, the azoles and the azaindenes disclosed in RD, No. 17643 (1978), pages 24 and 25, the carboxylic acids and phosphoric acids containing nitrogen disclosed in JP-A-59-168442, the mercapto compounds and metal salts thereof disclosed in JP-A-59-111636, and the acetylene compounds disclosed in JP-A-62-87957 can be used for that purpose.

Hydrophilic binder is preferably used as the binders for the constitutional layers for a photographic material and a dye fixing element, for example those disclosed in JP-A-62-253159, pages 26 to 28 can be cited. Specifically, a transparent or translucent hydrophilic binder is preferred, for example, proteins such as gelatin and gelatin derivatives, or cellulose derivatives, natural compounds such as polysaccharides, e.g., starch, gum arabic, dextran, pulluran, and polyvinyl alcohol, polyvinyl pyrrolidone, acrylamide polymer, and other synthetic high molecular compounds. In addition, the high water-absorbing polymers as disclosed in JP-A-62-245260, that is, homopolymers of vinyl monomer having —COOM or —SO$_3$M (M represents a hydrogen atom or an alkali metal), or copolymers of this vinyl monomer or with other vinyl monomers (e.g., sodium methacrylate, ammonium methacrylate, Sumikagel L-5H of Sumitomo Chemicals, Co., Ltd.) can also be used. These binders may be used in combination of two or more.

When using the method of heat development by supplying a trace amount of water; water absorption can be conducted rapidly by using the above high water-absorbing polymers. Further, when a high water-absorbing polymer is used in a dye fixing layer or a protective layer therefor, the dyes after transfer can be prevented from being transferred again from the dye fixing element to other elements.

The coating amount of the binder in the present invention is preferably 20 g or ,less, more preferably 10 g or less, and most preferably 7 g or less, per m$^2$ of the photographic material.

A photographic material or constitutional layers (including a backing layer) of a dye fixing element may contain various polymer latexes for the purpose of improving physical properties of the film such as dimensional stability, curling prevention, adhesion prevention, prevention of cracking of the film, prevention of pressure increase and decrease, etc. Specifically, the polymer latexes disclosed in JP-A-62-245258, JP-A-62-136648 and JP-A-62-110066 can be used. In particular, by using a polymer latex having a low glass transition point (40° C. or less) in a mordant layer, cracking of the mordant layer can be prevented, and when a polymer latex having a high glass transition point is used in a backing layer, curling preventing effect can be obtained.

Reducing agents known in the field of photographic materials can be used in the present invention. Dye-donating compounds described below having a reducing property are also included (in such a case other reducing agents can be used in combination). Further, reducing agent precursors which do not have reducing property themselves but manifest that during development process by the action of a nucleophilic reagent or heat can also be used.

Examples of the reducing agent which are used in the present invention include the reducing agents and the reducing agent precursors disclosed in U.S. Pat. Nos. 4,500,626, columns 49 to 50, 4,483,914, columns 30 to 31, 4,330,617, 4,590,152, JP-A-60-140335, pages 17 and 18, JP-A-57-40245, JP-A-56-138736, JP-A-59-178458, JP-A-59-53831, JP-A-59-182449, JP-A-59-182450, JP-A-60-119555, JP-A-60-128436 to JP-A-60-128439, JP-A-60-198540, JP-A-60-181742, JP-A-61-259253, JP-A-62-244044, JP-A-62-131253 to JP-A-62-131256, and European Patent 220, 746A2, pages 78 to 96.

The combinations of various reducing agents as disclosed in U.S. Pat. No. 3,039,869 can also be used.

When using a diffusion resisting reducing agent, to accelerate electron transfer between the diffusion resisting reducing agent and developable silver halide, an electron transferring agent and/or an electron transferring agent precursor can be used in combination according to necessity.

An electron transferring agent or a precursor thereof can be selected from the above described reducing agents or precursors thereof. The transferability of the electron transferring agent or the precursor thereof is preferably larger than that of the diffusion resisting reducing agent (electron donor). Particularly useful electron transferring agents are 1-phenyl-3-pyrazolidones and aminophenols.

As the diffusion resisting reducing agents (electron donor) which are used in combination with the electron transferring agent, of the above described reducing agents those substantially do not transfer in the layer of the photographic material may be sufficient, and preferably hydroquinones, sulfonamidophenols, sulfonamidonaphthols, the compounds disclosed in JP-A-53-110827 as the electron donors and the dye-donating compounds which are diffusion resisting and have a reducing property described below can be cited.

The addition amount of the reducing agent in the present invention is from 0.01 to 20 mol and particularly preferably from 0.1 to 10 mol, per mol of silver.

Compounds which form or release a mobile dye corresponding or reversely corresponding to the reaction when silver ion is reduced to silver under high temperature, that is, dye-donating compounds, are contained in the present invention.

Examples of the dye-donating compounds other than the compounds represented by formula (I) of the present invention include the compounds represented by the following formula (LI):

(Dye-G)$_q$—Y  (LI)

wherein Dye represents a dye group, a dye group made temporarily shortwave or a dye precursor group (particularly donating magenta and cyan colors), and q, G and Y are the same as those in formula (II).

Hydrophobic additives such as dye-donating compounds and diffusion resisting reducing agents can be included in the layer of the photographic material by known methods such as those disclosed in U.S. Pat. No. 2,322,027. In such a case the high boiling point organic solvents disclosed in JP-A-59-83154, JP-A-59-178451, JP-A-59-178452, JP-A-59-178453, JP-A-59-178454, JP-A-59-178455 and JP-A-59-178457 can be used in combination with low boiling point organic solvents having a boiling point of from 50° C. to 160° C., if necessary.

The amount of the high boiling point organic solvent is 10 g or less and preferably 5 g or less, per g of the dye-donating compound used, and 1 cc or less, preferably 0.5 cc or less, and particularly preferably 0.3 cc or less, per g of the binder.

The dispersion method by the polymers disclosed in JP-B-51-39853 and JP-A-51-59943 can also be used.

When the compounds are substantially insoluble in water, they can be incorporated into the layer by dispersing in a binder as fine grains.

Various surfactants can be used when dispersing hydrophobic compounds in hydrophilic colloid. For example, the surfactants disclosed in JP-A-59-157636, pages 37 and 38 can be used.

Compounds for activating development of photographic materials and stabilizing images can be used in the present invention. Specific examples of the compounds preferably used for such purposes are disclosed in U.S. Pat. No. 4,500,626, columns 51 and 52.

Non-diffusive filter dyes can be used in the present invention for improving sharpness. Filter dyes having absorption in the infrared region can also be used, if necessary, in the present invention. The details of such filter dyes are disclosed in Japanese Patent Application No. 2-137885, JP-A-4-217243, JP-A-4-276744 and JP-A-5-45834.

In the system of forming images by diffusion transfer of dyes, a dye fixing element is used with the photographic material. The dye fixing element may be in the form of being separately coated on a separate support from the support of the photographic material or may be in the form of being coated on the same support of the photographic material. The mutual relationships between the dye fixing element and the photographic material, support, white reflecting layer disclosed in U.S. Pat. No. 4,500,626, column 57 can be applied to the present invention.

The dye fixing element preferably used in the present invention comprises at least one layer containing a mordant and a binder. Known mordants in the photographic field can be used and specific examples thereof include the mordants disclosed in U.S. Pat. No. 4,500,626, columns 58 and 59, JP-A-61-88256, pages 32 to 41, JP-A-62-244043 and JP-A-62-244036. Further, a dye-accepting high molecular compound such as those disclosed in U.S. Pat. No. 4,463,079 may be used.

The dye fixing element may be provided with an auxiliary layer such as a protective layer, a peeling-off layer, and a curling preventing layer, if necessary. In particular, the provision of a protective layer is useful.

A hydrophilic binder is preferably used as the binder for the constitutional layers of the photographic material and the dye fixing element. Examples thereof are disclosed in JP-A-62-253159, pages 26 to 29. Specifically, a transparent or translucent hydrophilic binder is preferred, for example, proteins such as gelatin and gelatin derivatives, or cellulose derivatives, natural compounds such as polysaccharides, e.g., starch, gum arabic, dextran, pulluran, and polyvinyl alcohol, polyvinyl pyrrolidone, acrylamide polymer, and other synthetic high molecular compounds. In addition, the high water-absorbing polymers as disclosed in JP-A-62-245260, that is, homopolymers of vinyl monomer having —COOM or —SO$_3$M (M represents a hydrogen atom or an alkali metal), or copolymers of this vinyl monomer or with other vinyl monomers (e.g., sodium methacrylate, ammonium methacrylate, Sumikagel L-5H of Sumitomo Chemicals, Co., Ltd.) can also be used. These binders may be used in combination of two or more.

When using the method of heat development by supplying a trace amount of water, water absorption can be conducted rapidly by using the above high water-absorbing polymers. Further, when a high water-absorbing polymer is used in a dye fixing layer or a protective layer therefor, the dyes after transfer can be prevented from being transferred again from the dye fixing element to other elements.

The coating amount of the binder in the present invention is preferably 20 g or less, more preferably 10 g or less, and most preferably 7 g or less, per m$^2$ of the photographic material.

The constitutional layers of the photographic material and the dye fixing element can contain a plasticizer, a sliding agent, or a high boiling point organic solvent as a peeling-off improver of the photographic material and the dye fixing element. Specific examples are disclosed in JP-A-62-253159, page 25, and JP-A-62-245253. Further, various silicone oils can be used for the above purpose (every silicone oil from dimethyl silicone oils to modified silicone oils by introducing various organic groups into dimethylsiloxane). As examples thereof, various modified silicone oils, in particular, carboxy-modified silicone oil (trade name: X-22-3710), disclosed in Shin-Etsu Silicone Co., Ltd., *Modified Silicone Oil*, technical data P6-18B are useful. Moreover, the silicone oils disclosed in JP-A-62-215953 and JP-A-63-46449 are also useful.

A discoloration inhibitor may be used in the photographic material and dye fixing element. As the discoloration inhibitor, for example, an oxidation preventing agent, an ultraviolet absorbing agent or a certain kind of metal complexes are used.

As the oxidation preventing agent, for example, there are chroman based compounds, coumaran based compounds, phenol based compounds (e.g., hindered phenols), hydroquinone derivatives, hindered amine derivatives, and spiroindan based compounds. The compounds disclosed in JP-A-61-159644 can also be useful as the oxidation preventing agent.

As the ultraviolet absorbing agent, there are benzotriazole based compounds (those disclosed in U.S. Pat. No. 3,533, 794, etc.), 4-thiazolidone based compounds (those disclosed in U.S. Pat. No. 3,352,681, etc.), benzophenone based compounds (JP-A-46-2784, etc.), and the compounds disclosed in JP-A-54-48535, JP-A-62-136641 and JP-A-61-88256. Further, the ultraviolet absorbing polymers disclosed in JP-A-62-260152 are also useful.

As the metal complexes, there are the compounds disclosed in U.S. Pat. Nos. 4,241,155, 4,245,018, columns 3 to 36, 4,254,195, columns 3 to 8, JP-A-62-174741, JP-A-61-88256, pages 27 to 29, JP-A-63-199248, JP-A-1-75568 and JP-A-1-74272.

Examples of useful discoloration inhibitors are disclosed in JP-A-62-215272, pages 125 to 137.

The discoloration inhibitors may be previously incorporated in the dye fixing element to prevent the discoloration of the dyes transferred to the dye fixing element, or may be supplied to the dye fixing element from the outside such as the photographic material.

The above oxidation preventing agent, ultraviolet absorbing agent and metal complex may be used in combination.

A brightening agent may be used in the photographic material and the dye fixing element. In particular, it is preferred to incorporate the brightening agent in the dye fixing element or to be supplied from the outside such as the photographic material. As one example thereof, the compounds disclosed in K. Veenkataraman, *The Chemistry of Synthetic Dyes*, Vol. V, Chap. 8, and JP-A-61-143752 can be cited. Specifically, stilbene based compounds, coumarin based compounds, coumarin based compounds, biphenyl based compounds, benzoxazolyl based compounds, naphthalimide based compounds, pyrazoline based compounds, and carbostyril based compounds can be included. The brightening agent can be used in combination with the discoloration inhibitor.

As the hardening agents for use in the constitutional layers of the photographic material and the dye fixing element, there can be cited the hardening agents disclosed in U.S. Pat. No. 4,678,739, column 41, JP-A-59-116655, JP-A-62-245261 and JP-A-61-18942. Specifically, aldehyde based hardening agents (e.g., formaldehyde), aziridine based hardening agents, epoxy based hardening agents, vinyl sulfone based hardening agents (e.g., N,N'-ethylene-bis (vinylsulfonylacetamido)ethane), N-methylol based hardening agents (e.g., dimethylolurea), and high polymer hardening agents (e.g., the compounds disclosed in JP-A-62-234157) can be enumerated.

The constitutional layers of the photographic material and the dye fixing element can contain various surfactants for purposes of coating aid, peeling-off improvement, sliding property improvement, static prevention, and development acceleration. Specific examples thereof are disclosed in JP-A-62-173463 and JP-A-62-183457.

The constitutional layers of the photographic material and the dye fixing element may contain organic fluoro compounds for purposes of sliding property improvement, static prevention, and peeling-off improvement. As the representative examples of the organic fluoro compounds, the fluorine based surfactants disclosed in JP-B-57-9053, columns 8 to 17, JP-A-61-20944 and JP-A-62-135826, and hydrophobic fluorine compounds such as fluorine based oily compounds, e.g., fluoro oil, and fluorine based solid compounds, e.g., tetrafluorinated ethylene resins can be enumerated.

The constitutional layers of the photographic material and the dye fixing element may contain a matting agent. Such a matting agent includes the compounds such as silicon dioxide, polyolefin and polymethacrylate disclosed in JP-A-61-88256, page 29 and the compounds such as benzoguanamine resin beads, polycarbonate resin beads, and AS resin beads disclosed in JP-A-63-274944 and JP-A-63-274952. A matting agent can also be used for the purpose of non-glossing of the surface of the dye fixing element (the surface of the images), as well as adhesion prevention, adjustment of sliding property and prevention of Newton ring.

In addition to the above, the constitutional layers of the photographic material and the dye fixing element may contain a thermal solvent, a defoaming agent, fungicide, biocide, and colloidal silica, etc. Specific examples of these additives are disclosed in JP-A-61-88256, pages 26 to 32.

The photographic material and/or the dye fixing element of the present invention can contain image forming accelerators. The image forming accelerators have functions of acceleration of the oxidation reduction reaction of the silver salt oxidizing agent and the reducing agent, acceleration of the reactions such as the formation of dyes from the dye-donating material, decomposition of the dyes, or the release of diffusive dyes, and acceleration of the transfer of the dyes from the photographic material to the dye fixing element, and they are classified from the physicochemical functions to a base, a base precursor, a nucleophilic compound, a high boiling point organic solvent (oil), a thermal solvent, a surfactant, a compound having an interaction with silver or silver ion. However, these materials usually have a composite function and commonly possess some of the above accelerating effects. Details of these are disclosed in U.S. Pat. No. 4,678,739, columns 38 to 40.

As the base precursors, there are salts of organic acid and base decarbonated by heat, and compounds which release amines by intramolecular nucleophilic substitution reaction, Lossen rearrangement and Beckmann rearrangement. Specific examples thereof are disclosed in U.S. Pat. No. 4,511, 493 and JP-A-62-65038.

In the system in which heat development and dye transfer are simultaneously carried out in the presence of a trace amount of water, it is preferred to incorporate base and/or base precursor in the dye fixing element in the point of increasing the storage stability of the photographic material.

In addition to the above, the combination of the hardly soluble metal compounds disclosed in European Patent 210,660 and U.S. Pat. No. 4,740,445 and the compound which can react with the metal ion constituting the hardly soluble metal compound to form a complex (a complex-forming compound), and the compound which form a base by electrolysis disclosed in JP-A-61-232451 can be used as base precursors. In particular, the former method is effective. The hardly soluble metal compound and the complex-forming compound are preferably added separately to the photographic material and the dye fixing element.

The photographic material and/or dye fixing element of the present invention can use various development stoppers for obtaining uniform quality of images against variation of the processing temperature and processing time during development.

The development stopper herein means a compound which, after optimal development, rapidly neutralizes or reacts with the base and decreases the concentration of the base in the film and stops development, or a compound which inhibits development by interacting with the silver and the silver salt. Specifically, acid precursors which release acid by heating, eleqtrophilic compounds which are substituted with the coexisting base by a substitution reaction by heating, nitrogen-containing heterocyclic compounds, mercapto compounds and precursors thereof can be included in the development stopper. Further details are disclosed in JP-A-62-253159, pages 31 and 32.

Supports which can resist the processing temperature can be used in the photographic material and the dye fixing element in the present invention. In general, paper and synthetic high polymer (film) are used. Specifically, polyethylene terephthalate, polycarbonate, polyvinyl chloride, polystyrene, polypropylene, polyimide, celluloses (e.g., triacetyl cellulose), these films in which a pigment such as titanium oxide is contained, synthetic paper made from polypropylene and the like, mixed paper made from synthetic resin such as polyethylene and natural pulp, Yankee paper, baryta paper, coated paper (in particular, cast coated paper), metal, cloth and glass are used.

These supports may be used alone or the support may be such that whose one surface or both surfaces are laminated with synthetic high polymer such as polyethylene.

In addition, the supports disclosed in JP-A-62-253159, pages 29 to 31 may be used.

The surface of the support may be coated with a hydrophilic binder and a semiconductor metal oxide, e.g., alumina sol and tin oxide, or other antistatic agents such as carbon black and the like.

As the method of recording images on a photographic material by exposure, there are a method in which image information is exposed via an electric signal and by emitting light emitting diode and various lasers, and a method of outputting image information to image display apparatus such as CRT, liquid crystal display, electroluminescence display, or plasma display, and exposing directly or through an optical system. Specifically, the exposure methods disclosed in JP-A-2-129625, Japanese Patent Application Nos. 3-338182, 4-009388 and 4-281442 can be used.

As the light sources for recording images on a photographic material, the light sources disclosed in U.S. Pat. No. 4,500,626, column 56, such as the light emitting diode, the laser light source, and CRT light source can be used.

The magnetic recording layer preferably used in the present invention is described below.

The magnetic recording layer is a layer coated on a support with a water-soluble or organic solvent based coating solution comprising magnetic grains dispersed in a binder.

Magnetic grains for use in the present invention include ferromagnetic iron oxide such as $\gamma$-$Fe_2O_3$, Co-doped $\gamma$-$Fe_2O_3$, Co-doped magnetite, Co-containing magnetite ferromagnetic chroimium dioxide, ferromagnetic metal, ferromagnetic alloy, hexagonal system Ba ferrite, Sr ferrite, Pb ferrite, and Ca ferrite. Co-doped ferromagnetic iron oxide such as Co-doped $\gamma$-$Fe_2O_3$ is preferred. The shape of the grain may be any of acicular shape, a granular shape, a spherical shape, a cubic shape, or a tabular shape. The specific surface area ($S_{BET}$) is preferably 20 $m^2$/g or more, and particularly preferably 30 $m^2$/g or more. The saturation magnetization ($\sigma_s$) of the ferromagnetic substance is preferably from $3.0 \times 10^4$ to $3.0 \times 10^5$ A/m and particularly preferably from $4.0 \times 10^4$ to $2.5 \times 10^5$ A/m. The ferro-magnetic grains may be surface treated with silica and/or alumina and organic materials. Further, the surface of the magnetic grains may be treated with a silane coupling agent or a titanium coupling agent as disclosed in JP-A-6-161032. In addition, the magnetic grains the surfaces of which are covered with inorganic or organic substance as disclosed in JP-A-4-259911 and JP-A-5-81652 can also be used.

The binder which can be used for the magnetic grains includes the thermoplastic resins, thermosetting resins, radiation hardening resins, reactive resins, acid-, alkali- or biodegradable polymers, natural polymers (e.g., cellulose derivatives, sugar derivatives), and mixtures thereof disclosed in JP-A-4-219569. The above described resins have a Tg value of from $-40°$ C. to $300°$ C., and a weight average molecular weight of from 2,000 to 1,000,000. Examples of the binders include vinyl based copolymers, cellulose derivatives such as cellulose diacetate, cellulose triacetate, cellulose acetate propionate, cellulose acetate butyrate and cellulose tripropionate, acrylic resins, and polyvinyl acetal resins. Gelatin is also preferably used. Cellulose di(tri) acetate is particularly preferred. The binder can be hardening treated by adding epoxy based, aziridine based or isocyanate based crosslinking agent. Examples of the isocyanate based cross-linking agents include isocyanates such as tolylenediisocyanate, 4,4'-diphenylmethanediisocyanate, hexamethylenediisocyanate and xylylenediisocyanate, reaction products of these isocyanates with polyalcohols (e.g., a reaction product of 3 mol of tolylenediisocyanate with 1 mol of trimethylolpropane), and polyisocyanate formed by condensation of these isocyanates, and examples thereof are disclosed in JP-A-6-59357.

The above magnetic substances are dispersed in a binder preferably using, as disclosed in JP-A-6-35092, a kneader, a pin type mill, and an annular type mill, and the combined use is also preferred. The dispersants disclosed in JP-A-5-88283 or other known dispersants can be used. The thickness of the magnetic recording layer is from 0.1 μm to 10 μm, preferably from 0.2 μm to 5 μm, and more preferably from 0.3 μm to 3 μm. The weight ratio of the magnetic grains to the binder is preferably from 0.5/100 to 60/100, and more preferably from 1/100 to 30/100. The coating amount of the magnetic grains is from 0.005 to 3 $g/m^2$, preferably from 0.01 to 2 $g/m^2$, and more preferably from 0.02 to 0.5 $g/m^2$. The transmission yellow density of the magnetic recording layer is preferably from 0.01 to 0.50, more preferably from 0.03 to 0.20 and particularly preferably from 0.04 to 0.15.

The magnetic recording layer can be provided on the back surface of the photographic support entirely or in stripe by coating or printing. Coating of the magnetic recording layer can be carried out by means of air doctor coating, blade coating, air knife coating, squeeze coating, impregnation coating, reverse-roll coating, transfer-roll coating, gravure coating, kiss coating, cast coating, spray coating, dip coating, bar coating, or extrusion coating, and the coating solutions disclosed in JP-A-5-341436 are preferably used.

The magnetic recording layer may be provided with functions of lubrication improvement, curling adjustment, antistatic property, adhesion prevention and head abrasion, or another functional layer having these functions may be provided, and at least one kind of the grain is preferably an abrasive of non-spherical inorganic grain having Mohs' hardness of 5 or more. The composition of the non-spherical inorganic grain is preferably oxide such as aluminum oxide, chromium oxide, silicon dioxide, titanium dioxide, and carbide such as silicon carbide and titanium carbide, and fine powders such as diamond. The surface of these abrasives may be treated with a silane coupling agent or a titanium coupling agent. These grains may be added to the magnetic recording layer, or may be overcoated on the magnetic recording layer (e.g., a protective layer, a lubricating layer). The above described binders can be used at this time, preferably the same binder as the binder of the magnetic recording layer. Photogrmagnetic materials having the magnetic recording layer are disclosed in U.S. Pat. Nos. 5,336, 589, 5,250,404, 5,229,259, 5,215,874 and EP 466,130.

The polyester support preferably used in the present invention is described below, but details including photographic materials described later, processing, cartridges and examples are disclosed in Kokai-Giho, Kogi No. 94-6023 (Hatsumei-Kyokai, Mar. 15, 1994). The polyester for use in the present invention comprises diol and aromatic dicarboxylic acid as essential components, and as aromatic dicarboxylic acids, 2,6-, 1,5-, 1,4- and 2,7-naphthalenedicarboxylic acid, terephthalic acid, isophthalic acid, and phthalic acid, and as diols diethylene glycol, triethylene glycol, cyclohexanedimethanol, bisphenol A, and bisphenol can be enumerated. Polymerization polymers thereof include homopolymers such as polyethylene terephthalate, polyethylene naphthalate, polycyclohexanedimethanol terephthalate. Particularly preferred is polyester comprising from 50 mol % to 100 mol % of 2,6-naphthalenedicarboxylic acid. Particularly preferred above all is polyethylene 2,6-naphthalate. The average molecular weight of them is about 5,000 to 200,000. Tg of the polyester of the present invention is 50° C. or more and 90° C. or more is preferred.

The polyester support is heat treated at 40° C. or more and less than Tg, more preferably from Tg minus 20° C. to less than Tg for the purpose of being reluctant to get curling habit. The heat treatment may be carried out at constant temperature within this range or may be carried out with cooling. The heat treatment time is from 0.1 hours to 1,500 hours, preferably from 0.5 hours to 200 hours. The heat treatment of the support may be carried out in a roll state or may be carried out in a web state while transporting. The surface of the support may be provided with concave and convex (e.g., coating conductive inorganic fine grains such as $SnO_2$ or $Sb_2O_5$) to improve the surface state. Further, it is desired to contrive so as to prevent cut end mark by providing knurling at the end part and make only the end part a little high. The heat treatment may be carried out at any stage of after the film formation, after the surface treatment, after backing layer coating (an antistatic agent, a sliding agent), or after undercoating, but preferably after coating of an antistatic agent.

An ultraviolet absorbing agent may be incorporated into the polyester support. Further light piping can be prevented by including the commercially available dye or pigment for polyester such as Diaresin manufactured by Mitsubishi Kasei Corp. or Kayaset manufactured by Nippon Kayaku Co., Ltd.

To ensure adhesion of the support and the constitutional layers of the photographic material, the surface activation treatment is preferably carried out, such as a chemical treatment, a mechanical treatment, a corona discharge treatment, a flame treatment, an ultraviolet treatment, a high frequency treatment, a glow discharge treatment, an active plasma treatment, a laser treatment, a mixed acid treatment, and an ozone oxidation treatment, and prefered of them are an ultraviolet irradiation treatment, a flame treatment, a corona discharge treatment, and a glow discharge treatment.

Undercoating method is described below. Subbing layer may be a single layer or may be two or more layers. The binder for a subbing layer include copolymers with monomers selected from vinyl chloride, vinylidene chloride, butadiene, methacrylic acid, acrylic acid, iraconic acid and maleic anhydride being starting materials, polyethyleneimine, an epoxy resin, grafted gelatin, nitrocellulose and gelatin. Compounds which swell the support include resorcin and p-chlorophenol. A gelatin hardening agent for a subbing layer include chromium salt (chrome alum), aldehydes (formaldehyde, glutaraldehyde), isocyanates, active halide compounds (2,4-dichloro-6-hydroxy-s-triazine), epichlorohydrin resins, and active vinyl sulfone compounds. $SiO_2$, $TiO_2$, inorganic fine grains or polymethyl methacrylate copolymer fine grains (0.01 to 10 μm) may be contained as a matting agent.

Further, antistatic agents preferably used include high polymers containing carboxylic acid and carboxylic acid salt, sulfonic acid salt, cationic high polymer, and ionic surfactant compounds.

Most preferred antistatic agents are fine grains of crystalline metal oxide of at least one grain selected from ZnO, $TiO_2$, $SnO_2$, $Al_2O_3$, $In_2O_3$, $SiO_2$, MgO, BaO, $MoO_3$, $V_2O_5$ having the volume resistivity of $10^7$ω·cm or less, more preferably $10^5$ω·cm or less and having a grain size of from 0.001 to 1.0 μm or composite oxides of them (Sb, P, B, In, S, Si, C), metal oxide in the form of sol or fine grains of these composite oxides. The addition amount to the photographic material is preferably from 5 to 500 mg/m² and particularly preferably from 10 to 350 mg/m². The ratio of the conductive crystalline oxides or composite oxides thereof to the binder is preferably from 1/300 to 100/1 and more preferably from 1/100 to 100/5.

It is preferred for the photographic material to have a sliding property. The sliding agent-containing layer is preferably provided on both of light-sensitive layer surface and backing layer surface. Preferred sliding property is a dynamic friction coefficient of from 0.25 to 0.01. Measurement was conducted at this time using a stainless steel ball having a diameter of 5 mm at a transporting speed of 60 cm/min (25° C., 60% RH). In this evaluation, when the opposite material is replaced with the light-sensitive layer surface, almost the same level of value can be obtained.

The sliding agent which can be used in the present invention include polyorganosiloxane, higher fatty acid amide, higher fatty acid metal salt, higher fatty acid and higher alcohol ester. As polyorganosiloxane, polydimethylsiloxane, polydiethylsiloxane, polystyrylmethylsiloxane, and polymethylphenylsiloxane can be used. The addition layer is preferably the outermost layer of the emulsion layer or a backing layer. In particular, esters having polydimethylsiloxane or a long chain alkyl group are preferred.

The photographic material of the present invention preferably contains a matting agent. The matting agent may be added to either of the emulsion layer side or the backing layer side but it is particularly preferably to be added to the outermost layer of the emulsion layer. The matting agent may be either soluble or insoluble in the processing solution, preferably both types are used in combination. For example, polymethyl methacrylate, poly(methyl methacrylate/methactylic acid=9/1 or 5/5 (mol ratio)), polystyrene grains are preferably used. An average grain size is preferably from 0.8 to 10 μm, and grain size distribution is preferably narrow, preferably 90% or more of the entire grain number accounts for 0.9 to 1.1 times of the average grain size. For increasing the matting property, grains having a grain size of 0.8 μm or less are preferably added at the same time. For example, polymethyl methacrylate (0.2 μm), poly(methyl methacrylate/methacrylic acid=9/1 (mol ratio), 0.3 μm), polystyrene grains (0.25 μm), and colloidal silica (0.03 μm) are enumerated.

The film patrone preferably used in the present invention is described below. The main material of the pattone for use in the present invention may be metal or synthetic plastics.

Preferred plastic materials are polystyrene, polyethylene, polypropylene, polyphenyl ether, etc. Further, the patrone of the present invention may contain various antistatic agents, and carbon black, metal oxide grains, nonionic, anionic, cationic and betaine based surfactants or polymers are preferably used. Such a patrone static prevented is disclosed in JP-A-1-312537 and JP-A-1-312538. In particular, those having the resistivity of $10^{12}\omega$ or less at 25° C., 25% RH are preferred. Usually, plastic patrone is produced using plastics including carbon black or a pigment to impart light shielding. The size of the pattone may be 135 size of the present as it is, or for a compact size camera, it is effective that the diameter of the cartridge of 25 mm of the present 135 size may be decreased to 22 mm or less. The capacity of the case of the patrone is 30 cm³ or less and preferably 25 cm³ or less. The weight of the plastics used for the patrone and patrone case is preferably from 5 g to 15 g.

Further, the patrone may be a type of sending out the film by revolving a spool. Further, it may be the structure such that the tip of the film is encased in the body of the pattone and the tip of the film is sent to outside through the port of the patrone by revolving the axle of the spool in the feeding direction of the film. These are disclosed in U.S. Pat. Nos. 4,834,306 and 5,226,613. The photographic film for use in the present invention may be a raw film before development or may be a photographic film development processed. Further, a raw film and a processed film may be contained in the same patrone, or may be stored in different patrones.

The present invention is further described in detail below with reference to the examples, but the present invention should not be construed as being limited thereto.

EXAMPLE 1

A multilayer color photographic material was prepared as Sample 101 by coating each layer having the following composition on an undercoated cellulose triacetate film support.

Composition of Light-Sensitive Layer

The coated weights of silver halide and colloidal silver are shown in units of g/m² as silver, the coated weights of couplers, additives and gelatin are shown in units of g/m², and the coated weights of sensitizing dyes are shown as the number of mols per mol of the silver halide in the same layer. The meaning of symbols for additives are shown below. When the additives have plural functions; the symbols are shown as the additives for the most typical function.

| | |
|---|---|
| UV: | Ultraviolet Absorberbelow. |
| Solv: | High Boiling Point Organic Solvent |
| ExF: | Dye |
| ExS: | Sensitizing Dye |
| ExC: | Cyan Coupler |
| ExM: | Magenta Coupler |
| ExY: | Yellow Coupler |
| Cpd: | Additive |

First Layer: Antihalation Layer

| | |
|---|---|
| Black Colloidal Silver | 0.15 |
| Gelatin | 2.33 |
| UV-1 | $1.9 \times 10^{-2}$ |
| UV-2 | $4.7 \times 10^{-2}$ |
| UV-3 | $8.6 \times 10^{-2}$ |
| ExF-3 | $5.0 \times 10^{-3}$ |
| ExM-3 | $2.3 \times 10^{-2}$ |
| Solv-1 | 0.16 |
| Solv-2 | 0.10 |

Second Layer: Interlayer

| | |
|---|---|
| Gelatin | 0.88 |
| Polyethyl Acrylate Latex | $2.6 \times 10^{-1}$ |
| ExC-7 | $5.0 \times 10^{-2}$ |

Third Layer: Low Sensitivity Red-Sensitive Emulsion Layer

| | |
|---|---|
| Silver Iodobromide Emulsion A | 0.24 coated weight of silver |
| Silver Iodobromide Emulsion B | 0.65 coated weight of silver |
| Gelatin | 1.75 |
| ExS-1 | $6.9 \times 10^{-4}$ |
| ExS-2 | $4.0 \times 10^{-4}$ |
| ExS-5 | $6.7 \times 10^{-4}$ |
| ExS-7 | $1.4 \times 10^{-5}$ |
| ExC-1 | $3.0 \times 10^{-1}$ |
| ExC-5 | $2.0 \times 10^{-1}$ |
| ExC-9 | $2.2 \times 10^{-2}$ |
| Cpd-4 | $5.3 \times 10^{-2}$ |
| ExC-4 | $6.1 \times 10^{-2}$ |

Fourth Layer: Middle Sensitivity Red-Sensitive Emulsion Layer

| | |
|---|---|
| Silver Iodobromide Emulsion C | 0.67 coated weight of silver |
| Gelatin | 0.94 |
| ExS-1 | $3.5 \times 10^{-4}$ |
| ExS-2 | $2.0 \times 10^{-4}$ |
| ExS-5 | $3.4 \times 10^{-4}$ |
| ExS-7 | $6.9 \times 10^{-6}$ |
| ExC-1 | $1.3 \times 10^{-1}$ |
| ExC-4 | $4.6 \times 10^{-2}$ |
| ExC-5 | $8.6 \times 10^{-2}$ |
| ExC-6 | $1.1 \times 10^{-2}$ |
| ExC-7 | $4.6 \times 10^{-2}$ |
| Cpd-4 | $2.1 \times 10^{-2}$ |

Fifth Layer: High Sensitivity Red-Sensitive Emulsion Layer

| | |
|---|---|
| Silver Iodobromide Emulsion D | 0.67 coated weight of silver |
| Gelatin | 0.68 |
| ExS-1 | $3.2 \times 10^{-4}$ |
| ExS-2 | $1.8 \times 10^{-4}$ |
| ExS-5 | $3.1 \times 10^{-4}$ |
| ExS-7 | $4.8 \times 10^{-5}$ |
| ExC-1 | $5.1 \times 10^{-2}$ |
| ExC-6 | $9.0 \times 10^{-3}$ |
| ExC-4 | $2.0 \times 10^{-2}$ |
| ExC-9 | $1.0 \times 10^{-2}$ |
| Cpd-4 | $2.1 \times 10^{-3}$ |
| Solv-1 | 0.08 |
| Solv-2 | 0.04 |

Sixth Layer: Interlayer

| | |
|---|---|
| Gelatin | 0.62 |
| Cpd-1 | 0.08 |
| Polyethyl Acrylate Latex | $4.1 \times 10^{-2}$ |
| Solv-1 | $4.0 \times 10^{-2}$ |

Seventh Layer: Low Sensitivity Green-Sensitive Emulsion Layer

| | |
|---|---|
| Silver Iodobromide Emulsion E | 0.14 coated weight of silver |
| Gelatin | 0.49 |
| ExS-8 | $5.7 \times 10^{-5}$ |
| ExS-4 | $9.0 \times 10^{-4}$ |
| ExS-5 | $1.8 \times 10^{-4}$ |
| ExM-1 | 0.26 |
| Solv-1 | 0.15 |
| Solv-3 | $7.0 \times 10^{-3}$ |

Eighth Layer: Middle Sensitivity Green-Sensitive Emulsion Layer

| | |
|---|---|
| Silver Iodobromide Emulsion F | 0.08 coated weight of silver |
| Silver Iodobromide Emulsion E | 0.01 |

|  |  |
|---|---|
| Gelatin | 0.14 |
| ExS-8 | $4.3 \times 10^{-5}$ |
| ExS-4 | $6.8 \times 10^{-4}$ |
| ExS-5 | $1.3 \times 10^{-4}$ |
| ExM-1 | $4.9 \times 10^{-2}$ |
| ExM-7 | $1.0 \times 10^{-2}$ |
| ExY-1 | $5.0 \times 10^{-3}$ |
| Solv-1 | $3.3 \times 10^{-2}$ |
| Solv-3 | $1.5 \times 10^{-3}$ |

Ninth Layer: High Sensitivity Green-Sensitive Emulsion Layer

|  |  |
|---|---|
| Silver Iodobromide Emulsion G | 0.60 coated weight of silver |
| Gelatin | 0.60 |
| ExS-4 | $5.0 \times 10^{-4}$ |
| ExS-5 | $9.9 \times 10^{-5}$ |
| ExS-8 | $3.2 \times 10^{-5}$ |
| ExM-7 | $2.4 \times 10^{-2}$ |
| ExM-1 | $8.4 \times 10^{-2}$ |
| ExY-1 | $6.7 \times 10^{-2}$ |
| ExC-1 | $6.0 \times 10^{-3}$ |
| ExC-4 | $8.0 \times 10^{-3}$ |
| Cpd-6 | $8.0 \times 10^{-3}$ |
| Solv-1 | 0.12 |
| Solv-2 | 0.06 |
| Solv-3 | $6.0 \times 10^{-3}$ |

Tenth Layer: Interlayer

|  |  |
|---|---|
| Gelatin | 0.39 |
| UV-2 | $1.4 \times 10^{-2}$ |
| UV-3 | $1.6 \times 10^{-2}$ |
| UV-5 | $4.2 \times 10^{-2}$ |
| Cpd-1 | $2.6 \times 10^{-2}$ |
| Polyethyl Acrylate Latex | $1.4 \times 10^{-2}$ |
| Solv-1 | $2.8 \times 10^{-2}$ |

Eleventh Layer: Donor Layer Having Interlayer Effect for Red Sensitive Layers

|  |  |
|---|---|
| Silver Iodobromide Emulsion H | 1.12 coated weight of silver |
| Silver Iodobromide Emulsion I | 0.26 coated weight of silver |
| Gelatin | 1.61 |
| ExS-3 | $6.4 \times 10^{-4}$ |
| ExM-2 | $2.7 \times 10^{-2}$ |
| ExM-1 | $2.0 \times 10^{-1}$ |
| ExM-7 | $1.7 \times 10^{-1}$ |
| ExY-2 | $2.0 \times 10^{-1}$ |
| Solv-1 | 0.50 |

Twelfth Layer: Yellow Filter Layer

|  |  |
|---|---|
| Yellow Colloidal Silver | $3.3 \times 10^{-2}$ |
| Gelatin | 0.61 |
| Cpd-1 | $4.3 \times 10^{-2}$ |
| Cpd-2 | $7.9 \times 10^{-2}$ |
| Cpd-5 | $1.0 \times 10^{-3}$ |
| Solv-1 | $4.7 \times 10^{-2}$ |

Thirteenth Layer: Low Sensitivity Blue-Sensitivity Emulsion Layer

|  |  |
|---|---|
| Silver Iodobromide Emulsion J | 0.62 |
| Gelatin | 1.67 |
| ExS-9 | $8.8 \times 10^{-4}$ |
| ExY-2 | $1.2 \times 10^{-1}$ |
| ExY-3 | $3.5 \times 10^{-1}$ |
| ExC-9 | $6.3 \times 10^{-2}$ |
| ExC-1 | $3.0 \times 10^{-2}$ |
| ExC-10 | $8.4 \times 10^{-2}$ |
| Solv-1 | 0.33 |

Fourteenth Layer: High Sensitivity Blue-Sensitive Emulsion Layer

|  |  |
|---|---|
| Silver Iodobromide Emulsion K | 0.14 coated weight of silver |
| Silver Iodobromide Emulsion L | 0.10 coated weight of silver |
| Silver Iodobromide Emulsion M | 0.22 coated weight of silver |
| Gelatin | 1.00 |
| ExS-6 | $4.4 \times 10^{-4}$ |
| ExY-2 | $7.6 \times 10^{-2}$ |
| ExY-3 | $1.1 \times 10^{-1}$ |
| ExY-6 | $3.1 \times 10^{-1}$ |
| ExC-1 | $1.8 \times 10^{-2}$ |
| ExC-10 | $2.3 \times 10^{-2}$ |
| Solv-1 | $1.7 \times 10^{-1}$ |

Fifteenth Layer: First Protective Layer

|  |  |
|---|---|
| Fine Grained Silver Iodobromide Emulsion N | 0.06 coated weight of silver |
| Gelatin | 0.51 |
| UV-2 | $4.0 \times 10^{-2}$ |
| UV-3 | $4.9 \times 10^{-2}$ |
| UV-5 | 0.12 |
| Cpd-3 | 0.10 |
| ExF-4 | $2.1 \times 10^{-3}$ |
| ExF-5 | $6.3 \times 10^{-3}$ |
| Solv-4 | $2.0 \times 10^{-2}$ |
| Polyethyl Acrylate Latex | $9.0 \times 10^{-2}$ |

Sixteenth Layer: Second Protective Layer

|  |  |
|---|---|
| Fine Grained Silver Iodobromide Emulsion N | 0.18 |
| Gelatin | 0.84 |
| B-1 (diameter: 2.0 μm) | $8.0 \times 10^{-2}$ |
| B-2 (diameter: 2.0 μm) | $8.0 \times 10^{-2}$ |
| B-3 | $3.5 \times 10^{-2}$ |
| W-5 | $1.8 \times 10^{-2}$ |
| H-1 | 0.18 |

In addition to the above, 1,2-benzisothiazolin-3-one (200 ppm in average based on gelatin), n-butyl-p-hydroxybenzoate (1,000 ppm in average based on gelatin), and 2-phenoxyethanol (10,000 ppm in average based on gelatin) were added to the thus-produced sample. Further, W-1 to W-6, B-1 to B-6, F-1 to F-17, and iron salts, lead salts, gold salts, platinum salts, iridium salts and rhodium salts were appropriately included in each layer to improve storage stability, processing property, pressure resistance, fungicidal and biocidal properties, antistatic property and coating property.

TABLE 1

| Emulsion | Average AgI Content (%) | Average Grain Size Corresponding to Sphere (μm) | Variation Coefficient of Grain Size Distribution (%) | Diameter/ Thickness Ratio | Silver Amount Ratio [core/middle/shell] (AgI content) | Grain Structure and Form |
| --- | --- | --- | --- | --- | --- | --- |
| A | 4.7 | 0.40 | 10 | 1.0 | [40/10/50] (1/38/1) | triple structure, cubic grain |
| B | 1.7 | 0.46 | 15 | 5.5 | [5/55/40] (5/2/2) | triple structure, tabular grain |
| C | 7.9 | 0.53 | 18 | 4.0 | [6/45/49] (2/8/9) | triple structure, tabular grain |
| D | 8.8 | 0.65 | 15 | 3.5 | [12/59/29] (0/12/6) | triple structure, tabular grain |
| E | 1.7 | 0.46 | 15 | 5.0 | [5/55/40] (5/2/2) | triple structure, tabular grain |
| F | 7.9 | 0.51 | 18 | 4.0 | [6/45/49] (2/8/9) | triple structure, tabular grain |
| G | 3.5 | 0.55 | 15 | 3.5 | [12/59/29] (0/5/2) | triple structure tabular grain |
| H | 8.0 | 0.65 | 28 | 2.5 | [33/67] (18/3) | double structure, plate-like grain |
| I | 10.3 | 0.40 | 15 | 1.0 | [25/75] (29/4) | double structure, octahedral grain |
| J | 1.7 | 0.52 | 15 | 4.2 | [5/55/40] (5/2/2) | triple structure, tabular grain |
| K | 8.8 | 0.64 | 23 | 5.2 | [7/64/29] (0/11/8) | triple structure, tabular grain |
| L | 3.4 | 0.80 | 18 | 4.7 | [12/56/32] (0/1/9) | triple structure, tabular grain |
| M | 13.9 | 1.30 | 25 | 3.0 | [35/65] (34/3) | double structure, plate-like grain |
| N | 2.0 | 0.07 | 15 | 1.0 |  | uniform structure, fine grain |

In Table 1, (1) Emulsions A to M were subjected to reduction sensitization during preparation of the grains with thiourea dioxide and thiosulfonic acid according to the examples of JP-A-2-191938.

(2) Emulsions A to M were subjected to gold sensitization, sulfur sensitization and selenium sensitization in the presence of the spectral sensitizers indicated in each light-sensitive layer and sodium thiocyanate according the the examples of JP-A-3-237450.

(3) Low molecular weight gelatin was used in the preparation of tabular grains according to the examples of JP-A-1-158426.

(4) There were observed, using a high pressure electron microscope, such dislocation lines as disclosed in JP-A-3-237450 in tabular grains and regular crystal grains having a grain structure.

(5) Emulsions A to M contained iridium in the interior of the grains according to the method disclosed in B. H. Carroll, *Photographic Science and Engineering*, 24, 265 (1980), etc.

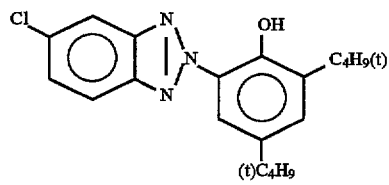

UV-1

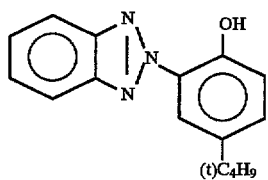

UV-2

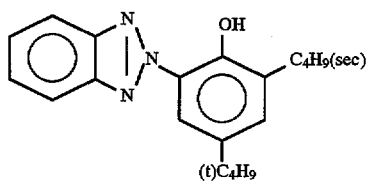

UV-3

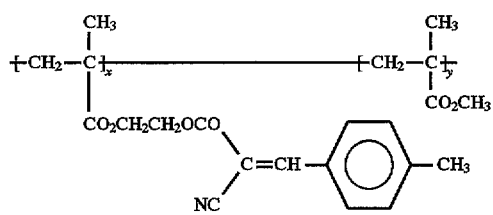
UV-4
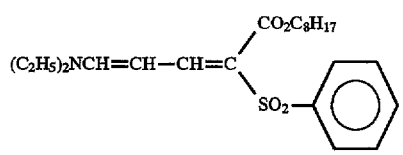
UV-5
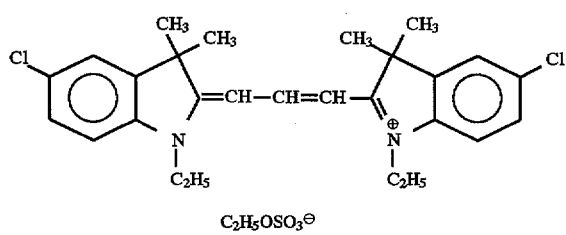
ExF-3
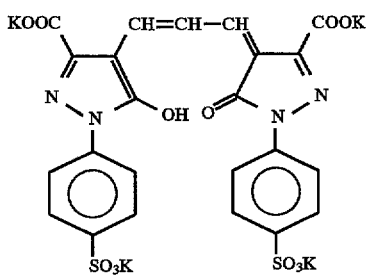
ExF-4
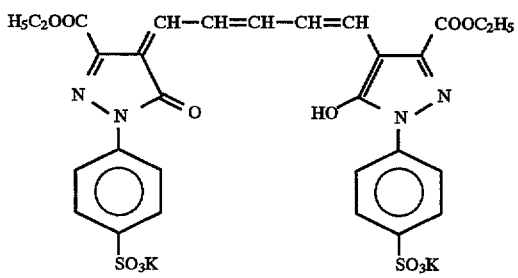
ExF-5
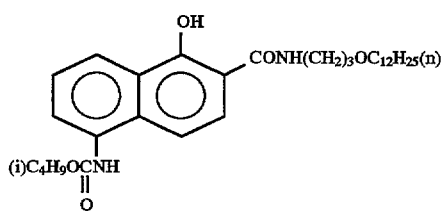
ExC-1

-continued
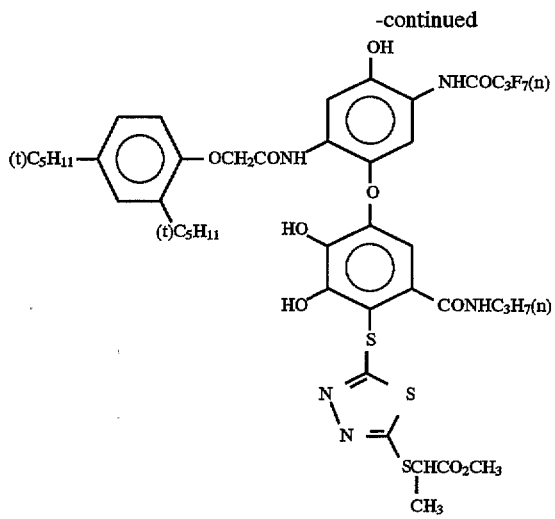
ExC-2
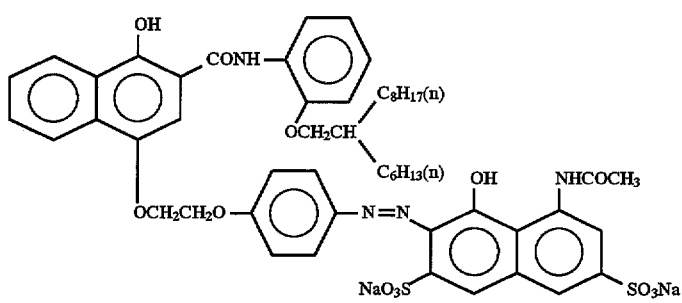
ExC-3
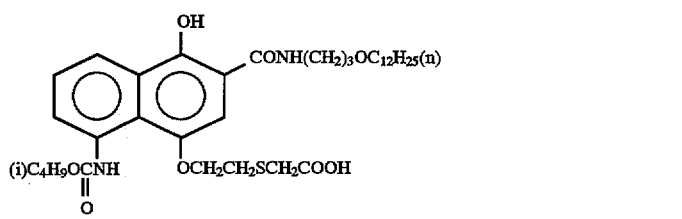
ExC-4
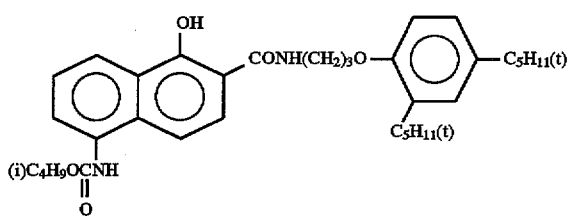
ExC-5
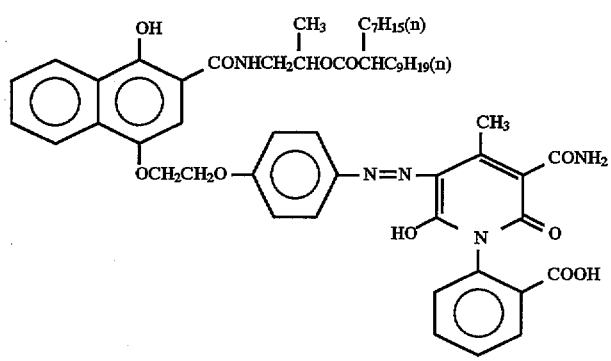
ExC-6

-continued
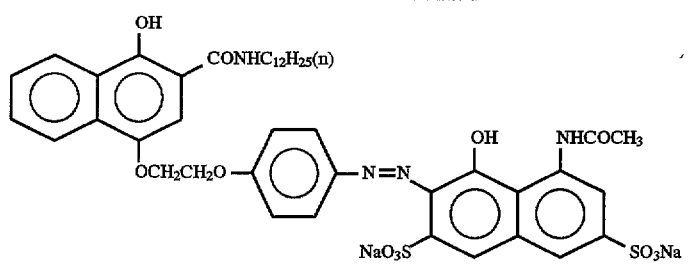
ExC-7
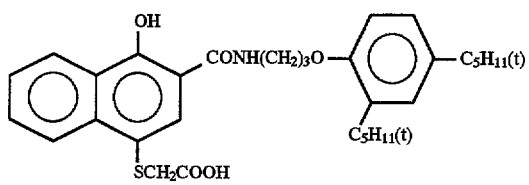
ExC-8
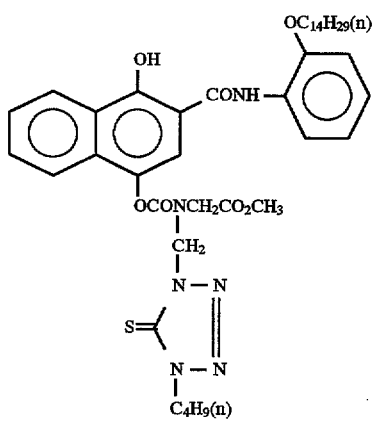
ExC-9
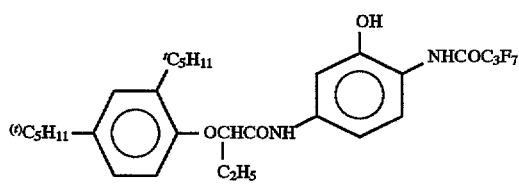
ExC-10
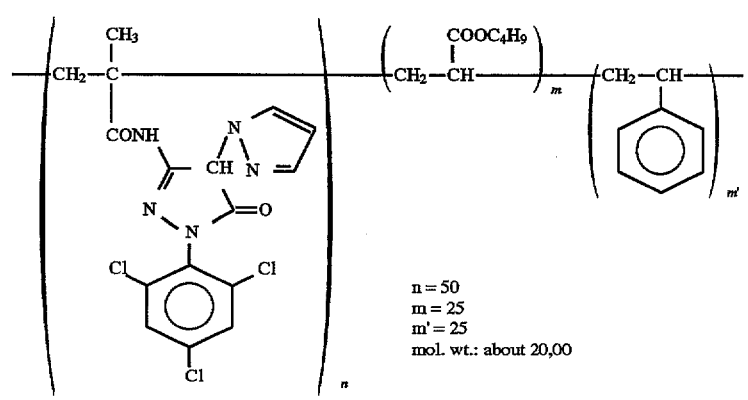
ExM-1
n = 50
m = 25
m' = 25
mol. wt.: about 20,00

-continued
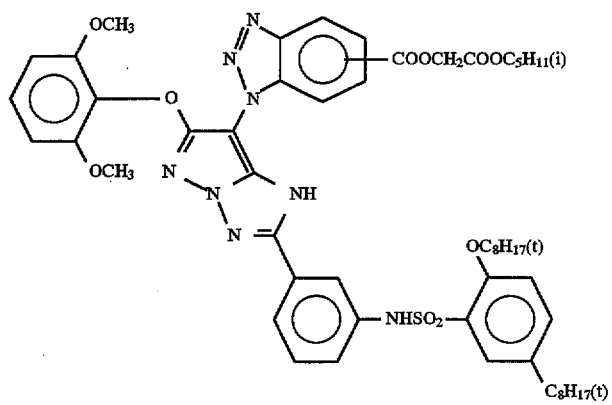
ExM-2
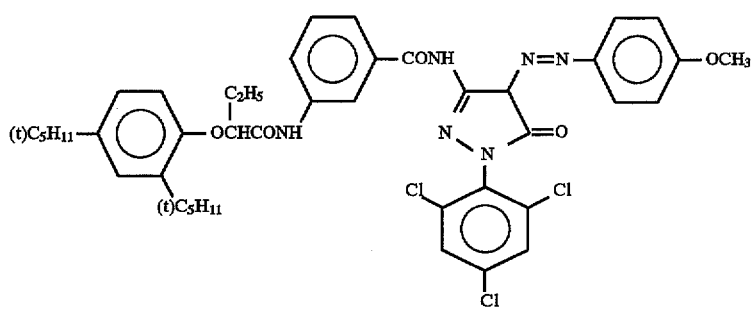
ExM-3
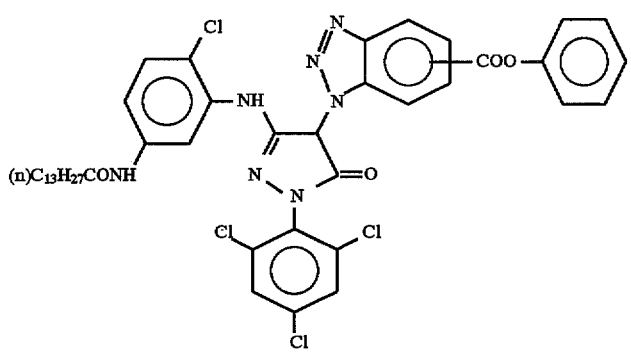
ExM-4
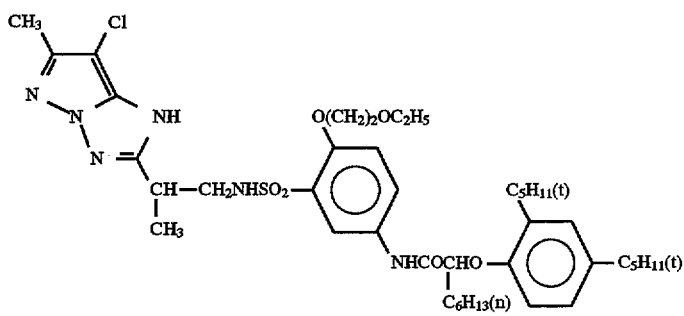
ExM-5

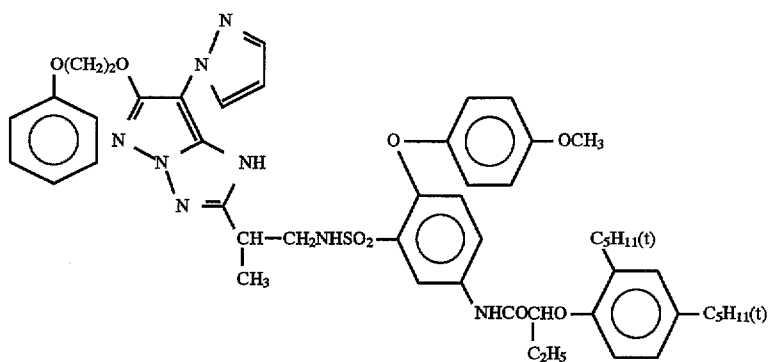
ExM-6
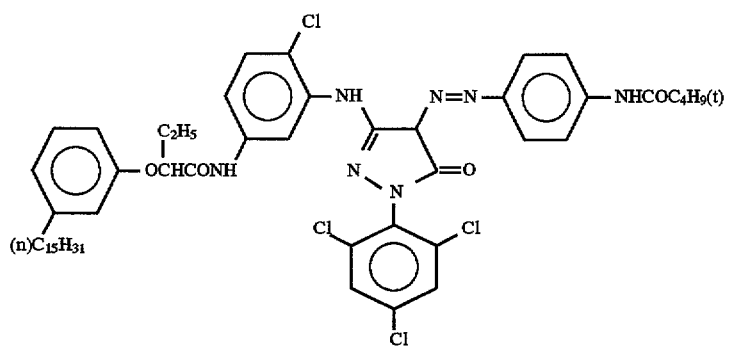
ExM-7
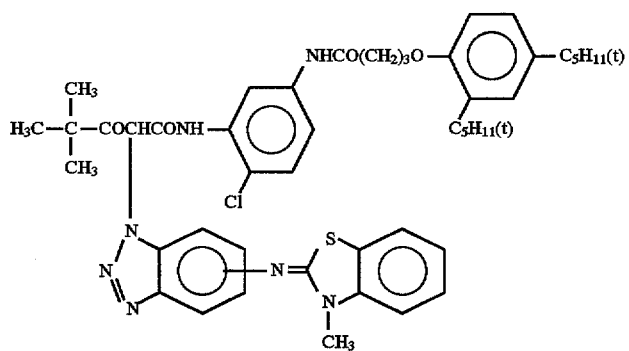
ExY-1
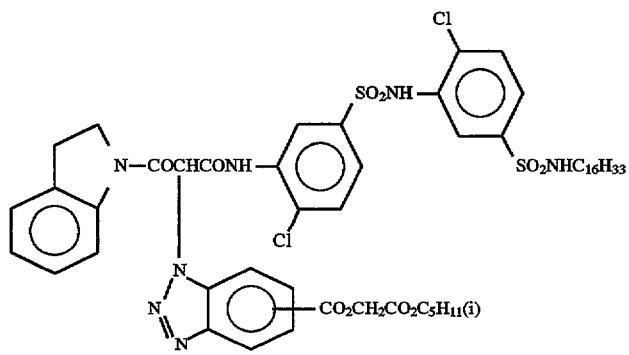
ExY-2

-continued
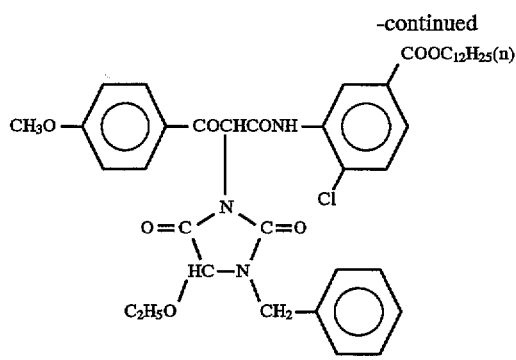
ExY-3
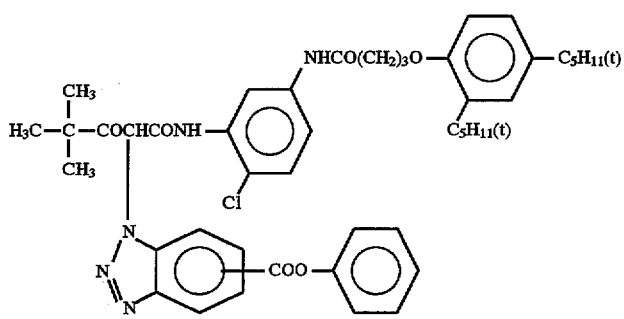
ExY-4
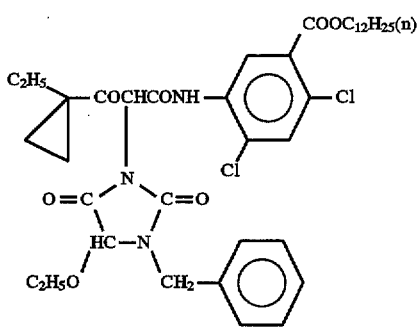
ExY-5
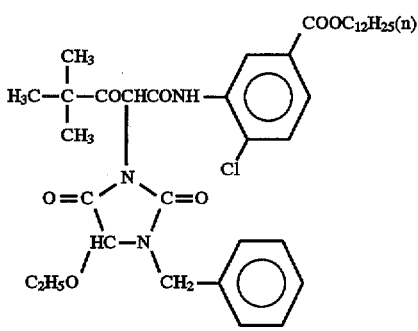
ExY-6
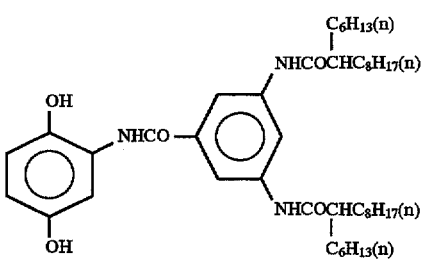
Cpd-1

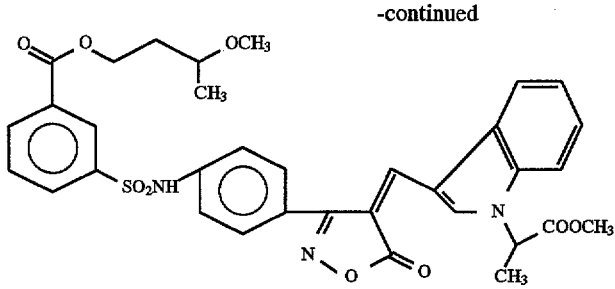 Cpd-2
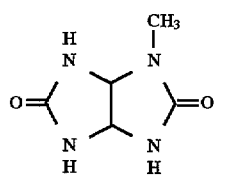 Cpd-3
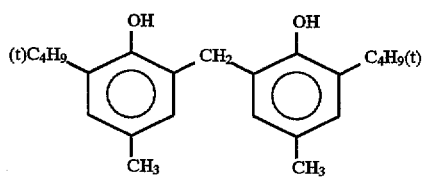 Cpd-4
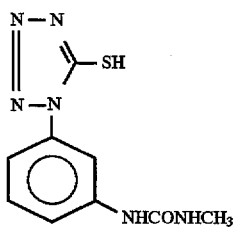 Cpd-5
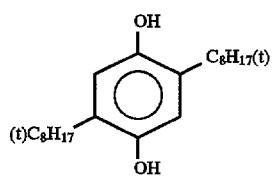 Cpd-6
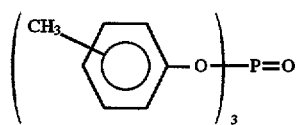 Solv-1
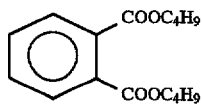 Solv-2
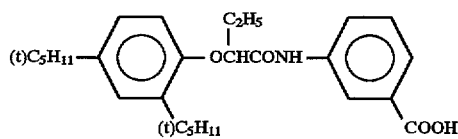 Solv-3
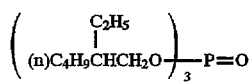 Solv-4

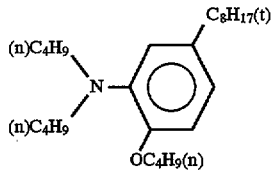
Solv-5
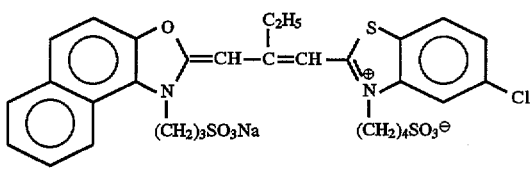
ExS-1
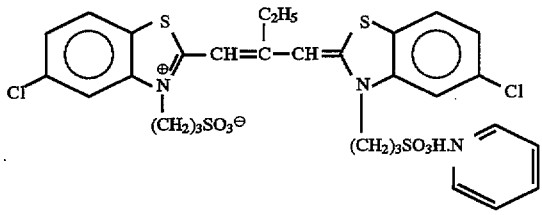
ExS-2
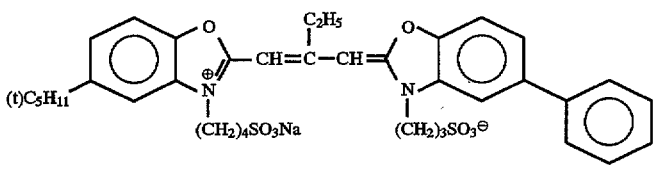
ExS-3
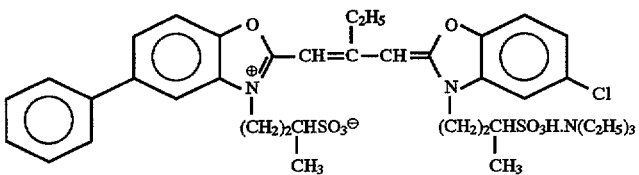
ExS-4
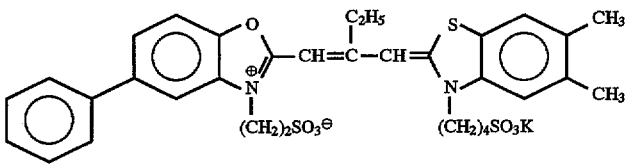
ExS-5
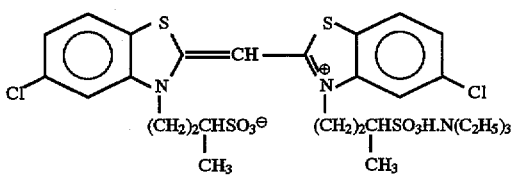
ExS-6
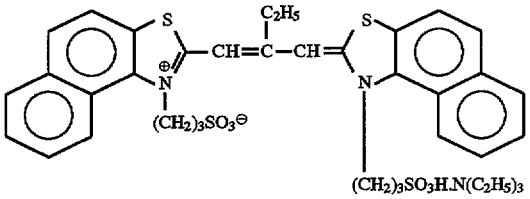
ExS-7
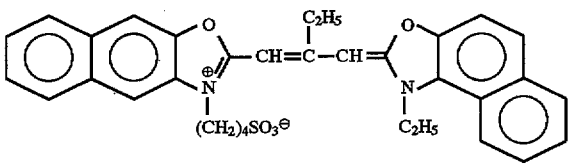
ExS-8

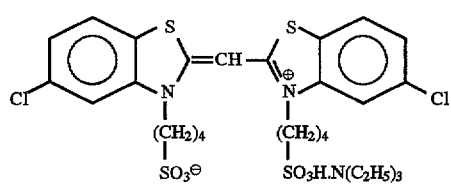 ExS-9
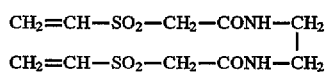 H-1
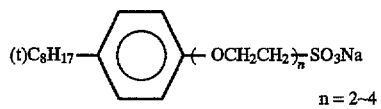 W-1
 W-2
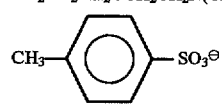 W-3
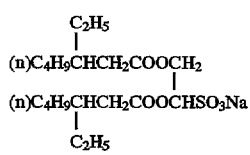 W-4
$C_8F_{17}SO_2N(C_3H_7)CH_2COOK$ W-5
 W-6
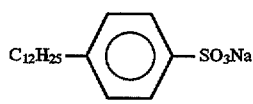
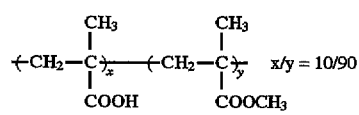 B-1
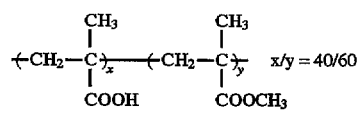 B-2
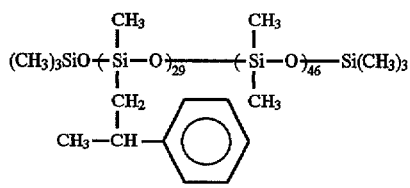 B-3
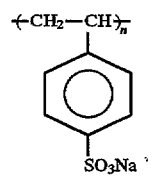 B-4

-continued
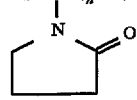 (mol. wt. about 10,000)   B-6
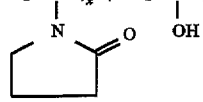 x/y = 70/30   B-6
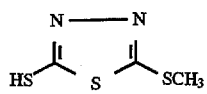   F-1
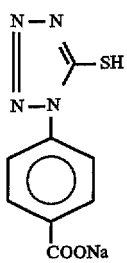   F-2
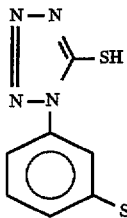   F-3
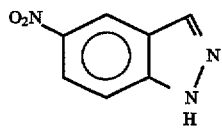   F-4
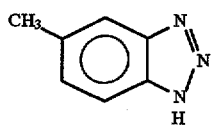   F-5
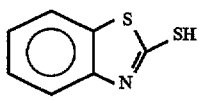   F-6
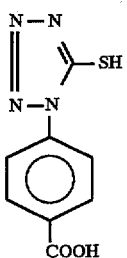   F-7
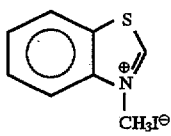   F-8

-continued

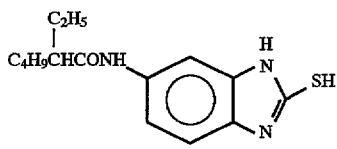 F-9

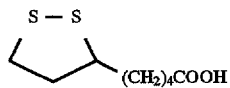 F-10

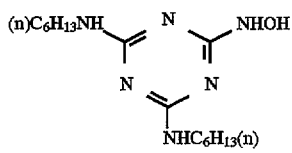 F-11

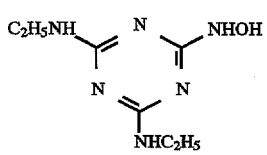 F-12

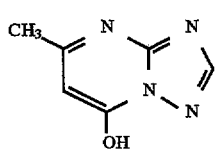 F-13

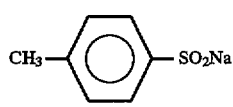 F-14

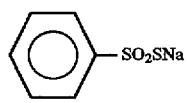 F-15

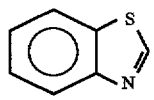 F-16

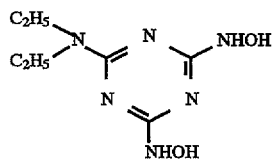 F-17

Compounds represented by formula (I) or comparative compounds were added to the fourth layer of Sample 101 in coemulsified state with the couplers of the fourth layer so as to provide the addition amount of $5\times10^{-2}$ mol per mol of Ag in the fourth layer. Samples 102 to 128 as indicated in Table 2 were prepared in the same manner as the preparation of Sample 101 except for the above. In the case where there are shown two compounds, they were mixed in mol ratio of 1/1 and the total amount was $5\times10^{-2}$ mol per mol of Ag.

The evaluation of the fluctuation of the photographic property after photographing until processing was carried out as follows.

After being subjected to sensitometry exposure, these samples were stored for 3 days under the forced aged conditions of 60° C., 60% RH and 50° C., 80% RH, then color development processed at 38° C. as follows. Densities of the processed samples were measured using a blue filter and a red filter. The difference in sensitivities of these samples and samples immediately development processed after exposure was evaluated.

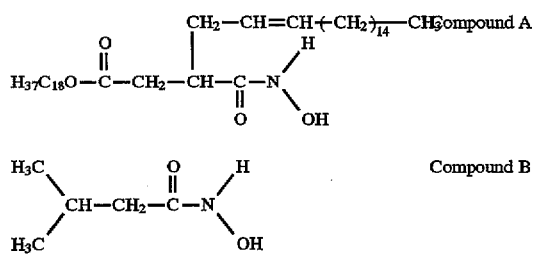

Compound A

Compound B

The compound disclosed in U.S. Pat. No. 4,339,515.

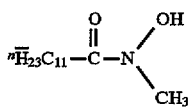
Compound C

Compound 3.8 disclosed in U.S. Pat. No. 4,330,606.

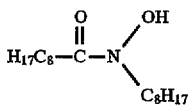
Compound D

The compound disclosed in JP-A-3-293666.

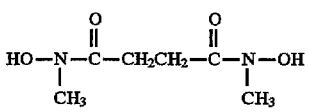
Compound E

The compound disclosed in JP-A-59-198453.

The above color photographic materials were processed, after exposure, according to the following processing step.

Processing Step

| Step | Processing Time | Processing Temperature (°C.) |
|---|---|---|
| Color Development | 3 min 15 sec | 38 |
| Bleaching | 3 min 00 sec | 38 |
| Washing | 30 sec | 24 |
| Fixing | 3 min 00 sec | 38 |
| Washing (1) | 30 sec | 24 |
| Washing (2) | 30 sec | 24 |
| Stabilization | 30 sec | 38 |
| Drying | 4 min 20 sec | 55 |

The composition of each processing solution is as follows.

| | (unit: g) |
|---|---|
| Color Developing Solution | |
| Diethylenetriaminepentaacetic Acid | 1.0 |
| 1-Hydroxyethylidene-1,1-diphosphonic Acid | 3.0 |
| Sodium Sulfite | 4.0 |
| Potassium Carbonate | 30.0 |
| Potassium Bromide | 1.4 |
| Potassium Iodide | 1.5 mg |
| Hydroxylamine Sulfate | 2.4 |
| 4-[N-Ethyl-N-β-hydroxyethylamino]-2-methylaniline Sulfate | 4.5 |
| Water to make | 1.0 l |
| pH | 10.05 |
| Bleaching Solution | |
| Sodium Ethylenediaminetetraacetato Ferrate Trihydrate | 100.0 |
| Disodium Ethylenediaminetetraacetate | 100.0 |
| 3-Mercapto-1,2,4-triazole | 0.03 |
| Ammonium Bromide | 140.0 |
| Ammonium Nitrate | 30.0 |
| Aqueous Ammonia (27%) | 6.5 ml |
| Water to make | 1.0 l |
| pH | 6.0 |
| Fixing Solution | |
| Disodium Ethylenediaminetetraacetate | 0.5 |
| Ammonium Sulfite | 20.0 |
| Aqueous Solution of Ammonium | 295.00 |
| Thiosulfate (700 g/liter) | |
| Acetic Acid (90%) | 3.3 |
| Water to make | 1.0 l |
| pH | 6.7 |
| Stabilizing Solution | |
| p-Nonylphenoxypolyglycidol (average polymerization degree of glycidol: 10) | 0.2 |
| Ethylenediaminetetraacetic Acid | 0.05 |
| 1,2,4-Triazole | 1.3 |
| 1,4-Bis(1,2,4-triazol-1-ylmethyl)-piperazine | 0.75 |
| Hydroxyacetic Acid | 0.02 |
| Hydroxyethyl Cellulose (SP-2000, Daicel Chemical Industries HEC) | 0.1 |
| 1,2-Benzisothiazolin-3-one | 0.05 |
| Water to make | 1.0 l |
| pH | 8.5 |

The logarithmic value of the reciprocal of the exposure amount required to provide an optical density of fog +1.0 was taken as the photographic sensitivity. The fluctuation of the photographic property between the time after photographing until processing was expressed as a relative sensitivity of the sample stored, after exposure, under the forced aged conditions to that of the sample processed immediately after exposure (difference in the logarithmic values). The value nearer to zero means less fluctuation of the photographic property.

The evaluation was carried out for the fluctuation of the photographic property with respect to both of the red-sensitive layer containing the compound of formula (I) and the blue-sensitive layer not containing the compound of formula (I). In the sample containing the compound of formula (I) or the comparative compound, the fluctuation of photographic property of the blue-sensitive layer based on the sample not containing either compound (Sample 101) means the diffusion of the compound from the red-sensitive layer (addition layer) to the blue-sensitive layer (non-addition layer) and is not desired. The results obtained are shown in Table 2.

TABLE 2

| | | Aged Fluctuation of Photographic Property after Photographing until Processing | | | |
|---|---|---|---|---|---|
| | | Red-Sensitive Layer | | Blue-Sensitive Layer | |
| Sample No. | Compound | 60° C., 60% RH | 50° C., 80% RH | 60° C., 60% RH | 50° C., 80% RH |
| 101 (Comparison) | — | 0.20 | −0.02 | −0.02 | −0.03 |
| 102 (Comparison) | A | 0.17 | −0.02 | −0.01 | −0.03 |
| 103 (Comparison) | B | 0.16 | −0.02 | −0.02 | −0.03 |
| 104 (Comparison) | C | 0.14 | −0.02 | −0.03 | −0.09 |
| 105 (Comparison) | D | 0.14 | −0.02 | −0.02 | −0.02 |
| 106 (Comparison) | E | 0.08 | −0.03 | −0.05 | −0.13 |
| 107 (Invention) | 16 | 0.06 | −0.02 | −0.02 | −0.03 |
| 108 (Invention) | 17 | 0.07 | −0.02 | −0.02 | −0.03 |
| 109 (Invention) | 18 | 0.07 | −0.02 | −0.02 | −0.03 |
| 110 (Invention) | 19 | 0.06 | −0.02 | −0.02 | −0.03 |
| 111 (Invention) | 20 | 0.06 | −0.02 | −0.02 | −0.03 |
| 112 (Invention) | 21 | 0.03 | −0.02 | −0.02 | −0.03 |
| 113 (Invention) | 22 | 0.03 | −0.02 | −0.02 | −0.03 |
| 114 (Invention) | 21 and 22 | 0.03 | −0.02 | −0.02 | −0.03 |
| 115 (Invention) | 24 | 0.07 | −0.02 | −0.02 | −0.03 |

TABLE 2-continued

| | | Aged Fluctuation of Photographic Property after Photographing until Processing | | | |
|---|---|---|---|---|---|
| | | Red-Sensitive Layer | | Blue-Sensitive Layer | |
| Sample No. | Compound | 60° C., 60% RH | 50° C., 80% RH | 60° C., 60% RH | 50° C., 80% RH |
| 116 (Invention) | 25 | 0.06 | −0.02 | −0.02 | −0.03 |
| 117 (Invention) | 26 | 0.07 | −0.02 | −0.02 | −0.03 |
| 118 (Invention) | 27 | 0.03 | −0.02 | −0.02 | −0.03 |
| 119 (Invention) | 28 | 0.03 | −0.02 | −0.02 | −0.03 |
| 120 (Invention) | 27 and 28 | 0.03 | −0.02 | −0.02 | −0.03 |
| 121 (Invention) | 30 | 0.06 | −0.02 | −0.02 | −0.03 |
| 122 (Invention) | 1 | 0.03 | −0.02 | −0.02 | −0.03 |
| 123 (Invention) | 2 | 0.03 | −0.02 | −0.02 | −0.03 |
| 124 (Invention) | 3 | 0.03 | −0.02 | −0.02 | −0.03 |
| 125 (Invention) | 4 | 0.03 | −0.02 | −0.02 | −0.03 |
| 126 (Invention) | 43 | 0.07 | −0.02 | −0.02 | −0.03 |
| 127 (Invention) | 44 | 0.08 | −0.02 | −0.02 | −0.03 |
| 128 (Invention) | 47 | 0.07 | −0.02 | −0.02 | −0.03 |

As can be seen from Table 2, in the sample containing the compound represented by formula (I) of the present invention, the layer containing the compound (the red-sensitive layer) underwent less fluctuation of the photographic property with the passage of time after photographing until processing and did not adversely affect the photographic property with the lapse of time of the layer not containing the compound of the present invention (the blue-sensitive layer).

In addition, the compound represented by formula (I) of the present invention does not adversely affect other photographic properties and the storage stability of the layers not containing the compound was not affected.

EXAMPLE 2

Compounds of the present invention other than those indicated in Table 2 in Example 1, that is, Compounds 5 to 15, 23, 29, 31 to 42, 45, 46, 48 to 61 were evaluated similarly. Although they did not reach the same levels with the samples in Example 1, they showed desirable effect to reduce the fluctuation of the photographic property after photographing with the lapse of time.

EXAMPLE 3

When the compound of the present invention was used in a green-sensitive layer or a blue-sensitive layer, the storage stability of the layer containing the compound was improved similarly in Example 1, and did not affect the layer not containing the compound.

EXAMPLE 4

Sample 201 shown below was prepared instead of Sample 101 of Example 1. Samples 202 to 228 were prepared according to the method of preparing Sample 201 except that compounds represented by formula (I) or comparative compounds were added to the fourth layer of Sample 201 so that the compounds were coemulsified with the couplers of this layer and the amount became 5×10⁻² mol per mol of the Ag in this layer. Further, where two compounds are indicated, they were mixed in mol ratio of 1/1 so that the total mol number became 5×10⁻² mol per mol of the Ag. Evaluation of the compounds of the present invention was conducted using these samples, they showed desirable performance similarly as in Example 1.

1) Support

The support which was used in Example 4 was prepared as follows.

100 weight parts of commercially available polyethylene-2,6-naphthalate polymer and 2 weight parts of Tinuvin P. 326 (product of Ciba-Geigy), as an ultraviolet absorber, were dried in a usual method, then melted at 300° C., subsequently, extruded through a T-type die, and stretched 3.0 times in a lengthwise direction at 140° C. and then 3.0 times in a width direction at 130° C., and further fixed for 6 seconds at 250° C. and PEN film having a thickness of 90 μm was obtained.

Further, a part of the film was wound on to a stainless steel spool having a diameter of 20 cm and provided heat history at 110° C. for 48 hours.

2) Coating of a subbing layer

A coating solution for a subbing layer having the following composition was coated on each side of the above support after both surfaces of which were corona discharged, UV discharged, and further glow discharged and flame discharged. The subbing layer was provided on the hotter side at the time of stretching. The corona discharge treatment was carried out using solid state corona processor model 6 KVA available from Pillar Co. which can treat the support of 30 cm wide at a rate of 20 m/min. At that time, the treatment of 0.375 KV·A·min/m² was conducted to the support from the reading of the electric current and voltage. The discharge frequency at the treatment time was 9.6 KHz, gap clearance between the electrode and the induction roll was 1.6 mm. UV discharge treatment was conducted heating at 75° C. Further, glow discharge treatment was conducted at 3,000 W for 30 second irradiation using a cylindrical electrode.

| | |
|---|---|
| Gelatin | 3 g |
| Distilled Water | 25 ml |
| Sodium-α-sulfodi-2-ethylhexyl-succinate | 0.07 g |
| Formaldehyde | 0.02 g |
| Salicylic Acid | 0.1 g |
| Diacetyl Cellulose | 0.5 g |
| p-Chlorophenol | 0.5 g |
| Resorcin | 0.5 g |
| Cresol | 0.5 g |
| (CH₂=CHSO₂CH₂CH₂NHCO)₂CH₂ | 0.02 g |
| Trimethylolpropane addition product of 3 time mol of aziridine | 0.02 g |
| Trimethylolpropane addition product of 3 time mol of toluenediisocyanate | 0.02 g |
| Methanol | 15 ml |
| Acetone | 85 ml |
| Formaldehyde | 0.01 g |
| Acetic Acid | 0.01 g |
| Concentrated Hydrochloric Acid | 0.01 g |

3) Coating of a backing layer

An antistatic layer, a magnetic recording layer and a sliding layer each having the following composition were coated as backing layers on one side of the above undercoated support.

3-1) Coating of an antistatic layer 3-1-1) Preparation of electrically conductive fine grain dispersion solution (a composite dispersion solution of stannic oxide-antimony oxide)

230 weight parts of stannic chloride hydrate and 23 weight parts of antimony trichloride were dissolved in 3,000 weight parts of ethanol and homogeneous solution was obtained. A 1N aqueous sodium hydroxide solution was dropwise added to the above solution until the pH of the solution reached 3, thereby the coprecipitate of colloidal stannic oxide and antimony oxide was obtained. The thus-obtained coprecipitate was allowed to stand at 50° C. for 24 hours and red brown colloidal precipitate was obtained.

The red brown colloidal precipitate was isolated by a centrifugal separator. Water was added to the precipitate and washed by centrifugation to remove excessive ion. The excessive ion was removed by repeating this operation three times.

200 weight parts of the colloidal precipitate from which the excessive ion was removed was again dispersed in 1,500 weight parts of water, atomized in a kiln heated to 650° C., thereby a bluish fine grain powder of a composite of stannic oxide-antimony oxide having an average grain size of 0.005 μm was obtained. The resistivity of this fine grain powder was 5 Ω·cm.

The pH of the mixed solution comprising 40 weight parts of the above fine grain powder and 60 weight parts of water was adjusted to 7.0. This mixed solution was dispersed coarsely by a disperser, then dispersed using a horizontal sand mill (Dyno Mill, manufactured by WILLYA. BACHOFENAG) until the residence time reached 30 minutes, thus the objective product was prepared. The average grain size of the secondary agglomerate at that time was about 0.04 μm.

3-1-2) Coating of an electrically conductive layer

An electrically conductive layer having the formulation shown below was coated so as to provide a dry film thickness of 0.2 μm and dried at 115° C. for 60 seconds.

| | |
|---|---|
| Electrically Conductive Fine Grain Dispersion Solution Prepared in 3-1-1) | 20 weight parts |
| Gelatin | 2 weight part |
| Water | 27 weight parts |
| Methanol | 60 weight parts |
| p-Chlorophenol | 0.5 weight parts |
| Resorcin | 2 weight parts |
| Polyoxyethylenenonylphenyl Ether | 0.01 weight parts |

The resistance of the thus obtained electrically conductive film was $10^{8.0}$ (100 V), which had an excellent antistatic performance.

3-2) Coating of a magnetic recording layer 220 g of water and 150 g of silane coupling agent of poly(polymerization degree: 16)oxyethylenepropyl trimethoxysilane were added to 1,100 g of magnetic substance Co-adhered γ-$Fe_2O_3$ (acicular, major axis: 0.14 μm, minor axis: 0.03 μm, specific surface area: 41 $m^2$/g, saturation magnetization: 89 emu/g, the surface comprised aluminum oxide and silicon oxide and each was surface treated with 2 wt % of $Fe_2O_3$ coercive force: 930 Oe, $Fe^{+2}/Fe^{+3}$ ratio: 6/94) and they were well kneaded in an open kneader for 3 hours. The thus coarsely dispersed viscous liquid was dried at 70° C. for a whole day and night and, after removal of water, heated at 110° C. for 1 hour and the surface-treated magnetic grains were obtained.

The above grains were kneaded again in an open kneader according to the following formulation.

| | |
|---|---|
| The Above Surface-Treated Magnetic Grains | 1,000 g |
| Diacetyl Cellulose | 17 g |
| Methyl Ethyl Ketone | 100 g |
| Cyclohexanone | 100 g |

The above product was finely dispersed using a sand mill (¼G) at 200 rpm for 4 hours according to the following formulation.

| | |
|---|---|
| The Above Kneaded Product | 100 g |
| Diacetyl Cellulose | 60 g |
| Methyl Ethyl Ketone | 300 g |
| Cyclohexanone | 300 g |

Further, diacetyl cellulose and trimethylolpropane addition product of 3 time mol of toluenediisocyanate as a hardening agent were added in the amount of 20 wt % based on the binder. The product was diluted with an equal amount of methyl ethyl ketone and cyclohexanone so as to obtain the solution having the viscosity of 80 cp. The solution was coated on the above electrically conductive layer with a bar coater to provide a film thickness of 1.2 μm. The amount of the magnetic substance was 0.6 g/$m^2$. Silica grains (0.3 μm) and abrasive aluminum oxide (0.5 μm) were added as a matting agent each in an amount of 10 mg/$m^2$. Drying was conducted at 15° C. for 6 minutes (the rollers in the drying zone and transporting devices were all set at 115° C.).

When using a blue filter at the status M of an X-light, the increment of color density of $D^B$ of the magnetic recording layer was about 0.1. The saturation magnetization moment of the magnetic recording layer was 4.2 emu/$m^2$, coercive force was 923 Oe, and angular ratio was 65%.

3-3) Preparation of a sliding layer

The coating solution of the following formulation was coated in the solid coating amount of the compound shown below and dried at 110° C. for 5 minutes to obtain a sliding layer.

| | |
|---|---|
| Diacetyl Cellulose | 25 mg/$m^2$ |
| $C_6H_{13}CH(OH)C_{10}H_{20}COOC_{40}H_{81}$ (Compound a) | 6 mg/$m^2$ |
| $C_{50}H_{101}O(CH_2CH_2O)_{16}H$ (Compound b) | 9 mg/$m^2$ |

Moreover, Compound a/Compound b (6/9) were heated at 105° C. and dissolved in a solvent of xylene and propyleneglycol monomethyl ether (volume ratio: 1/1), and this solution was poured to propyleneglycol monomethyl ether (25° C.) of 10 times the volume and finely dispersed. This fine dispersion solution was further diluted with acetone of 5 times the volume, again dispersed using a high pressure homogenizer (200 atm) and the thus-obtained dispersion (average grain size: 0.01 μm) was added.

The sliding layer obtained had excellent characteristics such as a dynamic friction coefficient of 0.06 (stainless steel ball of 5 mmφ, load: 100 g, speed: 6 cm/min) and a static friction coefficient of 0.07 (by a clip method). The sliding characteristic with the emulsion surface described below showed a dynamic friction coefficient of 0.12.

4) Coating of a photographic material

Each layer having the following composition was multilayer coated on the opposite side of the backing layer obtained above, thus a color negative film was prepared. This was designated as Sample 201.

The main components for use in each layer are classified as follows:

ExC: Cyan Coupler
ExM: Magenta Coupler
ExY: Yellow Coupler
ExS: Sensitizing Dye
UV: Ultraviolet Absorbing Agent
HBS: High Boiling Point Organic Solvent
H: Hardening Agent for Gelatin The numeral corresponding to each component indicates the coated weight in unit of g/$m^2$, and the coated weight of silver halide is shown as the calculated weight of silver. Further, in the case of a sensitizing dye, the coated weight is indicated in unit of mol per mol of the silver halide in the same layer.

Sample 201

| First Layer: Antihalation Layer | |
|---|---|
| Black Colloidal Silver | 0.09 as silver |
| Gelatin | 1.60 |
| ExM-1 | 0.12 |
| ExF-1 | $2.0 \times 10^{-3}$ |
| Solid Dispersion Dye ExF-2 | 0.03 |
| Solid Dispersion Dye ExF-3 | 0.040 |
| HBS-1 | 0.15 |
| HBS-2 | 0.02 |
| Second Layer: Interlayer | |
| Silver Iodobromide Emulsion M | 0.065 as silver |
| ExC-2 | 0.04 |
| Polyethyl Acrylate Latex | 0.20 |
| Gelatin | 1.04 |
| Third Layer: Low Sensitivity Red-Sensitive Emulsion Layer | |
| Silver Iodobromide Emulsion A | 0.25 as silver |
| Silver Iodobromide Emulsion B | 0.25 as silver |
| ExS-1 | $6.9 \times 10^{-5}$ |
| ExS-2 | $1.8 \times 10^{-5}$ |
| ExS-3 | $3.1 \times 10^{-4}$ |
| ExC-1 | 0.17 |
| ExC-3 | 0.030 |
| ExC-4 | 0.10 |
| ExC-5 | 0.020 |
| ExC-6 | 0.010 |
| Cpd-2 | 0.025 |
| HBS-1 | 0.10 |
| Gelatin | 0.87 |
| Fourth Layer: Middle Sensitivity Red-Sensitive Emulsion Layer | |
| Silver Iodobromide Emulsion C | 0.70 as silver |
| ExS-1 | $3.5 \times 10^{-4}$ |
| ExS-2 | $1.6 \times 10^{-5}$ |
| ExS-3 | $5.1 \times 10^{-4}$ |
| ExC-1 | 0.13 |
| ExC-2 | 0.060 |
| ExC-3 | 0.0070 |
| ExC-4 | 0.090 |
| ExC-5 | 0.015 |
| ExC-6 | 0.0070 |
| Cpd-2 | 0.023 |
| HBS-1 | 0.10 |
| Gelatin | 0.75 |
| Fifth Layer: High Sensitivity Red-Sensitive Emulsion Layer | |
| Silver Iodobromide Emulsion D | 1.40 as silver |
| ExS-1 | $2.4 \times 10^{-4}$ |
| ExS-2 | $1.0 \times 10^{-4}$ |
| ExS-3 | $3.4 \times 10^{-4}$ |
| ExC-1 | 0.10 |
| ExC-3 | 0.045 |
| ExC-6 | 0.020 |
| ExC-7 | 0.010 |
| Cpd-2 | 0.050 |
| HBS-1 | 0.22 |
| HBS-2 | 0.50 |
| Gelatin | 1.10 |
| Sixth Layer: Interlayer | |
| Cpd-1 | 0.090 |
| Solid Dispersion Dye ExF-4 | 0.030 |
| HBS-1 | 0.050 |
| Polyethyl Acrylate Latex | 0.15 |
| Gelatin | 1.10 |
| Seventh Layer: Low Sensitivity Green-Sensitive Emulsion Layer | |
| Silver Iodobromide Emulsion E | 0.15 as silver |
| Silver Iodobromide Emulsion F | 0.10 as silver |
| Silver Iodobromide Emulsion G | 0.10 as silver |
| ExS-4 | $3.0 \times 10^{-5}$ |
| ExS-5 | $2.1 \times 10^{-4}$ |
| ExS-6 | $8.0 \times 10^{-4}$ |
| ExM-2 | 0.33 |
| ExM-3 | 0.086 |
| ExY-1 | 0.015 |
| HBS-1 | 0.30 |
| HBS-3 | 0.010 |
| Gelatin | 0.73 |
| Eighth Layer: Middle Sensitivity Green-Sensitive Emulsion Layer | |
| Silver Iodobromide Emulsion H | 0.80 as silver |
| ExS-4 | $3.2 \times 10^{-5}$ |
| ExS-5 | $2.2 \times 10^{-4}$ |
| ExS-6 | $8.4 \times 10^{-4}$ |
| ExC-8 | 0.010 |
| ExM-2 | 0.10 |
| ExM-3 | 0.025 |
| ExY-1 | 0.018 |
| ExY-4 | 0.010 |
| ExY-5 | 0.040 |
| HBS-1 | 0.13 |
| HBS-3 | $4.0 \times 10^{-3}$ |
| Gelatin | 0.80 |
| Ninth Layer: High Sensitivity Green-Sensitive Emulsion Layer | |
| Silver Iodobromide Emulsion I | 1.25 as silver |
| ExS-4 | $3.7 \times 10^{-5}$ |
| ExS-5 | $8.1 \times 10^{-5}$ |
| ExS-6 | $3.2 \times 10^{-4}$ |
| ExC-1 | 0.005 |
| ExC-6 | 0.005 |
| ExM-1 | 0.020 |
| ExM-4 | 0.025 |
| ExM-5 | 0.040 |
| Cpd-3 | 0.040 |
| HBS-1 | 0.25 |
| Polyethyl Acrylate Latex | 0.15 |
| Gelatin | 1.33 |
| Tenth Layer: Yellow Filter Layer | |
| Yellow Colloidal Silver | 0.015 as silver |
| Cpd-1 | 0.16 |
| Solid Dispersion Dye ExF-5 | 0.060 |
| Solid Dispersion Dye ExF-6 | 0.060 |
| Oil-Soluble Dye ExF-7 | 0.010 |
| HBS-1 | 0.60 |
| Gelatin | 0.60 |
| Eleventh Layer: Low Sensitivity Blue-Sensitive Emulsion Layer | |
| Silver Iodobromide Emulsion J | 0.09 as silver |
| Silver Iodobromide Emulsion K | 0.09 as silver |
| ExS-7 | $8.6 \times 10^{-4}$ |
| ExC-8 | $7.0 \times 10^{-3}$ |
| ExY-1 | 0.050 |
| ExY-2 | 0.22 |
| ExY-3 | 0.50 |
| ExY-4 | 0.020 |
| Cpd-2 | 0.10 |
| Cpd-3 | $4.0 \times 10^{-3}$ |
| HBS-1 | 0.28 |
| Gelatin | 1.20 |
| Twelfth Layer: High Sensitivity Blue-Sensitive Emulsion Layer | |
| Silver Iodobromide Emulsion L | 1.00 as silver |
| ExS-7 | $4.0 \times 10^{-4}$ |
| ExY-2 | 0.10 |
| ExY-3 | 0.10 |
| ExY-4 | 0.010 |
| Cpd-2 | 0.10 |
| Cpd-3 | $1.0 \times 10^{-3}$ |
| HBS-1 | 0.070 |
| Gelatin | 0.70 |
| Thirteenth Layer: First Protective Layer | |
| UV-1 | 0.19 |
| UV-2 | 0.075 |
| UV-3 | 0.065 |
| HBS-1 | $5.0 \times 10^{-2}$ |
| HBS-4 | $5.0 \times 10^{-2}$ |
| ExF-8 | $2.1 \times 10^{-3}$ |

-continued

| | |
|---|---|
| ExF-9 | $6.3 \times 10^{-3}$ |
| Gelatin | 1.8 |
| Fourteenth Layer: Second Protective Layer | |
| Silver Iodobromide Emulsion M | 0.10 as silver |
| H-1 | 0.40 |
| B-1 (diameter: 1.7 μm) | $5.0 \times 10^{-2}$ |
| B-2 (diameter: 1.7 μm) | 0.15 |
| B-3 | 0.05 |
| S-1 | 0.20 |
| Gelatin | 70 |

Further, W-1 to W-3, B-4 to B-6, F-1 to F-17, and iron salts, lead salts, gold salts, platinum salts, palladium salts, iridium salts and rhodium salts were appropriately included in each layer to improve storage stability, processing property, pressure resistance, fungicidal and biocidal properties, antistatic property and coating property.

vibrating ball mill which was used was BO type ball mill manufactured by Chuo Koki. The content was taken out after dispersion and added to 8 g of a 12.5% aqueous gelatin solution and the beads was removed by filtration and the gelatin dispersion of the dye was obtained. The average grain size of fine grains of the dye was 0.44 μm.

Solid dispersions of ExF-3, ExF-4 and ExF-6 were obtained in the same manner. The average grain size of fine grains of the dye were 0.24 μm, 0.45 μm and 0.52 μm, respectively. ExF-5 was dispersed according to the micro-precipitation dispersion method disclosed in Example 1 of EP 549489A. The average grain size was 0.06 μm.

TABLE 3

| Emulsion | Average AgI Content (%) | Variation Coefficient of the AgI Content among Grains (%) | Average Diameter Corresponding to a Sphere (μm) | Variation Coefficient of the Grain Size (%) | Projected Area Diameter Corresponding to a Circle (μm) | Diameter/ Thickness Ratio |
|---|---|---|---|---|---|---|
| A | 1.7 | 10 | 0.46 | 15 | 0.56 | 5.5 |
| B | 3.5 | 15 | 0.57 | 20 | 0.78 | 4.0 |
| C | 8.9 | 25 | 0.66 | 25 | 0.87 | 5.8 |
| D | 8.9 | 18 | 0.84 | 26 | 1.03 | 3.7 |
| E | 1.7 | 10 | 0.46 | 15 | 0.56 | 5.5 |
| F | 3.5 | 15 | 0.57 | 20 | 0.78 | 4.0 |
| G | 8.8 | 25 | 0.61 | 23 | 0.77 | 4.4 |
| H | 8.8 | 25 | 0.61 | 23 | 0.77 | 4.4 |
| I | 8.9 | 18 | 0.84 | 26 | 1.03 | 3.7 |
| J | 1.7 | 10 | 0.46 | 15 | 0.50 | 4.2 |
| K | 8.8 | 18 | 0.64 | 23 | 0.85 | 5.2 |
| L | 14.0 | 25 | 1.28 | 26 | 1.46 | 3.5 |
| M | 1.0 | — | 0.07 | 15 | — | 1 |

In Table 3:
(1) Emulsions J, K and L were reduction sensitized at the preparation of the grains using thiourea dioxide and thiosulfonic acid according to the examples of JP-A-2-191938.
(2) Emulsions A to I were gold, sulfur, and selenium sensitized, respectively, in the presence of the spectral sensitizing dyes which are described at each light-sensitive layer and sodium thiocyanate according to the examples of JP-A-3-237450.
(3) Low molecular weight gelatin was used in the preparation of the tabular grains according to the examples of JP-A-1-158426.
(4) There were observed, using a high pressure electron microscope, such dislocation lines as disclosed in JP-A-3-237450 in tabular grains.
(5) Emulsion L comprised double structure grains containing an internal high iodide core as disclosed in JP-A-60-143331.

Preparation of Organic Solid Dispersion of Dye

The ExF-2 shown below was dispersed according to the following method. That is, 21.7 ml of water, 3 ml of a 5% aqueous solution of sodium p-octylphenoxyethoxyethoxyethanesulfonate, and 0.5 g of a 5% aqueous solution of p-octylphenoxypolyoxyethylene ether (polymerization degree: 10) were placed in a pot mill having a capacity of 700 ml, and 5.0 g of Dye ExF-2 and 500 ml of zirconium oxide beads (diameter: 1 mm) were added thereto and the content was dispersed for 2 hours. The

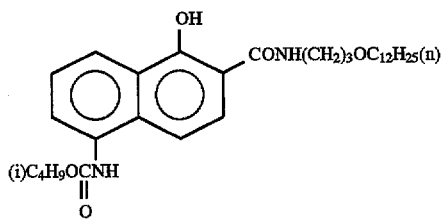 ExC-1
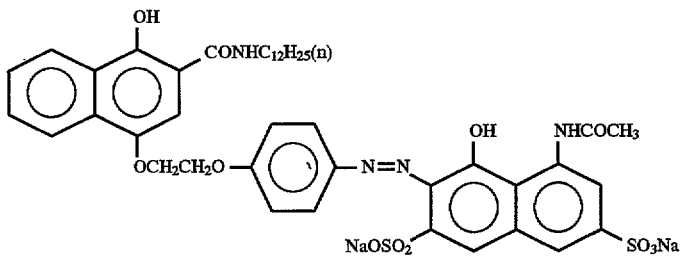 ExC-2
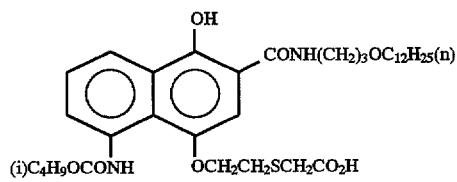 ExC-3
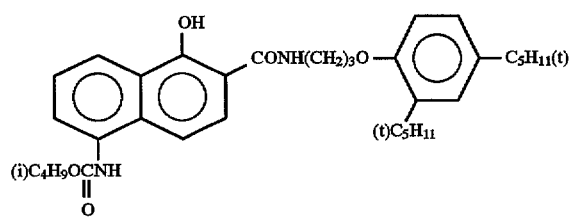 ExC-4
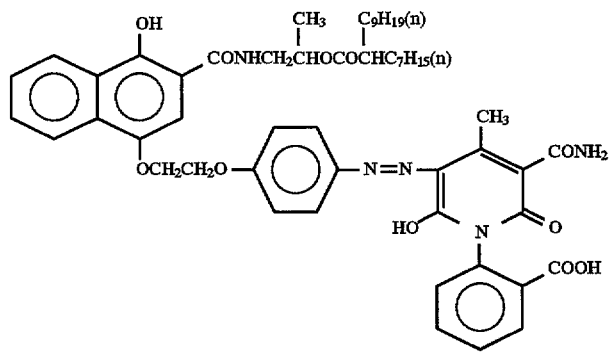 ExC-5
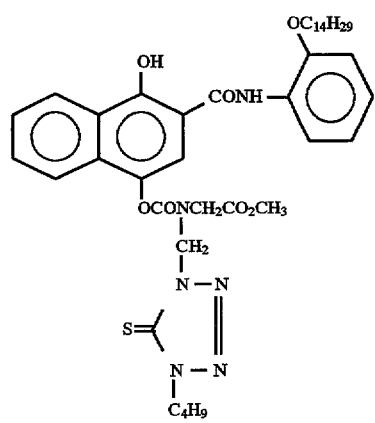 ExC-6

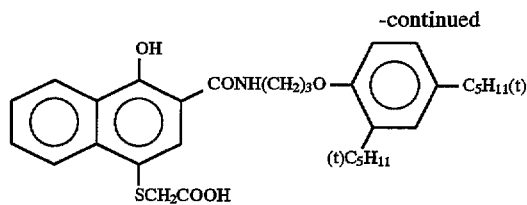
ExC-7
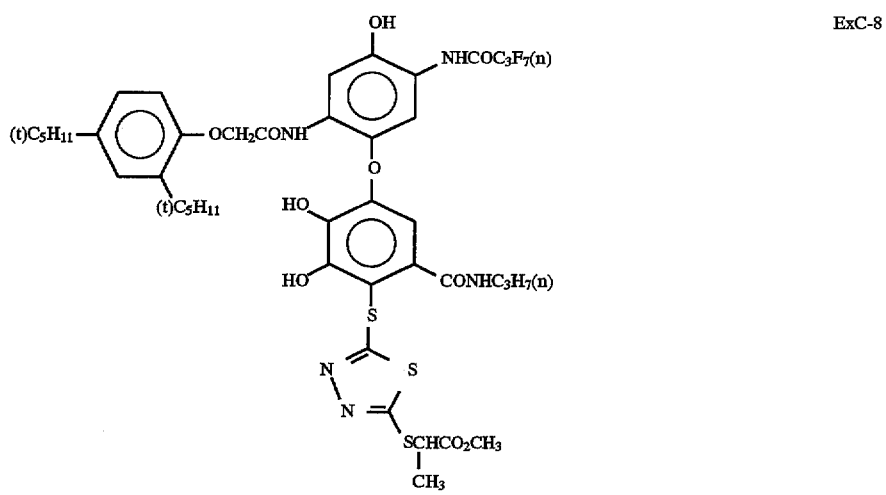
ExC-8
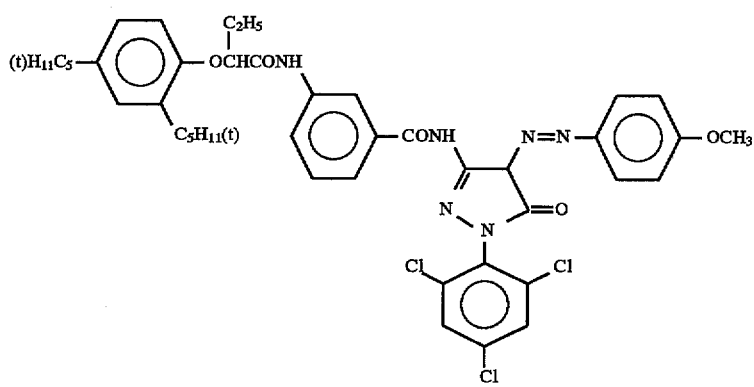
ExM-1
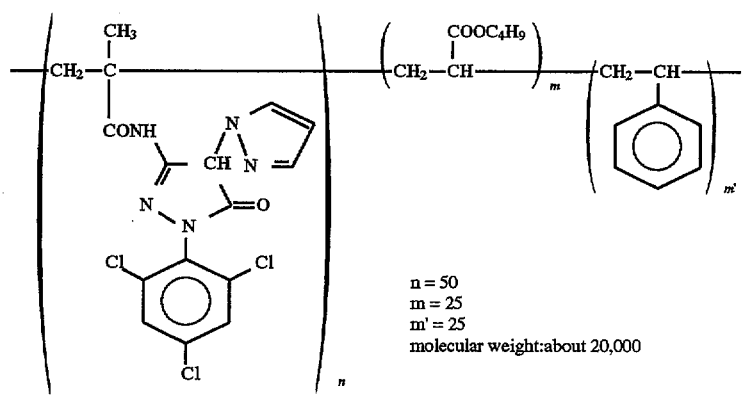
ExM-2
n = 50
m = 25
m' = 25
molecular weight: about 20,000

ExM-3
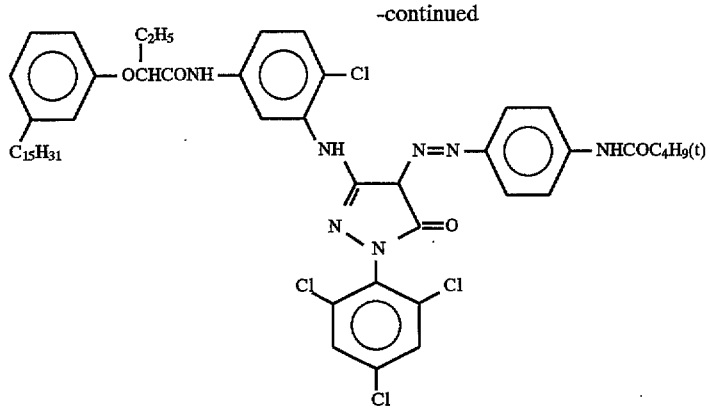
ExM-4
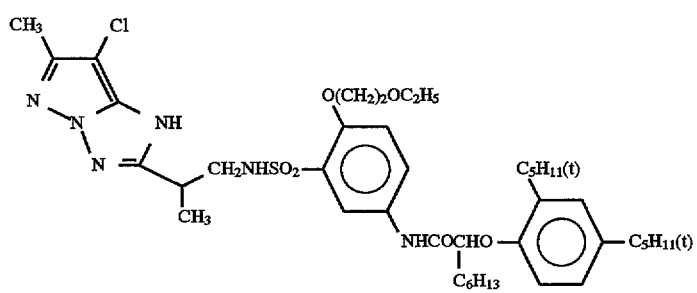
ExM-5
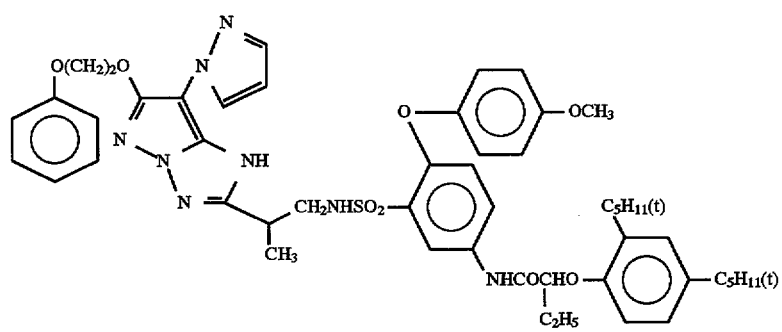
ExY-1
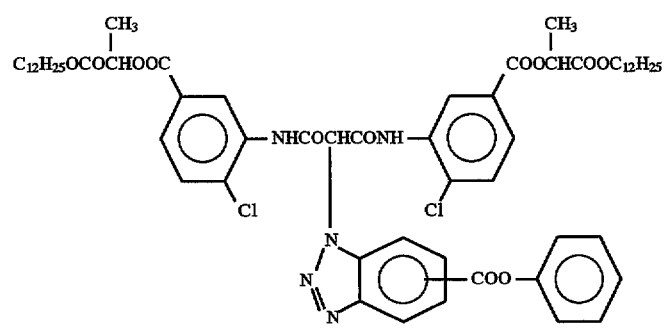
ExY-2
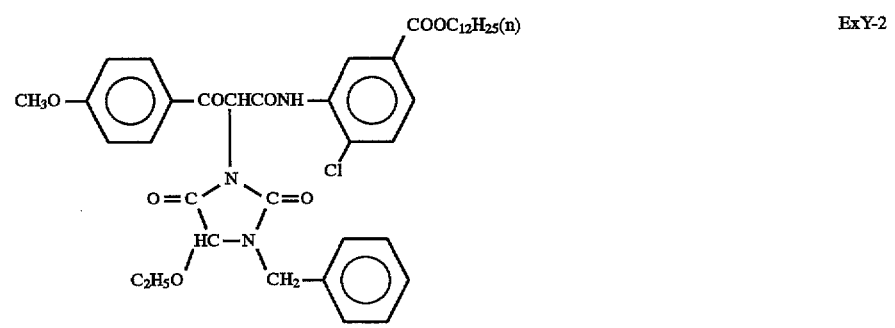

-continued
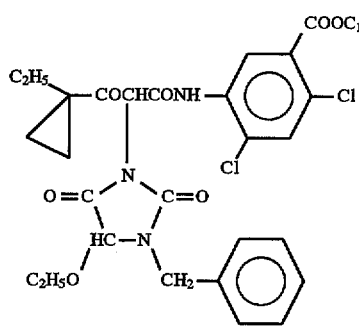
ExY-3
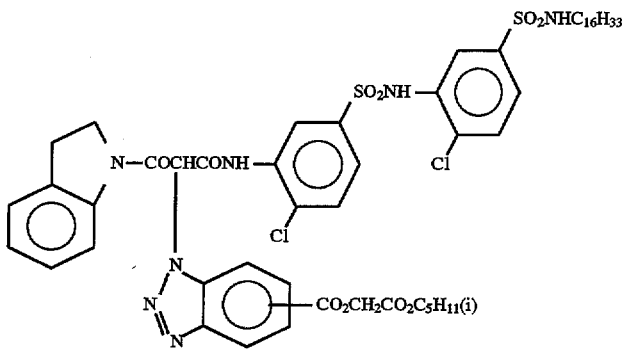
ExY-4
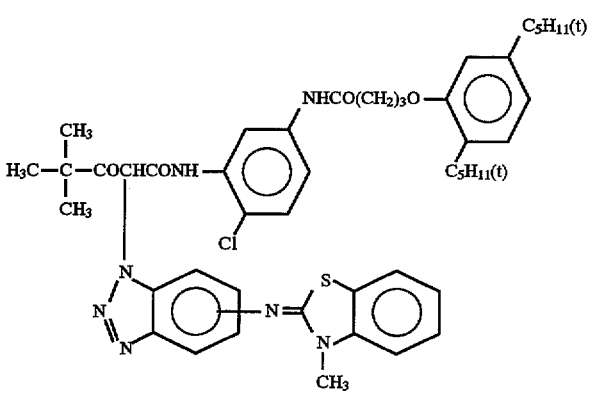
ExY-5
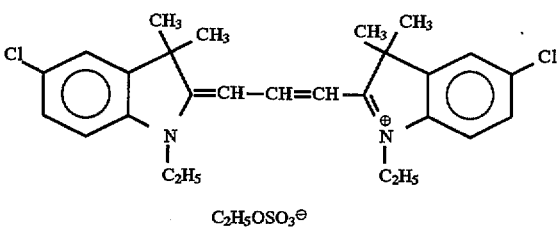
ExF-1
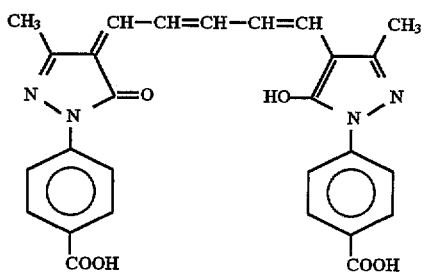
ExF-2

-continued
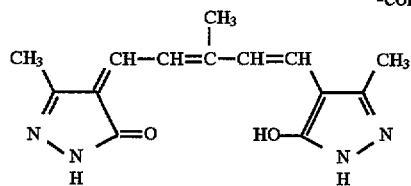 ExF-3
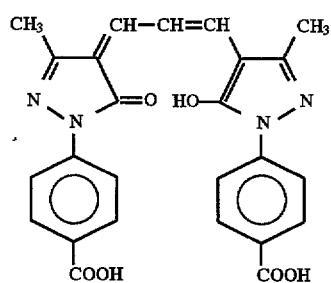 ExF-4
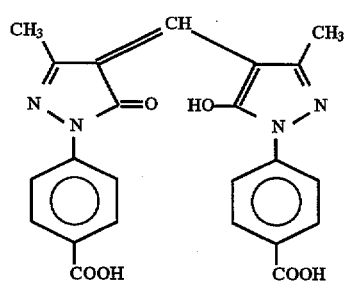 ExF-5
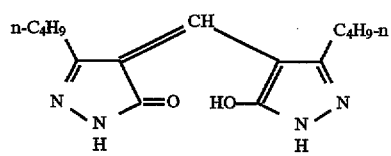 ExF-6
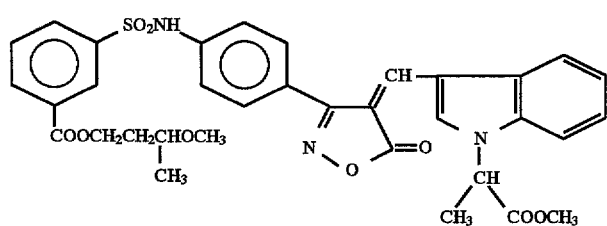 ExF-7
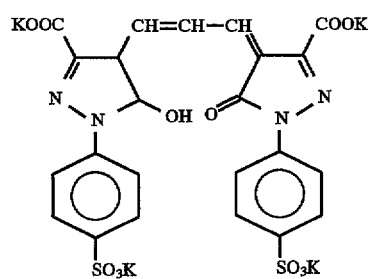 ExF-8
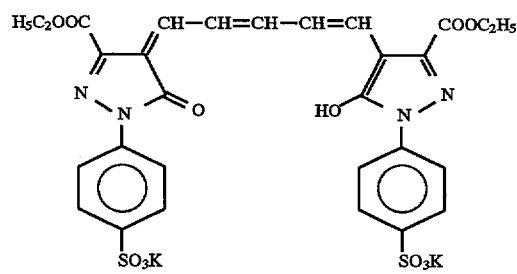 ExF-9

-continued
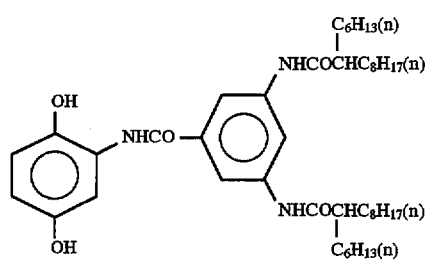 Cpd-1
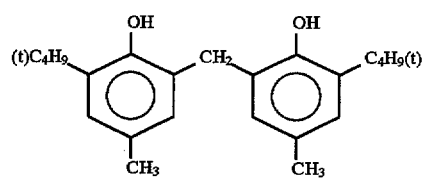 Cpd-2
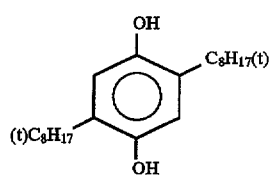 Cpd-3
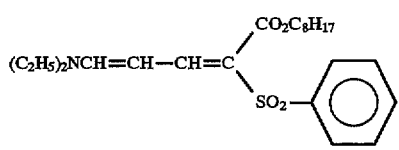 UV-1
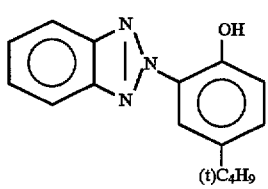 UV-2
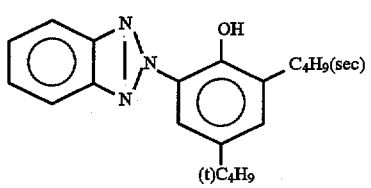 UV-3
Tricresyl phosphate     HBS-1
Di-n-butyl phthalate     HBS-2
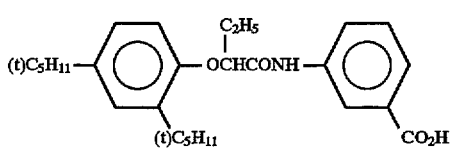 HBS-3
Tri(2-ethylhexyl) Phosphate     HBS-4
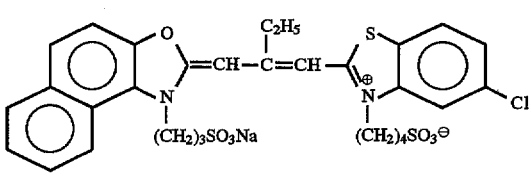 ExS-1

-continued
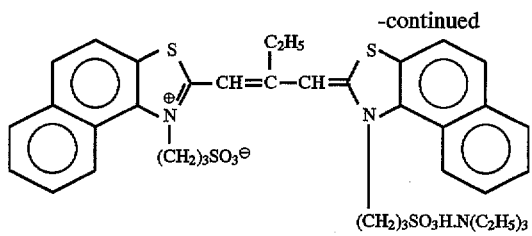 ExS-2
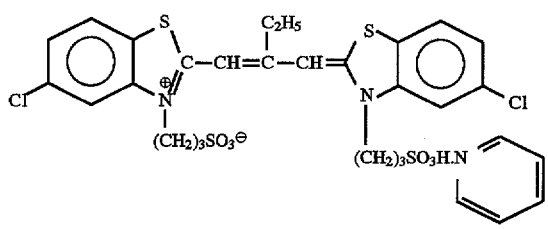 ExS-3
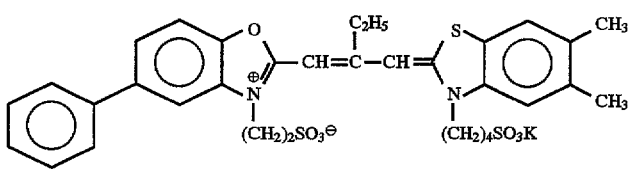 ExS-4
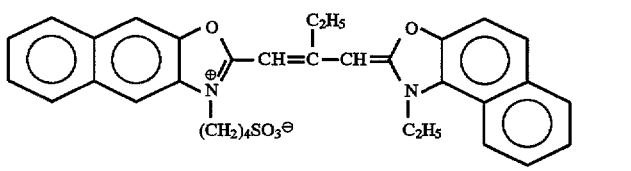 ExS-5
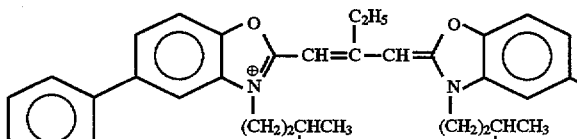 ExS-6
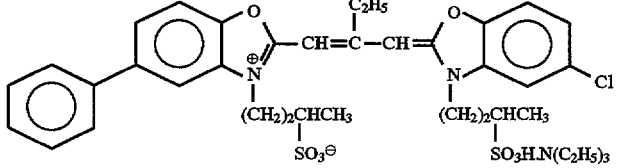 ExS-7
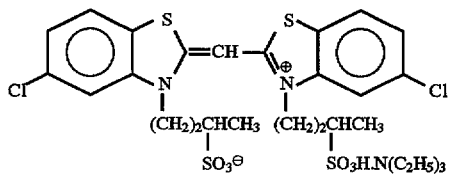 S-1
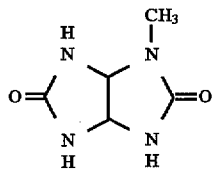 H-1
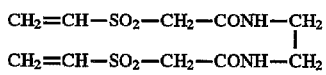 B-1
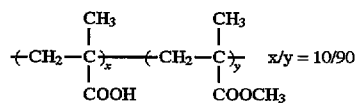 B-2

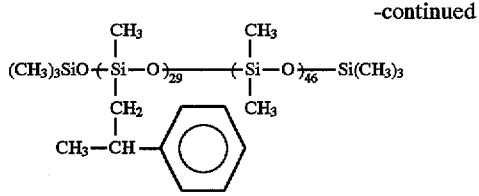 B-3
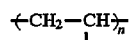 B-4
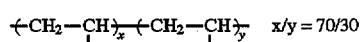 x/y = 70/30  B-5
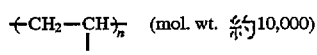 (mol. wt. 約10,000)  B-6
$C_8F_{17}SO_2NHCH_2CH_2CH_2OCH_2CH_2\overset{\oplus}{N}(CH_3)_3$  W-1
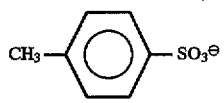 n = 2~4  W-2
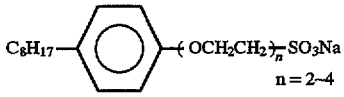 W-3
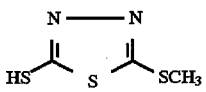 F-1
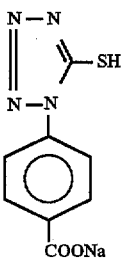 F-2
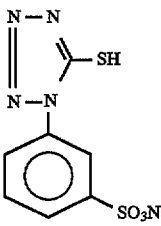 F-3

-continued
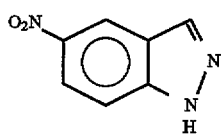
F-4
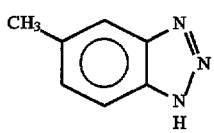
F-5
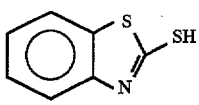
F-6
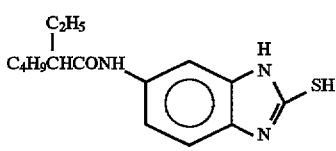
F-7
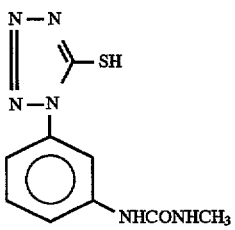
F-8
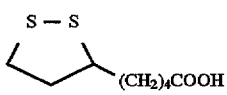
F-9
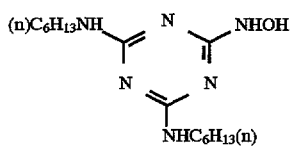
F-10
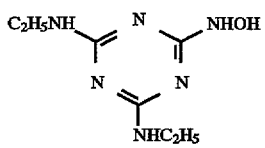
F-11
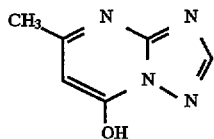
F-12
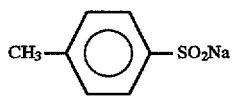
F-13
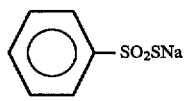
F-14

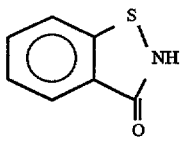

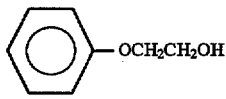

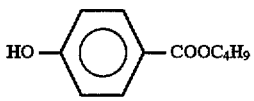

F-15

F-16

F-17

EXAMPLE 5

A sample was prepared by adding Compounds 4, 27 and 28 of the present invention respectively to the fourth, fifth and sixth layers of Sample 101 in Example 1 of JP-A-6-118533 in an amount of $5 \times 10^{-2}$ mol per mol of Ag. After exposure, this sample was put under the forced aged conditions of 50° C., 60% RH for seven days. The sample was after then subjected to the color reversal process disclosed on pages 37 and 38 of JP-A-6-118533 and evaluated. The sample containing the compound of the present invention showed desired performance such as less increase of sensitivity and less reduction of the maximum color density when being left after exposure compared with the compound not containing the compound of the present invention.

EXAMPLE 6

Preparation of Emulsion A

A vessel in which 1 liter of water, 25 g of potassium bromide, 15 g of potassium iodide, 1.9 g of potassium thiocyanate and 24 g of gelatin was maintained at 60° C., and an aqueous solution of silver nitrate and an aqueous solution of potassium bromide were added thereto by a double jet method with vigorously stirring according to an ordinary ammonia method to thereby obtain a comparatively amorphous thick plate-shape silver iodobromide emulsion having an iodide content of 10 mol % and an average grain size of 1.0 µm. The temperature was then lowered to 35° C. and soluble salts were removed by coagulating sedimentation, then the temperature was raised to 40° C., 82 g of gelatin was added thereto, and the pH and pAg were adjusted to 6.40 and 8.80, respectively, with sodium hydroxide and sodium bromide.

After the temperature was raised to 61° C., 0.95 g of 2-phenoxyethanol was added, and further 213 mg of Sensitizing Dye-A shown below was added. After 10 minutes, 1.2 mg of sodium thiosulfate pentahydrate, 28 mg of potassium thiocyanate and 0.4 mg of chloroauric acid were added, and after 65 minutes the emulsion was solidified by cooling quickly.

Sensitizing Dye-A

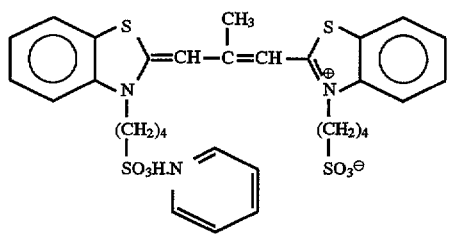

Preparation of Emulsion B

A vessel in which 1 liter of water, 25 g of potassium bromide, 9 g of potassium iodide, 7.6 g of potassium thiocyanate and 24 g of gelatin was maintained at 40° C., and an aqueous solution of silver nitrate and an aqueous solution of potassium bromide were added thereto by a double jet method with vigorously stirring according to an ordinary ammonia method to thereby obtain a comparatively amorphous thick plate-shape silver iodobromide emulsion having an iodide content of 6 mol % and an average grain size of 0.6 µm. The temperature was then lowered to 35° C. and soluble salts were removed by precipitation method, then the temperature was raised to 40° C., 110 g of gelatin was added thereto, and the pH and pAg were adjusted to 6.60 and 8.90, respectively, with sodium hydroxide sodium bromide.

After the temperature was raised to 56° C., 0.8 mg of chloroauric acid, 9 mg of potassium thiocyanate and 4 mg of sodium sulfate were added. After 55 minutes, 180 mg of Sensitizing Dye-A was added, and after 65 minutes the emulsion was solidified by cooling quickly.

Preparation of a Coated Sample

Sample 601 was prepared according to the method disclosed in JP-A-62-115035. The emulsion coating surface of the triacetyl cellulose support was previously undercoated, and the following coating solution was coated on the back surface thereof.

Compound-I                                  60 mg/m²

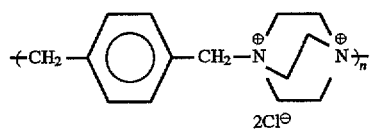

| Diacetyl Cellulose | 143 mg/m² |
| --- | --- |
| Silicon Oxide | 5 mg/m² |

The following layers were coated to prepare Sample 601.

---

First Layer: Antihalation Layer

| Gelatin | 1.0 g/m² |
| --- | --- |
| Compound-II | 140 mg/m² |
| Compound-III | 15 mg/m² |
| Dye-I | 26 mg/m² |
| Dye-II | 16 mg/m² |

Compound-II

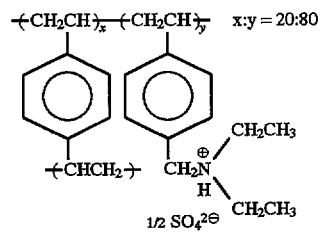   x:y = 20:80

Compound-III

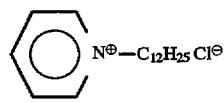

Dye-I

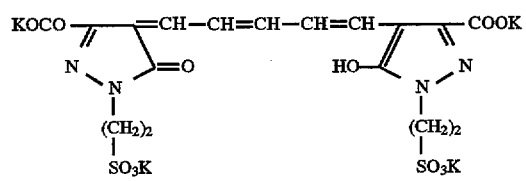

Dye-II

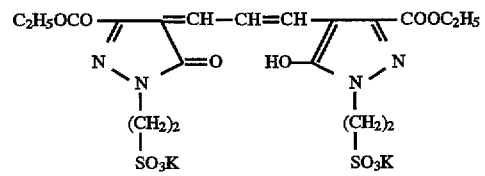

Second Layer: Interlayer

| Gelatin | 0.4 g/m² |
| --- | --- |
| Polypotassium p-Vinylbenzenesulfonate | 5 mg/m² |

Third Layer: Emulsion Layer

| Emulsion B | 1.36 g/m² |
| --- | --- |
|  | (coated weight of silver) |
| Gelatin | 2.0 g/m² |
| 4-Hydroxy-6-methyl-1,3,3a,7-tetraazaindene | 15 mg/m² |
| $C_{18}H_{35}O(CH_2CH_2O)_{25}H$ | 10 mg/m² |
| Compound-IV | 1.5 mg/m² |

| | |
|---|---|
| Polypotassium p-Vinylbenzenesulfonate | 50 mg/m² |
| Bis(vinylsulfonylacetamido)ethane | 65 mg/m² |

Compound-IV

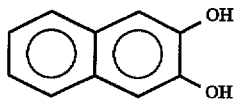

Fourth Layer: Emulsion Layer

| | |
|---|---|
| Emulsion A | 4.2 g/m² coated weight of silver |
| Gelatin | 6.5 g/m² |
| Dextran (average molecular weight: 150,000) | 1.2 g/m² |
| 4-Hydroxy-6-methyl-1,3,3a,7-tetraazaindene | 41 mg/m² |
| $C_{18}H_{35}O(CH_2CH_2O)_{25}H$ | 23 mg/m² |
| Trimethylolpropane | 500 mg/m² |
| Polypotassium p-Vinylbenzenesulfonate | 88 mg/m² |
| Polyacrylic Acid | 54 mg/m² |

Fifth Layer: Surface Protective Layer

| | |
|---|---|
| Gelatin | 0.8 g/m² |
| Compound-V | 13 mg/m² |
| Compound-VI | 50 mg/m² |
| Compound-VII | 1.8 mg/m² |
| Polypotassium p-Vinylbenzenesulfonate | 6 mg/m² |
| Polymethyl Methacrylate Fine Particles (average particle size: 3 μm) | 24 mg/m² |
| Compound-VIII | 50 mg/m² |

Compound-V

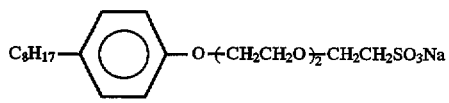

Compound-VI

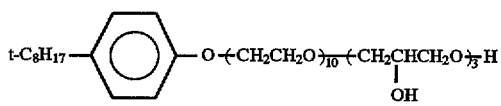

Compound-VII

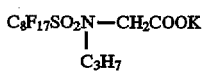

Compound-VIII

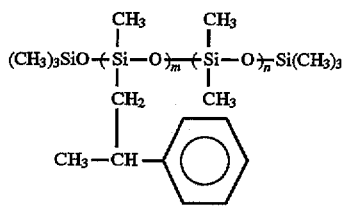

W-1

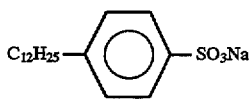

Solv-1

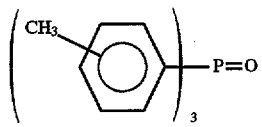

18.9 g of Compound 4 of the present invention, 19.0 g of poly-t-butyl acrylamide (molecular weight: 100,000), 9.5 g of a high boiling point organic solvent (Solv-1), 38.0 g of a surfactant (W-1) were added to 300 cc of acetic acid and dissolved by heating. This solution was added to 10% aqueous gelatin solution and dispersed in an emulsified state by a home mixer for 10 minutes.

This emulsion was added to the third and fourth layers of Sample 601 so that the amount of Compound 4 of the present invention was 0.1 mol per mol of Ag, thus Sample 603 was prepared. That which excluded Compound 4 of the present invention from the emulsion of Sample 603 was designated Sample 602, and that which used Compound 27 in place of Compound 4 of the present invention was designated Sample 604.

These samples were stored under 30° C., 65% RH conditions for 14 days after coating. Each sample was subjected to the following test.

(1) Measurement of sensitivity

Each sample was exposed for 1/100 sec through an optical wedge. A tungsten light source having color temperature of 2,854° K. was modified by a color temperature modifying filter to 5,400° K. and optical wedge exposure was carried out using this light source.

Each sample was development, fixing, washing and drying processed using an automatic processor. Each sample was measured for a certain density higher than fog density (optical density of 0.5) and the sensitivity and fog were obtained.

Developing conditions were as follows.

|  | Processing Solution | Temperature (°C.) | Time (sec) |
|---|---|---|---|
| Development | HPD | 26.5 | 55 |
| Fixing | Super Fujix DP2 | 26.5 | 76 |
| Washing | running water | 20 | 95 |
| Drying |  | 50 | 69 |

The stability of the photographic property with the lapse of time When the photographic material was left as it was after photographing was evaluated according to the following method.

Samples 601 to 604 were put under the conditions of 40° C., 60% RH for 14 days after being exposed in the above described manner. They were processed and measured in the above manner. The sensitivity was expressed as a relative value to the sensitivity of the sample processed immediately after exposure. The value nearer to zero means less fluctuation of the photographic property with the lapse of time and desired.

TABLE 4

| Sample No. | Compound | Stability with the Lapse of Time after Photographing | |
|---|---|---|---|
| | | Change of Sensitivity | Increase of Fog |
| 601 (Comparison) | — | +0.08 | 0.05 |
| 602 (Comparison) | — | +0.09 | 0.05 |
| 603 (Invention) | 4 | +0.01 | 0.02 |
| 604 (Invention) | 27 | +0.02 | 0.02 |

It is apparently understood from Table 4 that the stability with the lapse of time after photographing of the photographic material containing the compound of the present invention is extremely improved.

EXAMPLE 7

Samples were prepared in the same manner as the preparation of Sample 201 in Example 4 except that the compounds shown in Table 5 were added in the amounts indicated in Table 5 to the fourth, fifth, and ninth layers of Sample 201. Photographic performances with the lapse of time were evaluated in the same way as in Example 1 except for changing the aged conditions to 35° C., 60%, one month.

As is apparent from Table 5, the photographic material is excellent in storage stability.

TABLE 5

| Sample | Compound ($\times 10^{-5}$ mol/m$^2$) | | | Fluctuation of Photographic Performance after Photographing until Processing (35° C., 60% RH, one month) | |
|---|---|---|---|---|---|
| | Fourth Layer | Fifth Layer | Sixth Layer | Red-Sensitive Layer | Green-Sensitive Layer |
| 701 (Comparison) | — | — | — | 0.15 | 0.10 |
| 702 (Comparison) | D (7.57) | D (9.03) | D (0.12) | 0.12 | 0.09 |
| 703 (Invention) | 4 (7.57) | — | — | 0.04 | 0.10 |
| 704 (Invention) | 4 (7.57) | 4 (9.03) | — | 0.02 | 0.10 |

TABLE 5-continued

| | Compound (× 10⁻⁵ mol/m²) | | | Fluctuation of Photographic Performance after Photographing until Processing (35° C., 60% RH, one month) | |
|---|---|---|---|---|---|
| Sample | Fourth Layer | Fifth Layer | Sixth Layer | Red-Sensitive Layer | Green-Sensitive Layer |
| 705 (Invention) | 4 (7.57) | 4 (9.03) | 4 (0.12) | 0.02 | 0.03 |
| 706 (Invention) | 21 and 22 (7.57) | 21 and 22 (9.03) | 21 and 22 (0.12) | 0.03 | 0.04 |
| 707 (Invention) | 25 (7.57) | 25 (9.03) | 25 (0.12) | 0.03 | 0.04 |

While the invention has been described in detail and with reference to specific examples thereof, it will be apparent to one skilled in the art that various changes and modifications can be made therein without departing from the spirit and scope thereof.

What is claimed is:

1. A silver halide photographic material comprising a support having thereon at least one light-sensitive silver halide emulsion layer, wherein said silver halide photographic material contains at least one compound represented by the following formula (I):

wherein $R^1$ represents a substituted or unsubstituted alkyl group having from 1 to 6 carbon atoms; and $R^2$ represents a branched alkyl group having 20 or more carbon atoms, a straight chain or branched alkenyl group having 17 or more carbon atoms, or a substituted alkyl or substituted alkenyl group substituted with at least one substituent selected from the group consisting of an alkoxycarbonyl group, an alkenoxycarbonyl group, an aryloxycarbonyl group, a carbamoyl group, an alkoxyl group, an alkylthio group, an arylthio group, an alkylsulfonyl group, an arylsulfonyl group, and a heterocyclic group, said substituted alkyl or substituted alkenyl group having 12 or more carbon atoms in total.

2. The silver halide photographic material comprising a support having thereon at least one light-sensitive silver halide emulsion layer, wherein said silver halide photographic material contains at least one compound represented by the following formula (II):

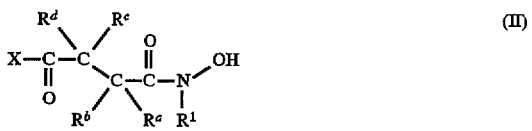

wherein $R^1$ represents a substituted or unsubstituted alkyl group having from 1 to 6 carbon atoms; $R^a$, $R^b$, $R^c$ and $R^d$ each independently represents a hydrogen atom, a substituted or unsubstituted alkyl group having from 1 to 18 carbon atoms, or a substituted or unsubstituted alkenyl group having from 2 to 18 carbon atoms; X represents —$OR^6$ or —$N(R^6)(R^7)$; and $R^6$ and $R^7$, which may be the same or different, each represents a hydrogen atom, a substituted or unsubstituted alkyl group having from 1 to 22 carbon atoms, a substituted or unsubstituted alkenyl group havig from 2 to 22 carbon atoms, or an aryl group having from 6 to 22 carbon atoms.

3. The silver halide photographic material as claimed in claim 2, wherein $R^a$ represents an alkenyl or alkyl group having from 12 to 18 carbon atoms, $R^b$, $R^c$ and $R^d$ represent hydrogen atoms, $R^1$ represents a methyl group, an ethyl group, or an n-hexyl group, X represents —$OR^6$, and $R^6$ represents an alkyl or alkenyl group having from 12 to 18 carbon atoms.

4. The silver halide photographic material as claimed in claim 2, wherein $R^c$ represents an alkenyl or alkyl group having from 12 to 18 carbon atoms, $R^a$, $R^b$ and $R^d$ represent hydrogen atoms, $R^1$ represents a methyl group, an ethyl group or an n-hexyl group, X represents —$OR^6$, and $R^6$ represents an alkyl or alkenyl group having from 12 to 18 carbon atoms.

5. The silver halide photographic material as claimed in claim 2, wherein $R^a$, $R^b$, $R^c$ and $R^d$ all represent hydrogen atoms, X represents —$OR^6$ and $R^6$ represents an alkyl or an alkenyl group having from 12 to 18 carbon atoms.

6. The silver halide photographic material as claimed in claim 2, wherein $R^a$, $R^b$, $R^c$ and $R^d$ all represent hydrogen atoms, $R^6$ represents a myristyl group, a palmityl group or a stearyl group, and $R^1$ represents a methyl group, an ethyl group or an n-hexyl group.

7. The silver halide photographic material comprising a support having thereon at least one light-sensitive silver halide emulsion layer, wherein said silver halide photographic material contains at least one compound represented by the following formula (I):

wherein $R^1$ represents a substituted or unsubstituted alkyl group having from 1 to 6 carbon atoms, and $R^2$ represents a group represented by the following formula (I-A):

$$R^4-L-R^3- \qquad \text{(I-A)}$$

wherein $R^3$ represents an alkylene group having from 2 to 20 carbon atoms or an alkenylene group having from 2 to 20 carbon atoms; $R^4$ represents a substituted or unsubstituted alkyl group having from 1 to 30 carbon atoms, a substituted or unsubstituted aryl group having from 6 to 20 carbon atoms, or a substituted or unsubstituted alkenyl group having from 2 to 18 carbon atoms; L represents —CO—, —$SO_2$—, —O—, —S—, —COO—, —OCO— or —$N(R^5)$ CO—; $R^5$ represents a hydrogen atom or a substituted or unsubstituted alkyl group having from 1 to 18 carbon atoms, provided that when L represents —O—, $R^4$ represents a substituted or unsubstituted alkyl group having from 1 to 40 carbon atoms.

8. The silver halide photographic material as claimed in claim 7, wherein $R^3$ represents 1,2-ethylene group, 1,3-propylene group or substituted 1,2-ethylene group.

9. The silver halide photographic material as claimed in claim 7, wherein $R^4$ represents a substituted or unsubstituted alkyl or alkenyl group having from 1 to 30 carbon atoms.

10. The silver halide photographic material as claimed in claim 9, wherein $R^4$ represents a substituted or unsubstituted alkyl or alkenyl group having from 6 to 22 carbon atoms.

11. The silver halide photographic material as claimed in claim 7, wherein L represents —O—, —O—CO— or —N($R^5$)CO—.

12. The silver halide photographic material as claimed in claim 7, wherein $R^4$—L— represents an alkoxycarbonyl group, an alkenoxycarbonyl group, an aryloxycarbonyl group, a carbamoyl group, an acyl group, an alkoxy group, an alkylthio group, an arylthio group, an alkylsulfonyl group or an arylsulfonyl group.

13. The silver halide photographic material as claimed in claim 7, wherein the total carbon atom number of $R^3$, L and $R^4$ is from 12 to 60.

* * * * *